United States Patent
Alimzhanov et al.

(10) Patent No.: US 12,227,577 B2
(45) Date of Patent: Feb. 18, 2025

(54) COMBINATION OF A PD-1 ANTAGONIST, AN ATR INHIBITOR AND A PLATINATING AGENT FOR THE TREATMENT OF CANCER

(71) Applicant: Merck Patent GMBH, Darmstadt (DE)

(72) Inventors: Marat Alimzhanov, Wellesley, MA (US); Patricia Soulard, Lexington, MA (US); Frank Zenke, Darmstadt (DE); Heike Dahmen, Darmstadt (DE); Astrid Zimmermann, Muehltal (DE); Andreas Schroeder, Heidelberg (DE); Keyvan Tadjalli Mehr, Heidelberg (DE); Martin Falk, Roedermark (DE)

(73) Assignee: Merck Patent GMBH, Darmstadt (DE)

(*) Notice: Subject to any disclaimer, the term of this patent is extended or adjusted under 35 U.S.C. 154(b) by 909 days.

(21) Appl. No.: 17/280,035

(22) PCT Filed: Sep. 26, 2019

(86) PCT No.: PCT/EP2019/076116
§ 371 (c)(1),
(2) Date: Mar. 25, 2021

(87) PCT Pub. No.: WO2020/064971
PCT Pub. Date: Apr. 2, 2020

(65) Prior Publication Data
US 2022/0048997 A1    Feb. 17, 2022

Related U.S. Application Data

(60) Provisional application No. 62/736,699, filed on Sep. 26, 2018.

(51) Int. Cl.
| | | |
|---|---|---|
| *C07K 16/28* | (2006.01) | |
| *A61K 31/497* | (2006.01) | |
| *A61K 31/555* | (2006.01) | |
| *A61P 35/00* | (2006.01) | |
| *G01N 33/68* | (2006.01) | |

(52) U.S. Cl.
CPC ........ *C07K 16/2827* (2013.01); *A61K 31/497* (2013.01); *A61K 31/555* (2013.01); *A61P 35/00* (2018.01); *G01N 33/6866* (2013.01); *G01N 2333/56* (2013.01); *G01N 2333/565* (2013.01); *G01N 2333/57* (2013.01); *G01N 2800/52* (2013.01)

(58) Field of Classification Search
None
See application file for complete search history.

(56) References Cited

U.S. PATENT DOCUMENTS

2014/0341917 A1   11/2014   Nastri et al.

FOREIGN PATENT DOCUMENTS

| WO | 2014089379 | 6/2014 | |
|---|---|---|---|
| WO | 2017100541 | 6/2017 | |
| WO | WO-2016137985 A1 * | 6/2019 | ........... A61K 39/395 |

OTHER PUBLICATIONS

Yap et al. Phase I modular study of AZD6738, a novel oral, potent and selective ataxia telangiectasia Rad3-related (ATR) inhibitor in combination with carboplatin, olaparib or durvalumab in patients with advanced cancers. European Journal of Cancer. 69 (Supplement 1): S2; Published: Dec. 2016 (Year: 2016).*
Lipson et al. Antagonists ofPD-1andPD-L1inCancerTreatment. Seminars in Oncology. 42(4): 587-600; Published: Aug. 28, 2015 (Year: 2015).*
Saldivar et al. The essential kinase ATR: ensuring faithful duplication of a challenging genome. Nature Reviews Molecular Cell Biology. 18: 622-636; Published: Aug. 16, 2017 (Year: 2017).*
Uchiyama. Liquid formulation for antibody drugs. (BBA—Proteins and Proteomics. 1844(11): 2041-2052; Published: Aug. 13, 2014 (Year: 2014).*
Kolar et al. Solvent selection for pharmaceuticals. Fluid Phase Equilibria. 194-197: 771-782: Published: Mar. 30, 2002 (Year: 2002).*
Nakano et al. The structural stability and catalytic activity of DNA and RNA oligonucleotides in the presence of organic solvents. Biophysical Reviews. 8(1): 11-23; Published: Jan. 11, 2016 (Year: 2016).*
Ivy et al. Follow-up for Information Letter Regarding AUC-Based Dosing of Carboplatin. National Institutes of Health; Published: Oct. 22, 2010 (Year: 2010).*
Yap et al. Phase I modular study of AZD6738, a novel oral, potent and selective ATR inhibitor in combination (combo) with carboplatin, olaparib or durvalumab in patients with advanced cancers. European Journal of Cancer. 69 (Supplement 1): S2; Published: Dec. 2016 (Year: 2016).*
Vendetti et al. The orally active and bioavailable ATR kinase inhibitor AZD6738 potentiates the anti-tumor effects of cisplatin to resolve ATM-deficient non-small cell lung cancer in vivo. Oncotarget. 6(42): 44289-44305; Published: Oct. 27, 2015 (Year: 2015).*
Mouw et al. DNA Damage and Repair Biomarkers of Immunotherapy Response. Cancer Discovery. 7(7): 675-693; Published: Jul. 5, 2017 (Year: 2017).*
Yazinski et al. ATR inhibition disrupts rewired homologous recombination and fork protection pathways in PARP inhibitor resistant BRCA-deficient cancer cells. Genes & Development. 31(3): 318-332; Published: Feb. 27, 2017 (Year: 2017).*

(Continued)

*Primary Examiner* — Juliet C Switzer
*Assistant Examiner* — Katherine Ann Holtzman
(74) *Attorney, Agent, or Firm* — HALEY GUILIANO LLP; James F. Haley, Jr.; Maha M. Saber

(57) ABSTRACT

The present invention relates to combination therapies useful for the treatment of cancer. In particular, the invention relates to a therapeutic combination which comprises a PD-1 antagonist, an ATR inhibitor and a platinating agent.

10 Claims, 17 Drawing Sheets
Specification includes a Sequence Listing.

(56) References Cited

OTHER PUBLICATIONS

Lim et al., "Abstract 3081: Precision medicine for patients with advanced small cell lung cancer treated with novel therapeutic agents in a phase 1 clinical trials unit," Cancer Research, (2017) (5 pages) (https://cancerres.aacrjournals.org/con).
Sato et al., "DNA double-strand break repair pathway regulates PD-L1 expression in cancer cells," Nature Communications, 8(1):1751 (2017) (11 pages).
Sun et al., "Inhibition of ATR downregulates PD-L1 and sensitizes tumor cells to T cell-mediated killing," American Journal of Cancer Research, 8(7):1307-1316 (2018).
Teng et al., "Pharmacologic inhibition of ATR and ATM offers clinically important distinctions to enhancing platinum or radiation response in ovarian, endometrial, and cervical cancer cells," Gynecologic Oncology,136(3):554-561 (2015).
Kurmasheva et al., "Initial testing (Stage 1) of M6620 (formerly VX-970), a novel ATR inhibitor, alone and combined with cisplatin and melphalan, by the Pediatric Preclinical Testing Program," Pediatric Blood Cancer, 65(2)e26825, pp. 1-10 (2017).
Schaaf et al., "Abstract 2223: Membranous expression of programmed cell death-ligand 1 (PDL1) on cancer cells is induced by cisplatin in an ATR dependent manner," Cancer Research, 76(14_Supplement):2223 (2016) (2 pages).

\* cited by examiner

Figure 1A

SEQ ID NO: 7 (Heavy chain sequence of avelumab)
EVQLLESGGGLVQPGGSLRLSCAASGFTFS<u>SYIMM</u>WVRQAPGKGLEWVS<u>SIYPSGGITF
YADTVKG</u>RFTISRDNSKNTLYLQMNSLRAEDTAVYYCAR<u>IKLGTVTTVDY</u>WGQGTLVTV
SSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

Figure 1B

SEQ ID NO: 8 (Heavy chain sequence of avelumab lacking the C-terminal K)
EVQLLESGGGLVQPGGSLRLSCAASGFTFS<u>SYIMM</u>WVRQAPGKGLEWVS<u>SIYPSGGITF
YADTVKG</u>RFTISRDNSKNTLYLQMNSLRAEDTAVYYCAR<u>IKLGTVTTVDY</u>WGQGTLVTV
SSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPG

Figure 2

SEQ ID NO:9 (Light chain sequence of avelumab)

QSALTQPASVSGSPGQSITISCTGTSSDVGGYNYVSWYQQHPGKAPKLMIYDVSNRPSG
VSNRFSGSKSGNTASLTISGLQAEDEADYYCSSYTSSSTRVFGTGTKVTVLGQPKANPT
VTLFPPSSEELQANKATLVCLISDFYPGAVTVAWKADGSPVKAGVETTKPSKQSNNKYA
ASSYLSLTPEQWKSHRSYSCQVTHEGSTVEKTVAPTECS

```
                            SEQUENCE LISTING

<160> NUMBER OF SEQ ID NOS: 9

<210> SEQ ID NO 1
   <211> LENGTH: 5
   <212> TYPE: PRT
   <213> ORGANISM: Artificial Sequence
   <220> FEATURE:
   <223> OTHER INFORMATION: from human Fab library

<400> SEQUENCE: 1

Ser Tyr Ile Met Met
   1               5

<210> SEQ ID NO 2
   <211> LENGTH: 17
   <212> TYPE: PRT
   <213> ORGANISM: Artificial Sequence
   <220> FEATURE:
   <223> OTHER INFORMATION: from human Fab library

<400> SEQUENCE: 2

Ser Ile Tyr Pro Ser Gly Gly Ile Thr Phe Tyr Ala Asp Thr Val Lys
   1               5                   10                  15

Gly

<210> SEQ ID NO 3
   <211> LENGTH: 11
   <212> TYPE: PRT
   <213> ORGANISM: Artificial Sequence
   <220> FEATURE:
   <223> OTHER INFORMATION: from human Fab library

<400> SEQUENCE: 3

Ile Lys Leu Gly Thr Val Thr Thr Val Asp Tyr
   1               5                   10

<210> SEQ ID NO 4
   <211> LENGTH: 14
   <212> TYPE: PRT
   <213> ORGANISM: Artificial Sequence
   <220> FEATURE:
   <223> OTHER INFORMATION: from human Fab library

<400> SEQUENCE: 4

Thr Gly Thr Ser Ser Asp Val Gly Gly Tyr Asn Tyr Val Ser
   1               5                   10

<210> SEQ ID NO 5
   <211> LENGTH: 7
   <212> TYPE: PRT
   <213> ORGANISM: Artificial Sequence
   <220> FEATURE:
   <223> OTHER INFORMATION: from human Fab library

<400> SEQUENCE: 5

Asp Val Ser Asn Arg Pro Ser
   1               5
```

```
<210> SEQ ID NO 6
<211> LENGTH: 10
<212> TYPE: PRT
<213> ORGANISM: Artificial Sequence
<220> FEATURE:
<223> OTHER INFORMATION: from human Fab library

<400> SEQUENCE: 6

Ser Ser Tyr Thr Ser Ser Ser Thr Arg Val
1               5                   10

<210> SEQ ID NO 7
<211> LENGTH: 450
<212> TYPE: PRT
<213> ORGANISM: Artificial Sequence
<220> FEATURE:
<223> OTHER INFORMATION: from human Fab library

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 8
<211> LENGTH: 449
<212> TYPE: PRT
<213> ORGANISM: Artificial Sequence
<220> FEATURE:
<223> OTHER INFORMATION: from human Fab library

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ile Met Met Trp Val Arg Gln Ala Pro Gly Lys Gly Leu Glu Trp Val
                35                  40                  45

Ser Ser Ile Tyr Pro Ser Gly Gly Ile Thr Phe Tyr Ala Asp Thr Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 9
<211> LENGTH: 216
<212> TYPE: PRT
<213> ORGANISM: Artificial Sequence
<220> FEATURE:
<223> OTHER INFORMATION: from human Fab library

<400> SEQUENCE: 9

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110
```

```
Pro Lys Ala Asn Pro Thr Val Thr Leu Phe Pro Pro Ser Ser Glu Glu
    115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

COMBINATION OF A PD-1 ANTAGONIST, AN ATR INHIBITOR AND A PLATINATING AGENT FOR THE TREATMENT OF CANCER

CROSS-REFERENCE TO RELATED APPLICATIONS

This application is a United States National Phase Application filed under 35 U.S.C. § 371 from International Patent Application No. PCT/EP2019/076116, filed on Sep. 26, 2019, which claims benefit of U.S. Provisional Application No. 62/736,699, filed Sep. 26, 2018. The contents and disclosures of each of these applications are incorporated by reference herein in their entireties.

The Sequence Listing associated with this application is provided in text format in lieu of a paper copy and is hereby incorporated by reference in the specification. The name of the text file containing the Sequence Listing is 000184-0012-301-SL.txt. The text file was created on Mar. 25, 2021 and is 11,484 bytes in size and is being submitted electronically via EFS-Web.

FIELD OF INVENTION

The present invention relates to a therapeutic combination useful for the treatment of cancer. In particular, the invention relates to a therapeutic combination which comprises a PD-1 antagonist, an ATR inhibitor and a platinating agent.

BACKGROUND OF THE INVENTION

The mechanism of co-stimulation of T-cells has gained significant therapeutic interest in recent years for its potential to enhance cell-based immune response. Costimulatory molecules expressed on antigen-presenting cells (APCs) promote and induce T-cells to promote clonal expansion, cytokine secretion and effector function. In the absence of co-stimulation, T-cells can become refractory to antigen stimulation, do not mount an effective immune response, and further may result in exhaustion or tolerance to foreign antigens (Lenschow et al., Ann. Rev. Immunol. (1996) 14: 233). Recently, it has been discovered that T cell dysfunction or anergy occurs concurrently with an induced and sustained expression of the inhibitory receptor, programmed death-1 polypeptide (PD-1). The programmed death 1 (PD-1) receptor and PD-1 ligands 1 and 2 (PD-L1 and PD-L2, respectively) play integral roles in immune regulation. Expressed on activated T cells, PD-1 is activated by PD-L1 (also known as B7-H1) and PD-L2 expressed by stromal cells, tumor cells, or both, initiating T-cell death and localized immune suppression (Dong et al. (1999) Nat Med 5: 1365; Freeman et al. (2000) J Exp Med 192: 1027), potentially providing an immune-tolerant environment for tumor development and growth.

Conversely, inhibition of this interaction can enhance local T-cell responses and mediate antitumor activity in nonclinical animal models (Iwai et al. (2002) PNAS USA 99: 12293). As a result, a number of monoclonal antibodies (mAbs) agents targeting the axis PD-1/PD-L1 are being studied for various cancers, and hundreds of clinical trials on anti-PD-1 and anti-PD-L1 mAbs are under active development.

PD-L1 is expressed in a broad range of cancers with a high frequency, up to 88% in some types of cancer. In a number of these cancers, including lung, renal, pancreatic, and ovarian cancers, the expression of PD-L1 is associated with reduced survival and an unfavorable prognosis. Interestingly, the majority of tumor infiltrating T lymphocytes predominantly express PD-1, in contrast to T lymphocytes in normal tissues and peripheral blood T lymphocytes, indicating that up-regulation of PD-1 on tumor-reactive T cells can contribute to impaired anti-tumor immune responses (Ahmadzadeh et al. (2009) Blood 14(8): 1537). This may be due to exploitation of PD-L1 signaling mediated by PD-L1 expressing tumor cells interacting with PD-1 expressing T cells to result in attenuation of T cell activation and evasion of immune surveillance (Keir et al. (2008) Annu. Rev. Immunol. 26: 677).

Genotoxic stress, as caused by platinating agents, leads to an upregulation of PD-L1 expression in cancer cells, which may limit anti-tumor immunity. According to several reports, PD-L1 upregulation is reversed again by the concurrent inhibition of the ATR kinase, which is involved in the DNA double-stranded break repair pathway (Sato et al. (2017) Nat Commun. November 24; 8(1):1751; Schaaf et al. AACR, Cancer Res 2016; 76(14 Suppl):Abstract nr 2223; Teng et al. (2017) Gynecologic Oncology 145(1):37-38). Accordingly, it is believed that ATR inhibition not only sensitizes cancer cells to platinating agents by inhibiting DNA repair, but also by inhibiting PD-L1 expression to restore anti-tumor immune response.

There remains a need to develop novel therapeutic options for the treatment of cancers. Furthermore, there is a need for therapies having greater efficacy than existing therapies. Preferred combination therapies of the present invention show greater efficacy than treatment with either therapeutic agent alone.

SUMMARY OF THE INVENTION

Each of the embodiments described below can be combined with any other embodiment described herein not inconsistent with the embodiment with which it is combined. Furthermore, each of the embodiments described herein envisions within its scope pharmaceutically acceptable salts of the compounds described herein. Accordingly, the phrase "or a pharmaceutically acceptable salt thereof" is implicit in the description of all compounds described herein. Embodiments within an aspect as described below can be combined with any other embodiments not inconsistent within the same aspect or a different aspect.

Despite the prior art findings that PD-L1 upregulation, which is induced by platinating agent, could be reversed by the concurrent treatment with an ATR inhibitor, the inventors surprisingly found that the anti-tumor activity of the combined administration of a platinating agent and an ATR inhibitor could be further augmented by administering these in combination with an inhibitor of the PD-1 pathway.

Without being bound by theory, possible explanations for the enhanced effect include mechanisms leading to enhanced tumor-antigen presentation/generation or the induction of cyto-/chemokines attracting cytotoxic lymphocytes to kill the tumor cells. In combination with chemotherapies like a platinating agent, ATR inhibition may enhance cell killing and exposure of damage associated molecular patterns (ATP, Calreticulin, HMGB1, HSP70) leading to the activation of dendritic cells and an enhanced T cell response, also known as immunogenic cell death. As a key regulator of the DNA Damage Response during replication stress, ATR inhibition may lead to genomic aberrations which in turn may increase the mutational burden of the tumor cells leading to generation of new antigens. Damaged DNA may activate intracellular sensing mechanisms which in turn stimulate a signaling cascade leading to the release of cytokines into the tumor microenvironment which can potentially attract immune cells to attack the tumor cells.

Thus, in a first aspect, the present invention provides a therapeutic combination comprising a PD-1 antagonist, an ATR inhibitor and a platinating agent. The combination of compounds is suitable for use in a method comprising administering to the subject the compounds for treating a cancer in a subject in need thereof. Likewise, the compounds are suitable for use in methods of inhibiting tumor growth or progression in a subject who has malignant tumors. Also provided is the use of the compounds in methods of inhibiting metastasis of malignant cells in a subject. Also provided is the use of the compounds in methods of decreasing the risk of metastasis development and/or metastasis growth in a subject. Also provided is the use of the compounds in methods of inducing tumor regression in a subject who has malignant cells. The combination treatment results in an objective response, preferably a complete response or partial response in the subject. Also provided is the use of said combination of compounds for the manufacture of a medicament for use in the above methods of treatment.

In some embodiments, the cancer is identified as PD-L1 positive cancerous disease.

Specific types of cancer to be treated according to the invention include, but are not limited to, cancer of the ovary, peritoneum, fallopian tube, lung, head and neck, colon, neuroendocrine system, urothelium, prostate, esophagus, bladder, stomach, mesenchyme, breast, pancreas, and histological subtypes thereof. In some embodiments, the cancer is selected from small-cell lung cancer (SCLC), non-small-cell lung cancer (NSCLC), squamous cell carcinoma of the head and neck (SCCHN), colorectal cancer (CRC), primary neuroendocrine tumors and sarcoma or PARPi-resistant recurrent cancer selected from ovarian, primary peritoneal, and fallopian tube cancer. In some preferred embodiments, the cancer is a PARPi-resistant recurrent cancer selected from ovarian, primary peritoneal, and fallopian tube cancer.

The above-mentioned triple combination can be administered in a first-line, second-line or higher treatment (i.e., beyond therapy in subjects) of the cancer. In some embodiments, ovarian cancer, primary peritoneal cancer, fallopian tube cancer, SCLC extensive disease (ED), NSCLC and SCCHN are selected for first-line treatment. In some embodiments, the cancer is resistant or became resistant to prior cancer therapy. The combination therapy of the invention can also be used in the treatment of a subject with the cancer who has been previously treated with one or more chemotherapies or underwent radiotherapy but failed with such previous treatment. The cancer for second-line or beyond treatment can be ovarian cancer, primary peritoneal cancer, fallopian tube cancer, pre-treated relapsing metastatic NSCLC, unresectable locally advanced NSCLC, SCLC ED, pre-treated SCLC ED, SCLC unsuitable for systemic treatment, pre-treated relapsing or metastatic SCCHN, recurrent SCCHN eligible for re-irradiation, pre-treated microsatellite status instable low (MSI-L) or microsatellite status stable (MSS) metastatic colorectal cancer (mCRC), pre-treated subset of patients with mCRC (i.e., MSI-L or MSS), and unresectable or metastatic microsatellite instable high (MSI-H) or mismatch repair-deficient solid tumors progressing after prior treatment and which have no satisfactory alternative treatment options. In some embodiments, a PARPi-resistant recurrent cancer selected from ovarian, primary peritoneal, and fallopian tube cancer is treated with the combination of a PD-1 antagonist, an ATR inhibitor and a platinating agent.

In some embodiments, said triple combination is used in the treatment of a human subject.

In some embodiments, the PD-1 antagonist is an anti-PD-1 or anti-PD-L1 antibody. Preferably, the PD-1 antagonist is an anti-PD-L1 antibody, which comprises a heavy chain, which comprises three complementarity determining regions (CDRs) having amino acid sequences of SEQ ID NOs: 1, 2 and 3, and a light chain, which comprises three complementarity determining regions (CDRs) having amino acid sequences of SEQ ID NOs: 4, 5 and 6. The anti-PD-L1 antibody preferably comprises the heavy chain having amino acid sequences of SEQ ID NOs: 7 or 8 and the light chain having amino acid sequence of SEQ ID NO: 9. In some preferred embodiments, the anti-PD-L1 antibody is avelumab.

In some embodiment, the anti-PD-1 or anti-PD-L1 antibody, preferably avelumab, is administered intravenously (e.g., as an intravenous infusion) or subcutaneously, preferably intravenously. More preferably, the antibody is administered as an intravenous infusion. Most preferably, the antibody is administered for 50-80 minutes, highly preferably as a one-hour intravenous infusion. In some embodiment, the antibody is administered at a dose of about 10 mg/kg body weight every other week (i.e., every two weeks, or "Q2W"). In some embodiments, the antibody is administered at a fixed dosing regimen of 800 mg as a 1 hour IV infusion Q2W. In another embodiment, the antibody is administered at a dose of about 20 mg/kg body weight every three weeks ("Q3W"). In some embodiments, the antibody is administered at a fixed dosing regimen of 1600 mg as an IV infusion Q3W.

In some aspects, the ATR inhibitor is represented by one of the following formulae:

Compound 1

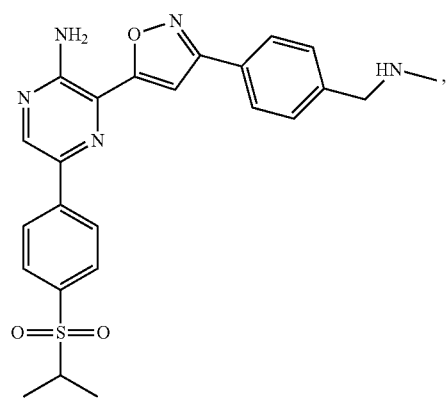

-continued

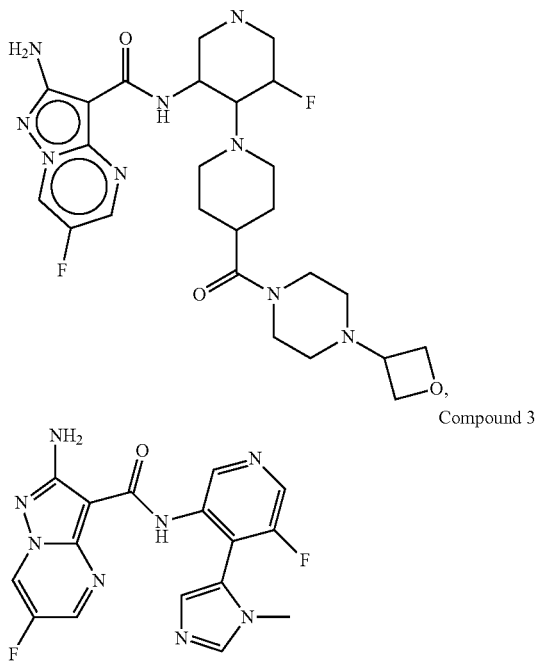

Compound 2

Compound 3 or a pharmaceutically acceptable salt thereof.

In some embodiments, the platinating agent is selected from the group consisting of cisplatin, carboplatin, oxaliplatin, nedaplatin, lobaplatin, triplatin, tetranitrate, heptaplatin, picoplatin, ProLindac (CAS number 674289-90-8), Lipoplatin (liposomally encapsulated form of cisplatin), aroplatin and satraplatin. In a preferred embodiment, the platinating agent is carboplatin, oxaliplatin or cisplatin, more preferably carboplatin.

In other embodiments, the PD-1 antagonist, ATR inhibitor and platinating agent are used in combination with radiotherapy (RT), a further chemotherapy (CT), or chemoradiotherapy (CRT).

In a further aspect, the disclosure provides a method for advertising a PD-1 antagonist in combination with an ATR inhibitor and a platinating agent, comprising promoting, to a target audience, the use of the combination for treating a subject with a cancer.

Provided herein is also a pharmaceutical composition comprising a PD-1 antagonist, an ATR inhibitor and a platinating agent and at least a pharmaceutically acceptable excipient or adjuvant.

In a further aspect, the invention relates to a kit comprising a PD-1 antagonist and a package insert comprising instructions for using the PD-1 antagonist in combination with an ATR inhibitor and a platinating agent to treat or delay progression of a cancer in a subject. Also provided is a kit comprising an ATR inhibitor and a package insert comprising instructions for using the ATR inhibitor in combination with a PD-1 antagonist and a platinating agent to treat or delay progression of a cancer in a subject. Also provided is a kit comprising a platinating agent and a package insert comprising instructions for using the platinating agent in combination with a PD-1 antagonist and an ATR inhibitor to treat or delay progression of a cancer in a subject.

In various embodiments, the PD-1 antagonist of the therapeutic combination is avelumab, the ATR inhibitor is any one of Compounds 1 to 5, or a pharmaceutically acceptable salt thereof, and the platinating agent is carboplatin.

BRIEF DESCRIPTION OF THE FIGURES

FIGS. 1A and 1B show the heavy chain sequence of avelumab. In FIG. 1A, SEQ ID NO: 7 represents the full length heavy chain sequence of avelumab. The CDRs having the amino acid sequences of SEQ ID NOs: 1, 2 and 3 are marked by underlining. In FIG. 1B, SEQ ID NO: 8 represents the heavy chain sequence of avelumab without the C-terminal lysine. The CDRs having the amino acid sequences of SEQ ID NOs: 1, 2 and 3 are marked by underlining.

FIG. 2 (SEQ ID NO: 9) shows the light chain sequence of avelumab. The CDRs having the amino acid sequences of SEQ ID NOs: 4, 5 and 6 are marked by underlining.

DETAILED DESCRIPTION OF THE INVENTION

Definitions

Figure 3A:
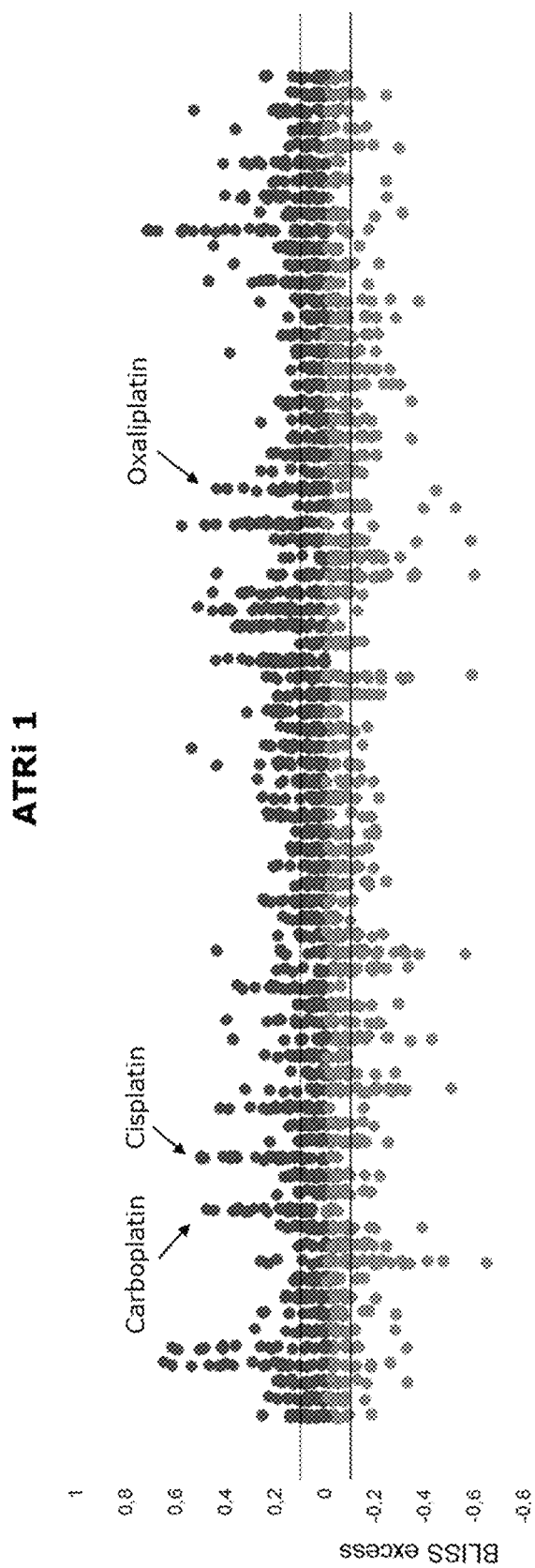
FIGS. 3A and 3B show the combination effect of two ATR inhibitors with various chemotherapeutic agents, including the platinating agents carboplatin, cisplatin and oxaliplatin on the cell growth of 35 cancer cell lines. The combination effect is expressed as BLISS excess over the additive monotherapy effects. Positive BLISS excess values are synergistic effects, and negative BLISS excess values are antagonistic effects. Values between −0.1 and 0.1 are considered close to the linear combination effect.

"A", "an", and "the" include plural referents unless the context clearly dictates otherwise. Thus, for example, reference to an antibody refers to one or more antibodies or at least one antibody.

As such, the terms "a" (or "an"), "one or more", and "at least one" are used interchangeably herein.

"About" when used to modify a numerically defined parameter (e.g., the dose of a compound, or the length of treatment time with a combination therapy described herein) means that the parameter may vary by as much as 10% below or above the stated numerical value for that parameter. For example, a dose of about 10 mg/kg may vary between 9 mg/kg and 11 mg/kg.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. E.g., a physician who instructs a patient to self-administer a drug or provides a patient with a prescription for a drug is administering the drug to the patient.

"Antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also, unless otherwise specified, any antigen-binding fragment or antibody fragment thereof that competes with the intact antibody for specific binding, fusion proteins comprising an antigen-binding portion (e.g., antibody-drug conjugates), any other modified configuration of the immunoglobulin molecule that comprises an antigen recognition site, antibody compositions with poly-epitopic specificity, and multi-specific antibodies (e.g., bispecific antibodies).

"Antigen-binding fragment" of an antibody or "antibody fragment" comprises a portion of an intact antibody, which is still capable of antigen binding and/or the variable region of the intact antibody. Antigen-binding fragments include, for example, Fab, Fab', F(ab')$_2$, Fd, and Fv fragments, domain antibodies (dAbs, e.g., shark and camelid antibodies), fragments including complementarity determining regions (CDRs), single chain variable fragment antibodies (scFv), single-chain antibody molecules, multi-specific antibodies formed from antibody fragments, maxibodies, minibodies, intrabodies, diabodies, triabodies, tetrabodies, v-NAR and bis-scFv, linear antibodies (see e.g., U.S. Pat. No. 5,641,870, Example 2; Zapata et al. (1995) Protein Eng. 8HO: 1057), and polypeptides that contain at least a portion of an immunoglobulin that is sufficient to confer specific antigen binding to the polypeptide. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment, which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments were originally produced as pairs of Fab' fragments which have hinge cysteines between them. Other chemical couplings of antibody fragments are also known.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils, and macrophages) enable these cytotoxic effector cells to bind specifically to an antigen-bearing target cell and subsequently kill the target cell with cytotoxins. The antibodies arm the cytotoxic cells and are required for killing of the target cell by this mechanism. The primary cells for mediating ADCC, the NK cells, express FcγRIII only, whereas monocytes express FcγRI, FcγRII and FcγRIII. Fc expression on hematopoietic cells is summarized in Table 3 on page 464 of Ravetch and Kinet, Annu. Rev. Immunol. 9: 457-92 (1991).

"Anti-PD-L1 antibody" or "anti-PD-1 antibody" means an antibody that blocks binding of PD-L1 expressed on a cancer cell to PD-1. In any of the treatment method, medicaments and uses of the present invention in which a human subject is being treated, the anti-PD-L1 antibody specifically binds to human PD-L1 and blocks binding of human PD-L1 to human PD-1 and the anti-PD-1 antibody specifically binds to human PD-1 and blocks binding of human PD-1 to human PD-L1. The antibody may be a monoclonal antibody, human antibody, humanized antibody or chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen-binding fragment is selected from the group consisting of Fab, Fab'-SH, F(ab')2, scFv and Fv fragments. Examples of monoclonal antibodies that bind to human PD-L1, and useful in the treatment method, medicaments and uses of the present invention, are described in WO 2007/005874, WO 2010/036959, WO 2010/077634, WO 2010/089411, WO 2013/019906, WO 2013/079174, WO 2014/100079, WO 2015/061668, and U.S. Pat. Nos. 8,552,154, 8,779,108 and 8,383,796. Specific anti-human PD-L1 or anti-human PD-1 monoclonal antibodies useful as the PD-1 antagonist in the treatment method, medicaments and uses of the present invention include, for example without limitation, avelumab (MSB0010718C), nivolumab (BMS-936558), pembrolizumab, mAb7 (also referred to as RN888 or PF-6801591) as described in WO2016/092419, atezolizumab, durvalumab, cemiplimab, MPDL3280A (an IgG1-engineered, anti-PD-L1 antibody), BMS-936559 (a fully human, anti-PD-L1, IgG4 monoclonal antibody), MED14736 (an engineered IgG1 kappa monoclonal antibody with triple mutations in the Fc domain to remove antibody-dependent, cell-mediated cytotoxic activity), and an antibody which comprises the heavy chain and light chain variable regions of SEQ ID NO:24 and SEQ ID NO:21, respectively, of WO 2013/019906.

"ATR inhibitor" or "ATRi" refers to an inhibitor of the ATR kinase pathway, which mediates the DNA damage response. Preferably, the ATR inhibitor is a molecule that inhibits the enzymatic activity of the ATR kinase. Examples of ATR inhibitors that are useful in the treatment method, medicaments and uses of the present invention include any of the Compounds 1 to 5, or a pharmaceutically acceptable salt thereof. Further ATR inhibitors are described in WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO 2014/143242, WO 2014/143241, WO 2015/084384, WO 2014/143240, WO 2015/187451, WO 2015/085132, WO 2014/062604, WO 2014/143240, WO 2013/071094, WO 2013/071093, WO 2013/071090, WO 2013/071088, WO 2013/049859, WO 2013/049719, WO 2013/049720, WO 2013/049722, WO 2012/138,938, WO 2011/163527, WO 2011/143,423, WO 2011/143,426, WO 2011/143,399, and/or WO 2010/054398.

"Biomarker" generally refers to biological molecules, and quantitative and qualitative measurements of the same, that are indicative of a disease state. "Prognostic biomarkers" correlate with disease outcome, independent of therapy. For example, tumor hypoxia is a negative prognostic marker—the higher the tumor hypoxia, the higher the likelihood that the outcome of the disease will be negative. "Predictive biomarkers" indicate whether a patient is likely to respond positively to a particular therapy. E.g., HER2 profiling is commonly used in breast cancer patients to determine if those patients are likely to respond to Herceptin (trastuzumab, Genentech). "Response biomarkers" provide a measure of the response to a therapy and so provide an indication of whether a therapy is working. For example, decreasing levels of prostate-specific antigen generally indicate that anti-cancer therapy for a prostate cancer patient is working. When a marker is used as a basis for identifying or selecting a patient for a treatment described herein, the marker can be measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of a biomarker in a clinical setting is a clear indication that this parameter was used as a basis for initiating, continuing, adjusting and/or ceasing administration of the treatments described herein.

"Cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, urothelial cancer and head and neck cancer.

"Chemotherapy" is a therapy involving a chemotherapeutic agent, which is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide, and trimethylolomelamine; acetogenins (especially bullatacin and bullatacinone); delta-9-tetrahydrocannabinol (dronabinol); beta-lapachone; lapachol; colchicines; betulinic acid; bryostatin; pemetrexed; callystatin; CC-1065 (including its adozelesin, carzelesin, and bizelesin synthetic analogues); podophyllotoxin; podophyllinic acid; teniposide; cryptophycins (particularly, cryptophycin 1 and cryptophycin 8); dolastatin; duocarmycin (including the synthetic analogues KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al. (1994) Angew. Chem Intl. Ed. Engl. 33: 183); dynemicin including dynemicin A; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HCl liposome injection, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites such as methotrexate, gemcitabine, tegafur, capecitabine, an epothilone, and 5-fluorouracil (5-FU); folic acid analogues such as denopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, and trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially, T-2 toxin, verracurin A, roridin A, and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; ifosfamide; mitoxantrone; vincristine; oxaliplatin; leucovovin; vinorelbine; novantrone; edatrexate; daunomycin; aminopterin; ibandronate; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine and prednisolone, or FOLFOX, an abbreviation for a treatment regimen with oxaliplatin combined with 5-FU and leucovovin.

"Clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity, or side effect.

"Complete response" or "complete remission" refers to the disappearance of all signs of cancer in response to treatment. This does not always mean the cancer has been cured.

"Comprising", as used herein, is intended to mean that the compositions and methods include the recited elements, but not excluding others. "Consisting essentially of", when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

"Enhancing T-cell function" means to induce, cause or stimulate a T-cell to have a sustained or amplified biological function, or renew or reactivate exhausted or inactive T-cells. Examples of enhancing T-cell function include: increased secretion of y-interferon from CD8+ T-cells, increased proliferation, increased antigen responsiveness (e.g., viral, pathogen, or tumor clearance) relative to such levels before the intervention. In one embodiment, the level of. enhancement is as least 50%, alternatively 60%, 70%, 80%, 90%, 100%, 120%, 150%, 200%. The manner of measuring this enhancement is known to one of ordinary skill in the art.

"Fc" is a fragment comprising the carboxy-terminal portions of both H chains held together by disulfides. The effector functions of antibodies are determined by sequences in the Fc region, the region which is also recognized by Fc receptors (FcR) found on certain types of cells.

"Functional fragments" of the antibodies of the invention comprise a portion of an intact antibody, generally including the antigen-binding or variable region of the intact antibody or the Fc region of an antibody which retains or has modified FcR binding capability. Examples of functional antibody fragments include linear antibodies, single-chain antibody molecules, and multi-specific antibodies formed from antibody fragments.

"Fv" is the minimum antibody fragment, which contains a complete antigen-recognition and antigen-binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen-binding specificity to the antibody. However, even a single variable domain (or half of an Fv comprising only three HVRs specific for an antigen) has the ability to recognize and bind antigen, although at a lower affinity than the entire binding site.

"Human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (see e.g., Hoogenboom and Winter (1991), JMB 227: 381; Marks et al. (1991) JMB 222: 581). Also available for the preparation of human monoclonal antibodies are methods described in Cole et al. (1985) Monoclonal Antibodies and Cancer Therapy, Alan R. Liss, page 77; Boerner et al. (1991), J. Immunol 147(l): 86; van Dijk and van de Winkel (2001) Curr. Opin. Pharmacol 5: 368). Human antibodies can be prepared by administering the antigen to a transgenic animal that has been modified to produce such antibodies in response to antigenic challenge but whose endogenous loci have been disabled, e.g., immunized xenomice (see e.g., U.S. Pat. Nos. 6,075,181; and 6,150,584 regarding XENOMOUSE technology). See also, for example, Li et al. (2006) PNAS USA, 103: 3557, regarding human antibodies generated via a human B-cell hybridoma technology.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit, or non-human primate having the desired specificity, affinity and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and no more than 3 in the L chain. The humanized antibody optionally will also comprise at least a portion of an immunoglobulin constant region (Fc), typically that of a human immunoglobulin. For further details, see e.g., Jones et al. (1986) Nature 321: 522; Riechmann et al. (1988), Nature 332: 323; Presta (1992) Curr. Op. Struct. Biol. 2: 593; Vaswani and Hamilton (1998), Ann. Allergy, Asthma & Immunol. 1: 105; Harris (1995) Biochem. Soc. Transactions 23: 1035; Hurle and Gross (1994) Curr. Op. Biotech. 5: 428; and U.S. Pat. Nos. 6,982,321 and 7,087,409.

"Immunoglobulin" (Ig) is used interchangeably with "antibody" herein. The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intra-chain disulfide bridges. Each H chain has, at the N-terminus, a variable domain ($V_H$) followed by three constant domains ($C_H$) for each of the α and γ chains and four $C_H$ domains for µ and E isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., Basic and Clinical Immunology, $8^{th}$ Edition, Sties et al. (eds.), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and µ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1, and IgK1.

"Infusion" or "infusing" refers to the introduction of a drug-containing solution into the body through a vein for therapeutic purposes. Generally, this is achieved via an intravenous (IV) bag.

"In combination with" or "in conjunction with" refers to the administration of one compound in addition to one or more other compound. As such, "in combination with" or "in conjunction with" refers to the administration of one compound in addition to the administration of one or more other compound in any order. For instance, the one compound may be administered before, during, or after administration of the one or more other compound to the individual. As used herein, the term "in combination" with in regard to the administration of the triple combination comprising the PD-1 antagonist, the ATR inhibitor and the platinating agent means that these compounds are administered to the patient in any order. For instance, all compounds may be administered simultaneously or sequentially. Also, two compounds may be administered simultaneously, followed by the sequential administration of the third compound. Also, the compounds may be administered as a single or separate compositions, formulations or unit dosage forms. Also, two compounds may be administered as a single composition, formulation or unit dosage form, whereas the third compound is administered as a separate composition, formulation or unit dosage form. It will be appreciated that the PD-1 antagonist, the ATR inhibitor and the platinating agent are administered on the same day or on different days and in any order as according to an appropriate dosing protocol.

"Metastatic" cancer refers to cancer which has spread from one part of the body (e.g., the lung) to another part of the body.

"Monoclonal antibody", as used herein, refers to an antibody obtained from a population of substantially homogeneous antibodies, i.e., the individual antibodies comprising the population are identical except for possible naturally occurring mutations and/or post-translation modifications (e.g., isomerizations and amidations) that may be present in minor amounts. Monoclonal antibodies are highly specific, being directed against a single antigenic site. In contrast to polyclonal antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture and uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including, for example, the hybridoma method (e.g., Kohler and Milstein (1975) Nature 256: 495; Hongo et al. (1995) Hybridoma 14 (3): 253; Harlow et al. (1988) Antibodies: A Laboratory Manual (Cold Spring Harbor Laboratory Press, $2^{nd}$ ed.; Hammerling et al. (1981) In: Monoclonal Antibodies and T-Cell Hybridomas 563 (Elsevier, N.Y.), recombinant DNA methods (see e.g., U.S. Pat. No. 4,816,567), phage-display technologies (see e.g., Clackson et al. (1991) Nature 352: 624; Marks et al. (1992) JMB 222: 581; Sidhu et al. (2004) JMB 338(2): 299; Lee et al. (2004) JMB 340(5): 1073; Fellouse (2004) PNAS USA 101(34): 12467; and Lee et al. (2004) J. Immunol. Methods 284(1-2): 119), and technologies for producing human or human-like antibodies in animals that have parts or all of the human immunoglobulin loci or genes encoding human immunoglobulin sequences (see e.g., WO 1998/24893; WO 1996/34096; WO 1996/33735; WO 1991/10741; Jakobovits et al. (1993) PNAS USA 90: 2551; Jakobovits et al. (1993) Nature 362: 255; Bruggemann et al. (1993) Year in Immunol. 7: 33; U.S. Pat. Nos. 5,545,807; 5,545,806; 5,569,825; 5,625,126; 5,633,425; and U.S. Pat. No. 5,661,016; Marks et al. (1992) Bio/Technology 10: 779; Lonberg et al. (1994) Nature 368: 856; Morrison (1994) Nature 368: 812; Fishwild et al. (1996) Nature Biotechnol. 14: 845; Neuberger (1996), Nature Biotechnol. 14: 826; and Lonberg and Huszar (1995), Intern. Rev. Immunol. 13: 65-93). The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (see e.g., U.S. Pat. No. 4,816,567; Morrison et al. (1984) PNAS USA, 81: 6851).

"Objective response" refers to a measurable response, including complete response (CR) or partial response (PR).

"PARPi-resistant" tumors or cancers are tumors or cancers, which cannot, or can no longer, be treated with PARP inhibitors. PARPi-resistance may already be present before the first treatment attempt with a PARPi. PARPi-resistance may also be acquired after the initial treatment with a PARPi, in some instances as a result of the treatment.

"Partial response" refers to a decrease in the size of one or more tumors or lesions, or in the extent of cancer in the body, in response to treatment.

"Patient" and "subject" are used interchangeably herein to refer to a mammal in need of treatment for a cancer. Generally, the patient is a human diagnosed or at risk for suffering from one or more symptoms of a cancer. In certain embodiments a "patient" or "subject" may refer to a non-human mammal, such as a non-human primate, a dog, cat, rabbit, pig, mouse, or rat, or animals used in screening, characterizing, and evaluating drugs and therapies.

"PD-1 antagonist" refers to an agent inhibiting the PD-1 pathway by blocking the interaction between PD-1 and PD-L1. Preferably, the PD-1 antagonist is an antibody. More preferably, the PD-1 antagonist is an anti-PD-1 or anti-PD-L1 antibody. Most preferably, the PD-1 antagonist is avelumab.

"PD-L1 expression" as used herein means any detectable level of expression of PD-L1 protein on the cell surface or of PD-L1 mRNA within a cell or tissue. PD-L1 protein expression may be detected with a diagnostic PD-L1 antibody in an IHC assay of a tumor tissue section or by flow cytometry. Alternatively, PD-L1 protein expression by tumor cells may be detected by PET imaging, using a binding agent (e.g., antibody fragment, affibody and the like) that specifically binds to PD-L1. Techniques for detecting and measuring PD-L1 mRNA expression include RT-PCR and real-time quantitative RT-PCR.

"PD-L1 positive" cancer, including a "PD-L1 positive" cancerous disease, is one comprising cells, which have PD-L1 present at their cell surface. The term "PD-L1 positive" also refers to a cancer that produces sufficient levels of PD-L1 at the surface of cells thereof, such that an anti-PD-L1 antibody has a therapeutic effect, mediated by the binding of the said anti-PD-L1 antibody to PD-L1.

"Pharmaceutically acceptable" indicates that the substance or composition must be chemically and/or toxicologically suitable for the treatment of mammals.

The term "pharmaceutically acceptable adjuvant" refers to any and all substances which enhance the body's immune response to an antigen. Non-limiting examples of pharmaceutically acceptable adjuvants are: Alum, Freund's Incomplete Adjuvant, MF59, synthetic analogs of dsRNA such as poly(I:C), bacterial LPS, bacterial flagellin, imidazolquinolines, oligodeoxynucleotides containing specific CpG motifs, fragments of bacterial cell walls such as muramyl dipeptide and Quil-A*.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition.

"Pharmaceutically acceptable salt" of a molecule refers to the salt form of the molecule. A pharmaceutically acceptable salt may involve the inclusion of another molecule, such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "platinating agent" is an alkylating agent which inter alia binds covalently to DNA and cross-links DNA strands, resulting in inhibition of DNA synthesis and function as well as inhibition of transcription. A platinating agent can be any platinum-based chemotherapeutic agent. In some embodiments, the platinating agent is selected from cisplatin, carboplatin, oxaliplatin, nedaplatin, lobaplatin, triplatin, tetranitrate, heptaplatin, picoplatin, ProLindac (CAS number 674289-90-8), Lipoplatin (liposomally encapsulated form of cisplatin), aroplatin and satraplatin.

"Recurrent" cancer is one which has regrown, either at the initial site or at a distant site, after a response to initial therapy, such as surgery. A locally "recurrent" cancer is cancer that returns after treatment in the same place as a previously treated cancer.

"Reduction" of a symptom or symptoms (and grammatical equivalents of this phrase) refers to decreasing the severity or frequency of the symptom(s), or elimination of the symptom(s).

"Serum" refers to the clear liquid that can be separated from clotted blood. Serum differs from plasma, the liquid portion of normal unclotted blood containing the red and white cells and platelets. Serum is the component that is neither a blood cell (serum does not contain white or red blood cells) nor a clotting factor. It is the blood plasma not including the fibrinogens that help in the formation of blood clots. It is the clot that makes the difference between serum and plasma.

"Single-chain Fv", also abbreviated as "sFv" or "scFv", are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see e.g., Pluckthun (1994), In: The Pharmacology of Monoclonal Antibodies, vol. 113, Rosenburg and Moore (eds.), Springer-Verlag, New York, pp. 269.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Systemic" treatment is a treatment, in which the drug substance travels through the bloodstream, reaching and affecting cells all over the body.

"Therapeutically effective amount" of a PD-1 antagonist, an ATR inhibitor or a platinating agent, in each case of the invention, refers to an amount effective, at dosages and for periods of time necessary, that, when administered to a patient with a cancer, will have the intended therapeutic effect, e.g., alleviation, amelioration, palliation, or elimination of one or more manifestations of the cancer in the patient, or any other clinical result in the course of treating a cancer patient. A therapeutic effect does not necessarily occur by administration of one dose and may occur only after administration of a series of doses. Thus, a therapeutically effective amount may be administered in one or more administrations. Such therapeutically effective amount may vary according to factors such as the disease state, age, sex, and weight of the individual, and the ability of a PD-1 antagonist, an ATR inhibitor or a platinating agent to elicit a desired response in the individual. A therapeutically effective amount is also one in which any toxic or detrimental effects of a PD-1 antagonist, an ATR inhibitor or a platinating agent are outweighed by the therapeutically beneficial effects.

"Treating" or "treatment of" a condition or patient refers to taking steps to obtain beneficial or desired results, including clinical results. For purposes of this invention, beneficial or desired clinical results include, but are not limited to, alleviation, amelioration of one or more symptoms of a cancer; diminishment of extent of disease; delay or slowing of disease progression; amelioration, palliation, or stabilization of the disease state; or other beneficial results. It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors.

"Unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

"Variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al. (1991) Sequences of Immunological Interest, 5$^{th}$ edition, National Institute of Health, Bethesda, MD). The constant domains are not involved directly in the binding of antibody to an antigen, but exhibit various effector functions, such as participation of the antibody in antibody-dependent cellular toxicity.

"Variable region" or "variable domain" of an antibody refers to the amino-terminal domains of the heavy or light chain of the antibody. The variable domains of the heavy chain and light chain may be referred to as "$V_H$" and "W", respectively. These domains are generally the most variable parts of the antibody (relative to other antibodies of the same class) and contain the antigen binding sites.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Abbreviations

Some abbreviations used in the description include:
ADCC: Antibody-dependent cell-mediated cytotoxicity
ATR: Ataxia Telangiectasia and RAD3-related protein
BID: Twice daily
CDR: Complementarity determining region
CRC: Colorectal cancer
CRT: Chemoradiotherapy
CT: Chemotherapy
DNA: Deoxyribonucleic acid
DSB: Double strand break
Ig: Immunoglobulin
IHC: Immunohistochemistry
IV: Intravenous
mCRC: Metastatic colorectal cancer
MSI-H: Microsatellite status instable high
MSI-L: Microsatellite status instable low
MSS: Microsatellite status stable
NK: Natural killers
NSCLC: Non-small-cell lung cancer
OS: Overall survival
PARPi: inhibitor of Poly (ADP-ribose) polymerase (PARP)
PD-1: Programmed death 1
PD-L1: Programmed death ligand 1
PFS: Progression free survival
QD: Once daily
QID: Four times a day
Q2W: Every two weeks
Q3W: Every three weeks
RNA: Ribonucleic acid
RR: Relative risk
RT: Radiotherapy
SCCHN: Squamous cell carcinoma of the head and neck
SCLC: Small-cell lung cancer
SoC: Standard of care
TID: Three times a day
TR: Tumor response
TTP: Time to tumor progression
TTR: Time to tumor recurrence Descriptive Embodiments Without being bound by any theory, the inventors assume that treating tumors with a platinating agent and an ATR inhibitor sensitizes tumors to the treatment with PD-1 antagonist, such as an anti-PD-L1 antibody comprising a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6. Inhibition of the interaction between PD-1 and PD-L1 enhances T-cell responses and mediates clinical antitumor activity. PD-1 is a key immune checkpoint receptor expressed by activated T cells, which mediates immunosuppression and functions primarily in peripheral tissues, where T cells may encounter the immunosuppressive PD-1 ligands PD-L1 (B7-H1) and PD-L2 (B7-DC), which are expressed by tumor cells, stromal cells, or both.

The present invention arose in part from the discovery of a combination benefit for a PD-1 antagonist, a platinating agent and an ATR inhibitor. Surprisingly, the triple combination of the present invention was shown to be superior to the combined treatment with a platinating agent and an ATR inhibitor only. For instance, the triple combination further increased survival in a mouse tumor model. Potentiation may be additive, or it may be synergistic. The potentiating effect of the combination therapy is at least additive. The inventors have shown that the potentiating effect of the combination is synergistic in a mouse model (see, e.g., FIG. 6). Further, initial results indicate that the combination therapy is well tolerated (see FIGS. 4, 7, 10).

Thus, in one aspect, the present invention provides a PD-1 antagonist, a platinating agent and an ATR inhibitor for use in a method for treating a cancer in a subject in need thereof, comprising administering to the subject the PD-1 antagonist, the platinating agent and the ATR inhibitor. Similarly, the present invention provides the use of the combination in a method for treating a cancer in a subject in need thereof, comprising administering to the subject the PD-1 antagonist, the platinating agent and the ATR inhibitor. Similarly, the present invention provides the use of a PD-1 antagonist, a platinating agent and an ATR inhibitor for the manufacture of a medicament for the treatment of cancer in a subject in need thereof, comprising administering to the subject the PD-1 antagonist, the platinating agent and the ATR inhibitor. Likewise, the present invention provides the use of any of these three compounds for the manufacture of a medicament for the treatment of cancer in a subject in need thereof, comprising administering to the subject all three compounds.

It shall be understood that in all embodiments of the invention a therapeutically effective amount of the PD-1 antagonist, the platinating agent and the ATR inhibitor is applied.

In a preferred embodiment, the PD-1 antagonist is an anti-PD-L1 antibody, more preferably an anti-PD-L1 antibody that comprises a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6.

In one embodiment, the anti-PD-L1 antibody is a monoclonal antibody. In one embodiment, the anti-PD-L1 antibody exerts antibody-dependent cell-mediated cytotoxicity (ADCC). In one embodiment, the anti-PD-L1 antibody is a human or humanized antibody. In one embodiment, the anti-PD-L1 antibody is an isolated antibody. In various embodiments, the anti-PD-L1 antibody is characterized by a combination of one or more of the foregoing features, as defined above.

In various embodiments, the anti-PD-L1 antibody is avelumab. Avelumab (formerly designated MSB0010718C) is a fully human monoclonal antibody of the immunoglobulin (Ig) G1 isotype (see e.g., WO 2013/079174). Avelumab selectively binds to PD-L1 and competitively blocks its interaction with PD-1. The mechanisms of action rely on the inhibition of PD-1/PD-L1 interaction and on natural killer (NK)-based antibody-dependent cell-mediated cytotoxicity (ADCC) (see e.g., Boyerinas et al. (2015) Cancer Immunol Res 3: 1148). Compared with anti-PD-1 antibodies that target T cells, avelumab targets tumor cells and therefore, it is expected to have fewer side effects, including a lower risk of autoimmune-related safety issues, as the blockade of PD-L1 leaves the PD-L2/PD-1 pathway intact to promote peripheral self-tolerance (see e.g., Latchman et al. (2001) Nat Immunol 2(3): 261).

Avelumab, its sequence, and many of its properties have been described in WO 2013/079174, where it is designated A09-246-2 having the heavy and light chain sequences according to SEQ ID NOs: 32 and 33, as shown in FIG. 1A (SEQ ID NO: 7) and FIG. 2 (SEQ ID NO: 9), of this patent application. It is frequently observed, however, that in the course of antibody production the C-terminal lysine (K) of the heavy chain is cleaved off. This modification has no influence on the antibody-antigen binding. Therefore, in some embodiments the C-terminal lysine (K) of the heavy chain sequence of avelumab is absent. The heavy chain sequence of avelumab without the C-terminal lysine is shown in FIG. 1B (SEQ ID NO: 8), whereas FIG. 1A (SEQ ID NO: 7) shows the full length heavy chain sequence of avelumab. Further, as shown in WO 2013/079174, one of avelumab's properties is its ability to exert antibody-dependent cell-mediated cytotoxicity (ADCC), thereby directly acting on PD-L1 bearing tumor cells by inducing their lysis without showing any significant toxicity. In a preferred embodiment, the anti-PD-L1 antibody is avelumab, having the heavy and light chain sequences shown in FIG. 1A or 1B (SEQ ID NOs: 7 or 8), and FIG. 2 (SEQ ID NO: 9), or an antigen-binding fragment thereof.

In some aspects, the ATR inhibitor is a compound represented by Formula A-I:

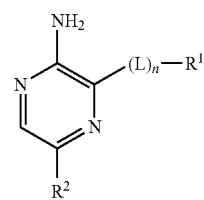

A-I or a pharmaceutically acceptable salt thereof, wherein:

$R^1$ is a 5-6 membered monocyclic aryl or heteroaryl ring having 0-4 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-6 heteroatoms independently selected from the group consisting of nitrogen, oxygen, and sulfur; each $R^1$ is optionally substituted with 1-5 $J^1$ groups;

$R^2$ is a 5-6 membered monocyclic aryl or heteroaryl ring having 0-3 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-4 heteroatoms independently selected from the group consisting of nitrogen, oxygen, and sulfur; each $R^2$ is optionally substituted with 1-5 $J^2$ groups;

L is —C(O)NH— or —C(O)N($C_{1-6}$alkyl)-;

n is 0 or 1;

each $J^1$ and $J^2$ is independently halo, —CN, —$NO_2$, —$V^1$—R, or —$(V^2)_m$-Q;

$V^1$ is a $C_{1-10}$aliphatic chain, wherein 0-3 methylene units are optionally and independently replaced with O, NR", S, C(O), S(O), or S(O)$_2$; $V^1$ is optionally substituted with 1-6 occurrences of $J^{V1}$.

$V^2$ is a $C_{1-10}$aliphatic chain, wherein 0-3 methylene units are optionally and independently replaced with O, NR", S, C(O), S(O), or S(O)$_2$; $V^2$ is optionally substituted with 1-6 occurrences of $J^{V2}$.

m is 0 or 1;

Q is a 3-8 membered saturated or unsaturated monocyclic ring having 0-4 heteroatoms independently selected from the group consisting of nitrogen, oxygen, and sulfur, or a 9-10 membered saturated or unsaturated bicyclic ring having 0-6 heteroatoms independently selected from the group consisting of nitrogen, oxygen, and sulfur; each Q is optionally substituted with 0-5 $J^Q$;

each $J^{V1}$ or $J^{V2}$ is independently halogen, CN, $NH_2$, $NO_2$, $C_{1-4}$aliphatic, NH($C_{1-4}$aliphatic), N($C_{1-4}$aliphatic)$_2$, OH, O($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, NHCO($C_{1-4}$aliphatic), N($C_{1-4}$aliphatic)CO($C_{1-4}$aliphatic), $SO_2$($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;

R is H or $C_{1-6}$aliphatic, wherein said $C_{1-6}$aliphatic is optionally substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2$H, $CO_2$($C_{1-4}$aliphatic), CO($C_{1-4}$aliphatic), O(halo$C_{1-4}$aliphatic), or halo$C_{1-4}$aliphatic;

each $J^Q$ is independently halo, oxo, CN, $NO_2$, X—R, or —(X)$_p$-$Q^4$;

p is 0 or 1;

X is $C_{1-10}$aliphatic, wherein 1-3 methylene units of said $C_{1-6}$aliphatic are optionally replaced with —NR, —O—, —S—, C(O), S(O)$_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, CO($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, SO($C_{1-4}$-aliphatic), $SO_2$($C_{1-4}$aliphatic), $SO_2$NH($C_{1-4}$aliphatic), $SO_2$N($C_{1-4}$-aliphatic)$_2$, NHC(O)($C_{1-4}$aliphatic), N($C_{1-4}$-aliphatic)C(O)($C_{1-4}$-aliphatic), wherein said $C_{1-4}$aliphatic is optionally substituted with 1-3 occurrences of halo;

$Q^4$ is a 3-8 membered saturated or unsaturated monocyclic ring having 0-4 heteroatoms independently selected from the group consisting of nitrogen, oxygen, and sulfur, or a 8-10 membered saturated or unsaturated bicyclic ring having 0-6 heteroatoms independently selected from the group consisting of nitrogen, oxygen, and sulfur; each $Q^4$ is optionally substituted with 1-5 $J^{Q4}$;

$J^{Q4}$ is halo, CN, or $C_{1-4}$alkyl, wherein up to 2 methylene units are optionally replaced with O, NR*, S, C(O), S(O), or S(O)$_2$;

R is H or $C_{1-4}$alkyl, wherein said $C_{1-4}$alkyl is optionally substituted with 1-4 halo;

R" and R* are each independently H, $C_{1-4}$alkyl, or is absent; wherein said $C_{1-4}$alkyl is optionally substituted with 1-4 halo.

In some embodiments, L is —C(O)NH—; and $R^1$ and $R^2$ are phenyl.

In another embodiment, the ATR inhibitor is a compound represented by Formula A-I-a:

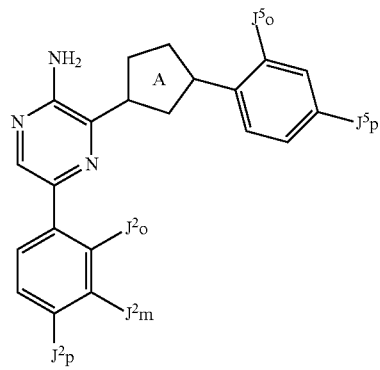

A-I-a or a pharmaceutically salt thereof, wherein:

Ring A

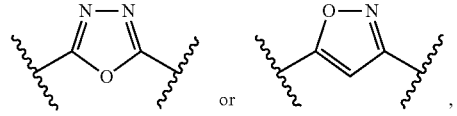 [SMILES: *c1nnc(*)o1 ; *c1cc(*)on1]

$J^5$o is H, F, Cl, $C_{1-4}$aliphatic, O($C_{1-3}$aliphatic), or OH;

$J^5$p is

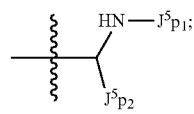

$J^5p_1$ is H, $C_{1-4}$aliphatic, oxetanyl, tetrahydrofuranyl, tetrahydropyranyl; wherein $J^5p_1$ is optionally substituted with 1-2 occurrences of OH or halo;

$J^5p_2$ is H, methyl, ethyl, $CH_2$F, $CF_3$, or $CH_2$OH;

$J^2$o is H, CN, or $SO_2CH_3$;

$J^2$m is H, F, Cl, or methyl;

$J^2$p is —$SO_2$($C_{1-6}$alkyl), —$SO_2$($C_{3-6}$cycloalkyl), —$SO_2$(4-6 membered heterocyclyl), —$SO_2$($C_{1-4}$alkyl)N($C_{1-4}$alkyl)$_2$, or —$SO_2$($C_{1-4}$alkyl)-(4-6 membered heterocyclyl), wherein said heterocyclyl contains 1 heteroatom selected from the group consisting of oxygen, nitrogen, and sulfur; and wherein said $J^2$p is optionally substituted with 1-3 occurrences halo, OH, or O($C_{1-4}$alkyl).

In some embodiments, Ring A is,

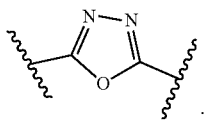 [SMILES: *c1nnc(*)o1]

In other embodiments, Ring A is

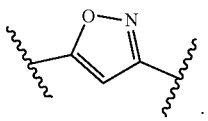

In some preferred embodiments, the ATR inhibitor is a compound represented by the following formula (Compound 1):

Compound 1

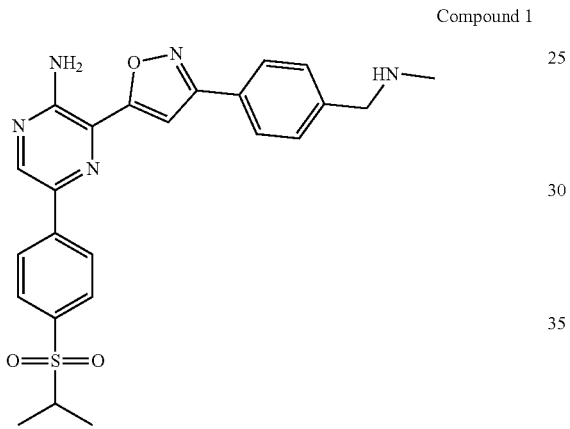

or a pharmaceutically acceptable salt thereof. Compound 1 is also referred to as 3-[3-(4-Methylaminomethyl-phenyl)-isoxazol-5-yl]-5-[4-(propane-2-sulfonyl)-phenyl]-pyrazin-2-ylamine.

In another aspect, the ATR inhibitor is represented by Formula A-II:

A-II

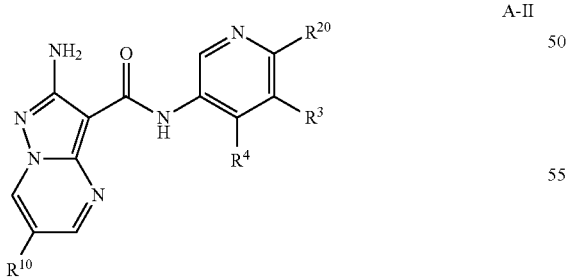

or a pharmaceutically salt or derivative thereof,
wherein:
$R^{10}$ is selected from fluoro, chloro, or —C(J$^{10}$)$_2$CN;
$J^{10}$ is independently H or C$_{1-2}$alkyl; or
two occurrences of J$^1$, together with the carbon atom to which they are attached, form a 3-4 membered optionally substituted carbocyclic ring;

$R^{20}$ is H, halo, —CN, NH$_2$, a C$_{1-2}$alkyl optionally substituted with 0-3 occurrences of fluoro; or a C$_{1-3}$aliphatic chain, wherein up to two methylene units of the aliphatic chain are optionally replaced with —O—, —NR$^a$—, —C(O)—, or —S(O)$_z$—;

$R^3$ is H, halo, C$_{1-4}$alkyl optionally substituted with 1-3 occurrences of halo, C$_{3-4}$cycloalkyl, —CN, or a C$_{1-3}$aliphatic chain, wherein up to two methylene units of the aliphatic chain are optionally replaced with —O—, —NR$^a$—, —C(O)—, or —S(O)$_z$—;

$R^4$ is Q$^1$ or a C$_{1-10}$aliphatic chain, wherein up to four methylene units of the aliphatic chain are optionally replaced with —O—, —NR$^a$—, —C(O)—, or —S(O)$_z$—; each R$^4$ is optionally substituted with 0-5 occurrences of J$^{Q1}$; or $R^3$ and $R^4$, taken together with the atoms to which they are bound, form a 5-6 membered aromatic or non-aromatic ring having 0-2 heteroatoms selected from the group consisting of oxygen, nitrogen, and sulfur; the ring formed by R$^3$ and R$^4$ is optionally substituted with 0-3 occurrences of J$^Z$;

$Q^1$ is a 3-7 membered fully saturated, partially unsaturated, or aromatic monocyclic ring, the 3-7 membered ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^Z$ is independently C$_{1-6}$aliphatic, =O, halo, or →O;

$J^{Q1}$ is independently -CN, halo, =O, Q$^2$, or a C$_{1-8}$aliphatic chain, wherein up to three methylene units of the aliphatic chain are optionally replaced with —O—, —NR$^a$—, —C(O)—, or —S(O)$_z$—; each occurrence of J$^{Q1}$ is optionally substituted by 0-3 occurrences of J$^R$; or two occurrences of J$^{Q1}$ on the same atom, taken together with the atom to which they are joined, form a 3-6 membered ring having 0-2 heteroatoms selected from the group consisting of oxygen, nitrogen, and sulfur; wherein the ring formed by two occurrences of J$^{Q1}$ is optionally substituted with 0-3 occurrences of J$^X$; or two occurrences of J$^{Q1}$, together with Q$^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently —CN, halo, =O, →O; Q$^3$, or a C$_{1-6}$aliphatic chain, wherein up to three methylene units of the aliphatic chain are optionally replaced with —O—, —NR$^a$—, —C(O)—, or —S(O)$_z$—; each J$^R$ is optionally substituted with 0-3 occurrences of J$^T$; or two occurrences of J$^R$ on the same atom, together with the atom to which they are joined, form a 3-6 membered ring having 0-2 heteroatoms selected from oxygen, nitrogen, or sulfur; wherein the ring formed by two occurrences of J$^R$ is optionally substituted with 0-3 occurrences of J$^X$; or two occurrences of J$^R$, together with Q$^2$, form a 6-10 membered saturated or partially unsaturated bridged ring system;

Q³ is a 3-7 membered fully saturated, partially unsaturated, or aromatic monocyclic ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^X$ is independently —CN, =O, halo, or a $C_{1-4}$aliphatic chain, wherein up to two methylene units of the aliphatic chain are optionally replaced with —O—, —NR$^a$—, —C(O)—, or —S(O)$_z$—;

$J^T$ is independently halo, —CN, →O; =O, —OH, a $C_{1-6}$aliphatic chain, wherein up to two methylene units of the aliphatic chain are optionally replaced with —O—, —NR$^a$—, —C(O)—, or —S(O)$_z$—; or a 3-6 membered non-aromatic ring having 0-2 heteroatoms selected from the group consisting of oxygen, nitrogen, and sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from the group consisting of oxygen, nitrogen, and sulfur; or two occurrences of $J^T$, together with Q³, form a 6-10 membered saturated or partially unsaturated bridged ring system;

$J^M$ is independently halo or $C_{1-6}$aliphatic;

z is 0, 1 or 2; and

R$^a$ is independently H or Cl-aliphatic.

In some embodiments, R$^{10}$ and R³ are fluoro.

In other embodiments, R⁴ is Q¹.

In still other embodiments, Q¹ is independently piperidinyl and imidazolyl.

In another embodiment, the ATR inhibitor is represented by Formula A-II-a:

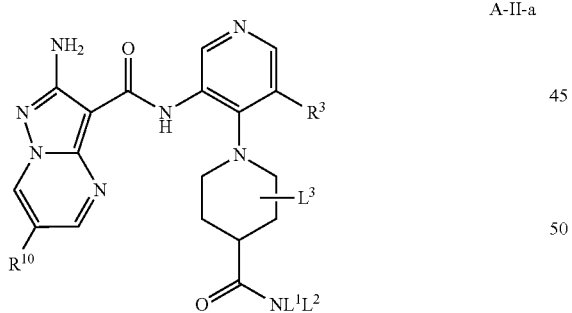

A-II-a or a pharmaceutically acceptable salt or prodrug thereof, wherein:

R$^{10}$ is fluoro, chloro, or —C(J$^{10}$)$_2$CN;

J$^{10}$ is independently H or $C_{1-2}$alkyl; or two occurrences of J$^{10}$, together with the carbon atom to which they are attached, form an optionally substituted 3-4 membered carbocyclic ring;

R³ is H; chloro; fluoro; $C_{1-4}$alkyl optionally substituted with 1-3 occurrences of halo; $C_{3-4}$cycloalkyl; —CN; or a $C_{1-3}$aliphatic chain, wherein up to two methylene units of the aliphatic chain are optionally replaced with —O—, —NR$^a$—, —C(O)—, or —S(O)$_z$;

L¹ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —NR$^a$—, —C(O)—, or —S(O)$_z$; each L¹ is optionally substituted with $C_1$ aliphatic; —CN; halo; —OH; or a 3-6 membered non-aromatic ring having 0-2 heteroatoms selected from the group consisting of oxygen, nitrogen, and sulfur;

L² is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —NR$^a$—, —C(O)—, or —S(O)Z; each L² is optionally substituted with $C_{1-4}$aliphatic; —CN; halo; —OH; or a 3-6 membered non-aromatic ring having 0-2 heteroatoms selected from the group consisting of oxygen, nitrogen, and sulfur; or L¹ and L², together with the nitrogen to which they are attached, form a Ring D; Ring D is optionally substituted with 0-5 occurrences of $J^G$ L³ is H, $C_{1-3}$aliphatic, or CN;

Ring D is a 3-7 membered heterocyclyl ring having 1-2 heteroatoms selected from the group consisting of oxygen, nitrogen, and sulfur; or an 7-12 membered fully saturated or partially unsaturated bicyclic ring having 1-5 heteroatoms selected from the group consisting of oxygen, nitrogen, and sulfur;

$J^G$ is independently halo; —CN; —N(R°)$_2$; →O; a 3-6 membered carbocycyl; a 3-6 membered heterocyclyl having 1-2 heteroatoms selected from the group consisting of oxygen, nitrogen, and sulfur; or a $C_{1-4}$alkyl chain, wherein up to two methylene units of the alkyl chain are optionally replaced with —O—, —NR$^a$—, —C(O)—, or —S(O)$_z$; each $J^G$ is optionally substituted with 0-2 occurrences of $J^K$;

two occurrences of $J^G$ on the same atom, together with the atom to which they are joined, form a 3-6 membered ring having 0-2 heteroatoms selected from the group consisting of oxygen, nitrogen, and sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from the group consisting of oxygen, nitrogen, and sulfur;

z is 0, 1, or 2; and

R$^a$ and R° are independently H or $C_{1-4}$alkyl.

In another embodiment, R$^{10}$ and R³ are fluoro.

In other preferred embodiments, the ATR inhibitor is a compound represented by the following formula (Compound 2):

Compound 2

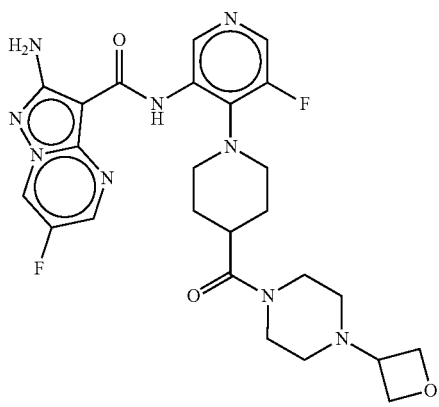

or a pharmaceutically acceptable salt thereof. Compound 2 is also referred to as 2-amino-6-fluoro-N-(5-fluoro-4-{4-[4-(oxetan-3-yl)piperazine-1-carbonyl]piperidin-1-yl}pyridin-3-yl)pyrazolo[1,5-a]pyrimidine-3-carboxamide.

In some preferred embodiments, the ATR inhibitor is a compound represented by the following formula (Compound 3):

Compound 3

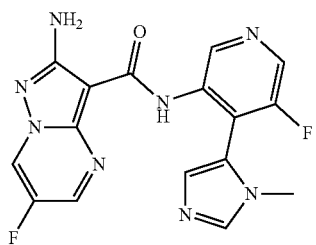

or a pharmaceutically acceptable salt thereof. Compound 3 is also referred to as 2-Amino-6-fluoro-N-[5-fluoro-4-(1-methyl-1H-imidazol-5-yl)pyridin-3-yl]pyrazolo[1,5-a]pyrimidine-3-carboxamide.

Another preferred ATR inhibitor is AZD6738, which is also known as ceralasertib (CAS Registry Number 1352226-88-0), or a pharmaceutically acceptable salt thereof. It has the chemical formula 4-{4-[(3R)-3-methylmorpholin-4-yl]-6-[1-(S-methylsulfonimidoyl)cyclopropyl]pyrimidin-2-yl}-1H-pyrrolo[2,3-b]pyridine and is represented by the following formula (Compound 4):

Compound 4

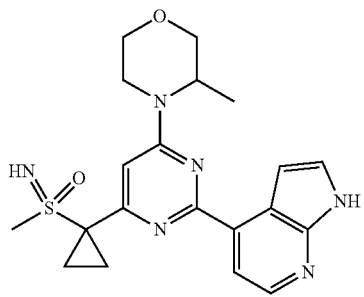

or a pharmaceutically acceptable salt thereof.

Another preferred ATR inhibitor has the chemical formula 2-[(3R)-3-methylmorpholin-4-yl]-4-(1-methyl-1H-pyrazol-5-yl)-8-(1H-pyrazol-5-yl)-1,7-naphthyridine and is represented by the following formula (Compound 5):

Compound 5

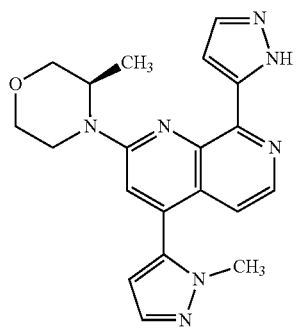

or a pharmaceutically acceptable salt thereof.

In some embodiments, the ATR inhibitor is selected from the following group:

Compound 6

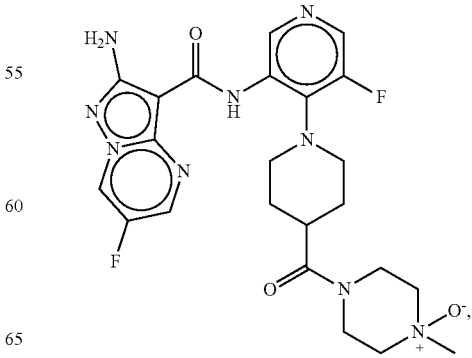

Compound 7

Compound 8

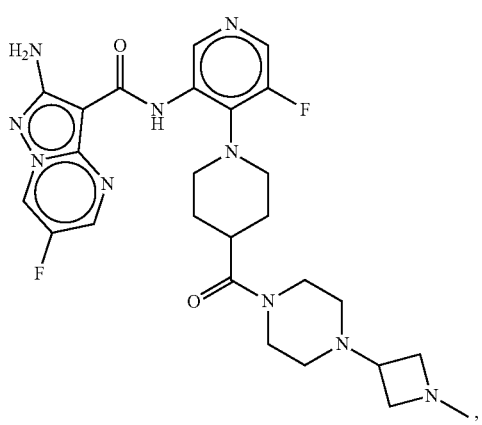

or a pharmaceutically acceptable salt thereof.

In yet another embodiment, the compound is an ATR inhibitor selected from a compound described in WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO 2014/143242, WO 2014/143241, WO 2015/084384, WO 2014/143240, WO 2015/187451, WO 2015/085132, WO 2014/062604, WO 2014/143240, WO 2013/071094, WO 2013/071093, WO 2013/071090, WO 2013/071088, WO 2013/049859, WO 2013/049719, WO 2013/049720, WO 2013/049722, WO 2012/138,938, WO 2011/163527, WO 2011/143,423, WO 2011/143,426, WO 2011/143,399, and/or WO 2010/054398.

In one aspect, the platinating agent is selected from cisplatin, carboplatin, oxaliplatin, nedaplatin, lobaplatin, triplatin, tetranitrate, heptaplatin, picoplatin, ProLindac (CAS number 674289-90-8), Lipoplatin (liposomally encapsulated form of cisplatin), aroplatin and satraplatin. Preferably, the platinating agent is carboplatin.

In one embodiment, the therapeutic combination of the invention is used in the treatment of a human subject. The main expected benefit in the treatment with the therapeutic combination is a gain in risk/benefit ratio for these human patients.

In one embodiment, the cancer is identified as a PD-L1 positive cancerous disease. Pharmacodynamic analyses show that tumor expression of PD-L1 might be predictive of treatment efficacy. According to the invention, the cancer is preferably considered to be PD-L1 positive if between at least 0.1% and at least 10% of the cells of the cancer have PD-L1 present at their cell surface, more preferably between at least 0.5% and 5%, most preferably at least 1%. In one embodiment, the PD-L1 expression is determined by immunohistochemistry (IHC). Immunohistochemistry with anti-PD-L1 primary antibodies can be performed on serial cuts of formalin fixed and paraffin embedded specimens from patients treated with an PD-1 antagonist, such as avelumab, an ATR inhibitor and a platinating agent.

In another embodiment, the cancer is selected from cancer of the lung, head and neck, colon, urothelium, prostate, esophagus, bladder, stomach, neuroendocrine system, mesenchyme, breast, ovarian, primary peritoneal, fallopian tube, pancreas and histological subtypes thereof (e.g., adeno, squamous, large cell). In some embodiments, the cancer is selected from small-cell lung cancer (SCLC), non-small-cell lung cancer (NSCLC), squamous cell carcinoma of the head and neck (SCCHN), colorectal cancer (CRC), primary neuroendocrine tumors and sarcoma. In a preferred embodiment, the cancer is selected from ovarian cancer, primary peritoneal cancer, fallopian tube cancer, in particular, those that are a PARPi-resistant recurrent cancer.

In various embodiments, the therapeutic combination of the invention is employed as a first, second, third or later line of treatment. A line of treatment refers to a place in the order of treatment with different medications or other therapies received by a patient. First-line therapy regimens are treatments given first, whereas second- or third-line therapy is given after the first-line therapy or after the second-line therapy, respectively. Therefore, first-line therapy is the first treatment for a disease or condition. In patients with cancer, first-line therapy, sometimes referred to as primary therapy or primary treatment, can be surgery, chemotherapy, radiation therapy, or a combination of these therapies. Typically, a patient is given a subsequent chemotherapy regimen (second- or third-line therapy), either because the patient did not show a positive clinical outcome or only showed a sub-clinical response to a first- or second-line therapy or showed a positive clinical response but later experienced a relapse, sometimes with disease now resistant to the earlier therapy that elicited the earlier positive response.

If the safety and the clinical benefit offered by the therapeutic combination of the invention are confirmed, this combination of a PD-1 antagonist, an ATR inhibitor and a platinating agent warrants a first-line setting in cancer patients. Particularly, the combination may become a new standard treatment for patients suffering from a cancer that is selected from the group of SCLC extensive disease (ED), NSCLC, SCCHN, ovarian cancer, primary peritoneal cancer and fallopian tube cancer.

As the mode of action differs between ATR inhibitors, platinating agents and PD-1 antagonists, the chances to have enhanced immune-related adverse events is low. The absence of overlapping immune features in nonclinical findings or in published clinical results makes the risk low for the combination therapy of the invention to show enhanced adverse events above what is generally observed in these agents when administered alone. The identified and potential risks for the PD-1 antagonist of the invention, preferably avelumab, the ATR inhibitor, preferably Compound 1 or 2, and the platinating agent of the invention, preferably carboplatin, in each case as single agent, are considered to represent the potential risks for the combination treatment as well.

It is preferred that the therapeutic combination of the invention is applied in a later line of treatment, particularly a second-line or higher treatment of the cancer. There is no limitation to the prior number of therapies provided that the subject underwent at least one round of prior cancer therapy. The round of prior cancer therapy refers to a defined schedule/phase for treating a subject with, e.g., one or more chemotherapeutic agents, radiotherapy or chemoradiotherapy, and the subject failed with such previous treatment, which was either completed or terminated ahead of schedule. One reason could be that the cancer was resistant or became resistant to prior therapy. The current standard of care (SoC) for treating cancer patients often involves the administration of toxic and old chemotherapy regimens. The SoC is associated with high risks of strong adverse events that are likely to interfere with the quality of life (such as secondary cancers). In one embodiment, the combination of a PD-1 antagonist, an ATR inhibitor and a platinating agent may be as effective and better tolerated than SoC chemotherapy in patients with cancer resistant to mono- and/or poly-chemotherapy, radiotherapy or chemoradiotherapy.

In a preferred embodiment, the PD-1 antagonist, ATR inhibitor and platinating agent are administered in a second-line or higher treatment, more preferably a second-line treatment, of a cancer. In some embodiments, the patient has relapsed or progressed after being administered a PARPi-based therapy but before being administered any medicament of the combination of the invention. In some embodiments, the patient previously underwent at least one PARPi-based therapy cycle. In some embodiments, the patient previously underwent at least two, three, four, five or six PARPi-based therapy cycles. In some embodiments, the PARPi-based therapy was stopped after at least one cycle because the disease progressed despite the PARPi-based therapy. In some embodiments, the PARPi-based therapy was stopped after at least one cycle due to toxicity, wherein the toxicity is associated with the PARPi-based therapy. In some embodiments, the PARPi-based therapy was stopped after at least one cycle due to a resistance of the patient to the PARPi-based therapy. In a more preferred embodiment, the PD-1 antagonist, ATR inhibitor and platinating agent are administered in a second-line or higher treatment of the cancer selected from the group of PARPi-resistant recurrent ovarian cancer, PARPi-resistant recurrent fallopian tube cancer, PARPi-resistant recurrent primary peritoneal cancer, pre-treated relapsing metastatic NSCLC, unresectable locally advanced NSCLC, pre-treated SCLC ED, SCLC unsuitable for systemic treatment, pre-treated relapsing (recurrent) or metastatic SCCHN, recurrent SCCHN eligible for re-irradiation, and pre-treated microsatellite status instable low (MSI-L) or microsatellite status stable (MSS) metastatic colorectal cancer (mCRC). SCLC and SCCHN are particularly systemically pre-treated. MSI-L/MSS mCRC occurs in 85% of all mCRC.

In some embodiments that employ an anti-PD-1 or anti-PD-L1 antibody, preferably avelumab, in the combination therapy, the dosing regimen will comprise administering the antibody at a dose of about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/kg at intervals of about 14 days (±2 days) or about 21 days (±2 days) or about 30 days (±2 days) throughout the course of treatment. In other embodiments that employ an anti-PD-1 or anti-PD-L1 antibody, preferably avelumab, in the combination therapy, the dosing regimen will comprise administering the antibody at a dose of from about 0.005 mg/kg to about 20 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose. In certain embodiments, a subject will be administered an intravenous (IV) infusion of a medicament comprising the anti-PD-1 or anti-PD-L1 antibody, preferably avelumab. In some embodiments, the PD-1 antagonist that is employed in the combination therapy is the anti-PD-L1 antibody avelumab, which is administered intravenously at a dose selected from the group consisting of: about 1 mg/kg Q2W (Q2W=one dose every two weeks), about 2 mg/kg Q2W, about 3 mg/kg Q2W, about 5 mg/kg Q2W, about 10 mg/kg Q2W, about 1 mg/kg Q3W (Q3W=one dose every three weeks), about 2 mg/kg Q3W, about 3 mg/kg Q3W, about 5 mg/kg Q3W, about 10 mg/kg Q3W and about 20 mg/kg Q3W. In some embodiments, the PD-1 antagonist in the combination therapy is the anti-PD-L1 antibody avelumab, which is administered in a liquid medicament at a dose selected from the group consisting of about 1 mg/kg Q2W, about 2 mg/kg Q2W, about 3 mg/kg Q2W, about 5 mg/kg Q2W, about 10 mg/kg Q2W, about 1 mg/kg Q3W, about 2 mg/kg Q3W, about 3 mg/kg Q3W, about 5 mg/kg Q3W, about 10 mg/kg Q3W and about 20 mg/kg Q3W. In some embodiments, a treatment cycle begins with the first day of combination treatment and last for 2 weeks. In such embodiments, the combination therapy is preferably administered for at least 12 weeks (6 cycles of treatment), more preferably at least 24 weeks, and even more preferably at least 2 weeks after the patient achieves a CR.

In some embodiments that employ an anti-PD-1 or anti-PD-L1 antibody, preferably avelumab, in the combination therapy, the dosing regimen will comprise administering the antibody at a dose of about 400-800 mg flat dose Q2W. Preferably, the flat dosing regimen is 400 mg, 450 mg, 500 mg, 550 mg, 600 mg, 650 mg, 700 mg, 750 mg or 800 mg flat dose Q2W. More preferably, the flat dosing regimen is 800 mg flat dose Q2W. In some more preferred embodiments that employ an anti-PD-1 or anti-PD-L1 antibody, preferably avelumab, in the combination therapy, the dosing regimen will be a fixed dose of 800 mg given intravenously at intervals of about 14 days (±2 days).

In some embodiments that employ an anti-PD-1 or anti-PD-L1 antibody, preferably avelumab, in the combination therapy, the dosing regimen will comprise administering the antibody at a dose of about 800-1600 mg flat dose Q3W. Preferably, the flat dosing regimen is 800 mg, 900 mg, 1000 mg, 1100 mg, 1200 mg, 1300 mg, 1400 mg, 1500 mg or 1600 mg flat dose Q3W. More preferably, the flat dosing regimen is 1600 mg flat dose Q3W. In some more preferred embodiments that employ an anti-PD-1 or anti-PD-L1 antibody, preferably avelumab, in the combination therapy, the dosing regimen will be a fixed dose of 1600 mg given intravenously at intervals of about 21 days (±2 days).

In another embodiment, the anti-PD-1 or anti-PD-L1 antibody, preferably avelumab, will be given IV every two weeks (Q2W). In certain embodiments, the anti-PD-L1 antibody is administered intravenously for 50-80 minutes at a dose of about 10 mg/kg body weight every two weeks (Q2W). In a more preferred embodiment, the avelumab dose will be 10 mg/kg body weight administered as 1-hour intravenous infusions every two weeks (Q2W). In certain embodiments, the anti-PD-L1 antibody is administered intravenously for 50-80 minutes at a fixed dose of about 800 mg every two weeks (Q2W). In a more preferred embodiment, the avelumab dose will be 800 mg administered as 1-hour intravenous infusions every 2 weeks (Q2W). Given the variability of infusion pumps from site to site, a time window of minus 10 minutes and plus 20 minutes is permitted.

Pharmacokinetic studies demonstrated that the 10 mg/kg dose of avelumab achieves excellent receptor occupancy with a predictable pharmacokinetics profile (see e.g., Heery et al. (2015) Proc 2015 ASCO Annual Meeting, abstract 3055). This dose is well tolerated, and signs of antitumor activity, including durable responses, have been observed. Avelumab may be administered up to 3 days before or after the scheduled day of administration of each cycle due to administrative reasons. Pharmacokinetic simulations also suggested that exposures to avelumab across the available range of body weights are less variable with 800 mg Q2W compared with 10 mg/kg Q2W. Exposures were similar near the population median weight. Low-weight subjects tended towards marginally lower exposures relative to the rest of the population when weight-based dosing was used, and marginally higher exposures when flat dosing was applied. The implications of these exposure differences are not expected to be clinically meaningful at any weight across the whole population. Furthermore, the 800 mg Q2W dosing regimen is expected to result in Ctrough>1 mg/mL required to maintain avelumab serum concentrations at >95% TO throughout the entire Q2W dosing interval in all weight categories. In a preferred embodiment, a fixed dosing regimen of 800 mg administered as a 1 hour IV infusion Q2W will be utilized for avelumab.

In some embodiments, the ATR inhibitor is administered intravenously or orally. In some embodiments, the ATR inhibitor is administered by continuous infusion. Compound 1, or a pharmaceutically acceptable salt thereof, is preferably administered intravenously. Compound 2, or a pharmaceutically acceptable salt thereof, Compound 3, or a pharmaceutically acceptable salt thereof, and Compound 4, or a pharmaceutically acceptable salt thereof, are preferably administered orally. In some embodiments, the ATR inhibitor that is employed in the combination therapy may be administered at a dose of between about 20 mg/m$^2$ and about 300 mg/m$^2$, between about 30 mg/m$^2$ and about 240 mg/m$^2$, between about 40 mg/m$^2$ and about 240 mg/m$^2$, between about 40 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, or between about 80 mg/m$^2$ and about 100 mg/m$^2$. In certain embodiments, the ATR inhibitor may be administered at a dose between about 40 mg/m$^2$ and about 300 mg/m$^2$ (e.g., about 240 mg/m$^2$).

In some instances, the ATR inhibitor may be administered at a dose between about 60 mg/m$^2$ and about 180 mg/m$^2$ (e.g., 120 mg/m$^2$). In certain cases, the ATR inhibitor may be administered at a dose between about 80 mg/m$^2$ and about 100 mg/m$^2$ (e.g., about 90 mg/m$^2$). In some embodiments, the ATR inhibitor may be administered at a dose of about 40 mg/m$^2$, about 60 mg/m$^2$, about 90 mg/m$^2$ or about 120 mg/m$^2$. Preferably, the ATR inhibitor of the therapeutic combination is administered at a dose of about 90 mg/m$^2$.

In some embodiments, the ATR inhibitor is Compound 1, or a pharmaceutically acceptable salt thereof, and administered at a dose of between about 20 mg/m$^2$ and about 300 mg/m$^2$, between about 30 mg/m$^2$ and about 240 mg/m$^2$, between about 40 mg/m$^2$ and about 240 mg/m$^2$, between about 40 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, or between about 80 mg/m$^2$ and about 100 mg/m$^2$. In some embodiments, Compound 1, or a pharmaceutically acceptable salt thereof, is administered at a dose of about 40 mg/m$^2$, about 60 mg/m$^2$, about 90 mg/m$^2$ or about 120 mg/m$^2$, preferably at a dosage of about 90 mg/m$^2$. In some embodiments, the platinating agent that is employed in the combination therapy, as described herein, is administered intravenously. In some embodiments, the platinating agent may be administered at a target AUC of between about 3 mg/mL·min and about 7 mg/mL·min, between about 3.5 mg/mL·min and about 6 mg/mL·min, between about 4 mg/mL·min and about 6 mg/mL·min, between about 4 mg/mL·min and about 5.5 mg/mL·min, or between about 4 mg/mL·min and about 5 mg/mL·min. In some embodiments, the platinating agent may be administered at a target AUC of between about 3 mg/mL·min and about 6 mg/mL·min. In certain embodiments, the platinating agent may be administered with a target AUC of between about 4 mg/mL·min and about 5 mg/mL·min. In certain embodiments, the platinating agent may be administered with a target AUC of about 5 mg/mL·min. As used herein, the term "target AUG" refers the target area under the plasma concentration versus time curve. The term "AUC" refers the area under the plasma concentration versus time curve. The dosage of certain platinating agents, such as carboplatin, may be determined from the drug label information. For example, the dosage in mg of carboplatin may be determined from the target AUC based on mathematical formula, which is based on a patient's pre-existing renal function or renal function and desired platelet nadir. The Calvert formula, shown below, is used to calculate dosage in milligrams, based upon a patient's glomerular filtration rate (GFR in mL/min) and carboplatin target area under the concentration versus time curve (AUC in mg/mL·min). GFR may be measured using 51Cr-EDTA clearance or may be estimated using methods known to ordinary skill in the art.

Total Dose (mg)=(target AUC)×(GFR+25)

In some embodiment, carboplatin is administered intravenously at a target AUC of between about 3 mg/mL·min and about 7 mg/mL·min, between about 3.5 mg/mL·min and about 6 mg/mL·min, or between about 4 mg/mL·min and about 5 mg/mL·min. In some embodiments, carboplatin is intravenously administered once every three weeks at a target AUC of about 5 mg/mL·min.

In certain embodiments, cisplatin is administered intravenously. In some embodiments, cisplatin is administered via intravenous infusion over about 1 hour. In certain embodiments, cisplatin is administered intravenously in an amount of about 30 and about 90 mg/m$^2$, of about 40 and about 75 mg/m$^2$, or of about 60 and about 90 mg/m$^2$. In some specific embodiments, the dosage of cisplatin is at 40 mg/m$^2$, 60 mg/m$^2$, or 75 mg/m$^2$. Preferably, cisplatin is administered at 75 mg/m$^2$. In certain embodiments, cisplatin is administered via intravenous infusion at about 75 mg/m$^2$ over a 60-minute period. In some embodiments, cisplatin is administered once every three weeks (Q3W), in an amount of about at 75 mg/m$^2$.

It should be understood that all combinations of the above-referenced ranges for dosage of the PD-1 antagonist, the ATR inhibitor and the platinating agent for use in a combination therapy, as described herein, may be possible. In addition, the dosing of the three compounds employed in the combination therapy can be adapted to one another to improve convenience and compliance.

For instance, in some embodiments, the platinating agent, preferably carboplatin, is administered with a target AUC of between about 3 mg/mL·min and about 6 mg/mL·min (e.g., between about 4 mg/mL·min and about 6 mg/mL·min, between about 4 mg/mL·min and about 5 mg/mL·min or about 5 mg/mL·min), the ATR inhibitor, preferably Compound 1, or a pharmaceutically acceptable salt thereof, is administered with a dosage between about 20 mg/m$^2$ and about 300 mg/m$^2$ (e.g., between about 40 mg/m$^2$ and about 180 mg/m$^2$, between about 60 mg/m$^2$ and about 100 mg/m$^2$, between about 80 mg/m$^2$ and about 100 mg/m$^2$, about 40 mg/m$^2$, about 60 mg/m$^2$ or about 90 mg/m$^2$) and the PD-1 antagonist, preferably avelumab, is administered with a dosage between about 400 mg and about 3200 mg (e.g., between about 600 mg and about 2500 mg, between about 800 mg and about 2000 mg, between about 1500 mg and about 1700 mg, about 800 mg or about 1600 mg).

In some embodiments, the combination therapy employs avelumab administered with a dosage of about 1600 mg, carboplatin administered at a dosage with a target AUC of about 5 mg/mL·min and Compound 1, or a pharmaceutically acceptable salt thereof, administered at a dosage of about 90 mg/m². In some embodiments, the combination therapy employs avelumab administered Q3W with a dosage of about 1600 mg, carboplatin administered Q3W at a dosage with a target AUC of about 5 mg/mL·min and Compound 1, or a pharmaceutically acceptable salt thereof, administered Q3W at a dosage of about 90 mg/m². In some embodiments, avelumab at a dosage of about 1600 mg, carboplatin at a dosage with a target AUC of about 5 mg/mL·min and Compound 1, or a pharmaceutically acceptable salt thereof, at a dosage of about 90 mg/m² are all administered on day 1 of each Q3W cycle.

In some embodiments, the combination regimen comprises a lead phase, optionally followed by a maintenance phase after completion of the lead phase. As used herein, the combination treatment comprises a defined period of treatment (i.e., a first phase or lead phase). After completion of such a period or phase, another defined period of treatment may follow (i.e., a second phase or maintenance phase).

In certain embodiments, the lead phase comprises the combination treatment with the PD-1 antagonist, the ATR inhibitor and the platinating agent, whereas the maintenance phase comprises a monotherapy with the PD-1 antagonist, more preferably avelumab monotherapy.

In some embodiments, the lead phase of, for instance, up to six cycles may comprise avelumab administered Q3W with a dosage of about 1600 mg, carboplatin administered Q3W at a dosage with a target AUC of about 5 mg/mL·min and Compound 1, or a pharmaceutically acceptable salt thereof, administered Q3W at a dosage of about 90 mg/m², followed by a maintenance phase comprising the administration of 800 mg avelumab Q2W.

In some embodiments, avelumab, carboplatin and Compound 1, or a pharmaceutically acceptable salt thereof, are used in the treatment of ovarian, fallopian tube or primary peritoneal cancer, preferably a PARPi-resistant recurrent form thereof, wherein the lead phase of, for instance, up to six cycles may comprise avelumab administered Q3W with a dosage of about 1600 mg, carboplatin administered Q3W at a dosage with a target AUC of about 5 mg/mL·min and Compound 1, or a pharmaceutically acceptable salt thereof, administered Q3W at a dosage of about 90 mg/m², followed by a maintenance phase comprising the administration of 800 mg avelumab Q2W.

The PD-1 antagonist, the ATR inhibitor and the platinating agent may be administered in any order. For instance, all may be administered substantially simultaneously or sequentially. Also, two of them may be administered substantially simultaneously, followed by the sequential administration of the third. The PD-1 antagonist, the ATR inhibitor and the platinating agent are administered to the patient in any order in separate compositions, formulations or unit dosage forms, or two or all three compounds are administered together in one composition, formulation or unit dosage form. It will be appreciated that the PD-1 antagonist, the ATR inhibitor and the platinating agent are administered on the same day or on different days and in any order as according to an appropriate dosing protocol. In some embodiments, the three compounds are separately administered on three consecutive days of each treatment cycle. For instance, the combination is administered Q3W with the PD-1 antagonist being administered on day 1, the ATR inhibitor being administered on day 2 and the platinating agent being administered on day 3.

In some embodiments, the combination regimen comprises the steps of: (a) under the direction or control of a physician, the subject receiving the PD-1 antagonist prior to first receipt of the ATR inhibitor and the platinating agent; and (b) under the direction or control of a physician, the subject receiving the ATR inhibitor and the platinating agent.

In some embodiments, the combination regimen comprises the steps of: (a) prescribing the subject to self-administer the PD-1 antagonist; and (b) administering the ATR inhibitor and the platinating agent to the subject.

In some embodiments, the combination regimen comprises, after the subject has received the PD-1 antagonist prior to the first administration of the ATR inhibitor and the platinating agent, administering the ATR inhibitor and the platinating agent to the subject.

In some embodiments, the combination regimen comprises the steps of: (a) under the direction or control of a physician, the subject receiving the PD-1 antagonist and the platinating agent prior to first receipt of the ATR inhibitor; and (b) under the direction or control of a physician, the subject receiving the ATR inhibitor.

In some embodiments, the combination regimen comprises the steps of: (a) prescribing the subject to self-administer the ATR inhibitor; and (b) administering the PD-1 antagonist and the platinating agent to the subject.

In some embodiments, the combination regimen comprises, after the subject has received the ATR inhibitor prior to the first administration of the PD-1 antagonist and the platinating agent, administering the PD-1 antagonist and the platinating agent to the subject.

In some embodiments, the combination regimen comprises the steps of: (a) under the direction or control of a physician, the subject receiving the ATR inhibitor prior to first receipt of the PD-1 antagonist and the platinating agent; and (b) under the direction or control of a physician, the subject receiving the PD-1 antagonist and the platinating agent.

In some embodiments, the combination regimen comprises the steps of: (a) administering the PD-1 antagonist and the platinating agent to the subject; and (b) prescribing the subject to self-administer the ATR inhibitor.

In some embodiments, the combination regimen comprises, after the subject has received the PD-1 antagonist and the platinating agent prior to the first administration of the ATR inhibitor, administering the ATR inhibitor to the subject.

Concurrent treatment considered necessary for the patient's well-being may be given at discretion of the treating physician. In some embodiments, the PD-1 antagonist, ATR inhibitor and platinating agent are administered in combination with (further) chemotherapy (CT), radiotherapy (RT), or chemotherapy and radiotherapy (CRT). In certain embodiments, the chemotherapeutic agent is selected from the group of doxorubicin, fluorouracil, an anthracycline, and a combination thereof.

In certain embodiments, the patient further obtains radiation therapy. In certain embodiments, the radiotherapy comprises about 35-70 Gy/20-35 fractions. In some embodiments, the radiotherapy is given either with standard fractionation (1.8 to 2 Gy for day 5 days a week) up to a total dose of 50-70 Gy in once daily. In one embodiment, stereotactic radiotherapy as well as the gamma knife are used. In the palliative setting, other fractionation schedules are also widely used for example 25 Gy in 5 fractions or 30 Gy in 10 fractions. For radiotherapy, the duration of treatment will be the time frame when radiotherapy is given. These interventions apply to treatment given with electrons, photons and protons, alfa-emitters or other ions, treatment with radio-nucleotides, for example, treatment with $^{131}$I given to patients with thyroid cancer, as well in patients treated with boron capture neutron therapy.

The PD-1 antagonist, ATR inhibitor, platinating agent and additional chemotherapeutic according to methods of the present invention, are administered using any amount and any route of administration effective for treating or decreasing the severity of a disorder provided above. The exact amount required will vary from subject to subject, depending on the species, age, and general condition of the subject, the severity of the infection, the particular agent, its mode of administration, and the like.

Also provided herein is a PD-1 antagonist, a platinating agent and an ATR inhibitor for use as a medicament.

Also provided is a combination comprising a PD-1 antagonist, a platinating agent and an ATR inhibitor. Also provided is a combination comprising a PD-1 antagonist, a platinating agent and an ATR inhibitor for use as a medicament. Also provided is a combination comprising a PD-1 antagonist, a platinating agent and an ATR inhibitor for use in the treatment of cancer.

In still another aspect, the invention provides a method for advertising a PD-1 antagonist, a platinating agent and an ATR inhibitor, comprising promoting, to a target audience, the use of the combination for treating a subject with a cancer, in some instances based on PD-L1 expression in samples taken from the subject. Promotion may be conducted by any means available. In some embodiments, the promotion is by a package insert accompanying a commercial formulation of the therapeutic combination of the invention. The promotion may also be by a package insert accompanying a commercial formulation of the PD-1 antagonist, the platinating agent, the ATR inhibitor or another medicament (when treatment is a therapy with the therapeutic combination of the invention and a further medicament). Promotion may be by written or oral communication to a physician or health care provider. In some embodiments, the promotion is by a package insert where the package insert provides instructions to receive therapy with the therapeutic combination of the invention, e.g., after measuring PD-L1 expression levels, and in some embodiments, in combination with another medicament. In some embodiments, the promotion is followed by the treatment of the patient with the therapeutic combination of the invention with or without another medicament. In some embodiments, the package insert indicates that the therapeutic combination of the invention is to be used to treat the patient if the patient's cancer sample is characterized by high PD-L1 biomarker levels. In some embodiments, the package insert indicates that the therapeutic combination of the invention is not to be used to treat the patient if the patient's cancer sample expresses low PD-L1 biomarker levels. In some embodiments, a high PD-L1 biomarker level means a measured PD-L1 level that correlates with a likelihood of increased PFS and/or OS when the patient is treated with the therapeutic combination of the invention, and vice versa. In some embodiments, the PFS and/or OS is decreased relative to a patient who is not treated with the therapeutic combination of the invention. In some embodiments, the promotion is by a package insert where the package inset provides instructions to receive therapy with a PD-1 antagonist, a platinating agent and an ATR inhibitor after first measuring PD-L1 levels. In some embodiments, the promotion is followed by the treatment of the patient with a PD-1 antagonist, a platinating agent and an ATR inhibitor with or without another medicament. Further methods of advertising and instructing, or business methods applicable in accordance with the invention are described (for other drugs and biomarkers) in US 2012/0089541, for example.

In some embodiments, the present invention provides a pharmaceutically acceptable composition comprising PD-1 antagonist, preferably an anti-PD-L1 antibody, more preferably avelumab. In some embodiments, the present invention provides a pharmaceutically acceptable composition comprising an ATR inhibitor, preferably any one of Compounds 1 to 5, or a pharmaceutically acceptable salt thereof. In some embodiments, the present invention provides a pharmaceutically acceptable composition comprising a platinating agent, preferably carboplatin. In some embodiments, the present invention provides a pharmaceutically acceptable composition comprising at least two compounds selected from the group consisting of a PD-1 antagonist, an ATR inhibitor and a platinating agent. In some embodiments, the present invention provides a pharmaceutically acceptable composition comprising a PD-1 antagonist, an ATR inhibitor and a platinating agent. In all of the aforementioned pharmaceutical compositions, the pharmaceutical composition may further comprise at least one pharmaceutically acceptable excipient or adjuvant.

Exemplary such pharmaceutically acceptable compositions are described further below and herein.

Typically, the PD-1 antagonist, ATR inhibitor or platinating agent is incorporated into a pharmaceutical composition suitable for administration to a subject, wherein the pharmaceutical composition comprises the compound and a pharmaceutically acceptable carrier. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the compound.

The compositions of the present invention may be in a variety of forms. These include, for example, liquid, semi-solid and solid dosage forms, such as liquid solutions (e.g., injectable and infusible solutions), dispersions or suspensions, tablets, pills, powders, liposomes, and suppositories. The preferred form depends on the intended mode of administration and therapeutic application. In a preferred embodiment, the anti-PD-1 or anti-PD-L1 antibody is administered by intravenous infusion or injection. In another preferred embodiment, the anti-PD-1 or anti-PD-L1 antibody is administered by intramuscular or subcutaneous injection. In a preferred embodiment, the ATR inhibitor is administered by intravenous infusion, injection or orally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion, and by the use of surfactants. Prolonged absorption of injectable compositions can be brought about by including in the composition an agent that delays absorption, for example, monostearate salts and gelatin.

In one embodiment, avelumab is a sterile, clear, and colorless solution intended for IV administration. The contents of the avelumab vials are non-pyrogenic, and do not contain bacteriostatic preservatives. Avelumab is formulated as a 20 mg/mL solution and is supplied in single-use glass vials, stoppered with a rubber septum and sealed with an aluminum polypropylene flip-off seal. For administration purposes, avelumab must be diluted with 0.9% sodium chloride (normal saline solution). Tubing with in-line, low protein binding 0.2 micron filter made of polyether sulfone (PES) is used during administration.

In a further aspect, a kit is provided comprising a PD-1 antagonist, a platinating agent and an ATR inhibitor.

In a further aspect, a kit is provided comprising a PD-1 antagonist and a package insert comprising instructions for using the PD-1 antagonist in combination with a platinating agent and an ATR inhibitor to treat or delay progression of a cancer in a subject. Also provided is a kit comprising a platinating agent and a package insert comprising instructions for using the platinating agent in combination with a PD-1 antagonist and an ATR inhibitor to treat or delay progression of a cancer in a subject. Also provided is a kit comprising an ATR inhibitor, and a package insert comprising instructions for using the ATR inhibitor in combination with a PD-1 antagonist and a platinating agent to treat or delay progression of a cancer in a subject. The kit can comprise a first container, a second container, a third container and a package insert, wherein the first container comprises at least one dose of a medicament comprising the PD-1 antagonist, the second container comprises at least one dose of a medicament comprising the ATR inhibitor, the third container comprises at least one dose of a medicament comprising the platinating agent and the package insert comprises instructions for treating a subject for cancer using the medicaments. Two or all three of the PD-1 antagonist, the ATR inhibitor and the platinating agent may also be comprised in a single container. The containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. The instructions can state that the medicaments are intended for use in treating a subject having a cancer that tests positive for PD-L1 expression by an immunohistochemical (IHC) assay. Thus, this disclosure also provides a kit for determining if the combination of the invention is suitable for therapeutic treatment of a cancer patient, comprising means for determining a protein level of PD-L1, or the expression level of its RNA, in a sample isolated from the patient and instructions for use. In another aspect, the kit further comprises a PD-1 antagonist, an ATR inhibitor and/or a platinating agent. In one aspect of the invention, the determination of a high PD-L1 level indicates increased PFS or OS when the patient is treated with the therapeutic combination of the invention.

In one embodiment of the kit, the means for determining the PD-L1 peptide level are antibodies with specific binding to PD-L1, respectively.

In a further aspect, a biomarker is provided to measure the response to the treatment with a PD-1 antagonist, an ATR inhibitor and/or a platinating agent. In some embodiments, the biomarker measures the response to the treatment with an ATR inhibitor and a platinating agent. Preferably, the biomarker measures the response to the treatment with a PD-1 antagonist, an ATR inhibitor and a platinating agent. The treatment with the PD-1 antagonist, the ATR inhibitor and/or the platinating agent may occur in accordance with the treatment regimens disclosed above. The biomarker is preferably an interferon, more preferably a human interferon. In some embodiments, the interferon is selected from the group consisting of interferon-alpha, interferon-beta and interferon-gamma. In some embodiments, both interferon alpha and interferon beta are measured. In some embodiments, interferon-gamma is measured. The expression of the interferon biomarker correlates with treatment response, wherein an increased expression of the biomarker indicates that the patient is responsive to the treatment. Accordingly, in some embodiments a method is provided to measure the response to the treatment of a patient having cancer with a PD-1 antagonist, an ATR inhibitor and/or a platinating agent, wherein the expression level of interferon is measured. In some embodiments, the method comprises a second step of comparing the interferon expression level from the patient with a standard value, for instance, the interferon expression level of a control subject or group, wherein an expression level of interferon in the patient above the standard value indicates that the patient responds to the treatment. For the triple combination treatment with a PD-1 antagonist, an ATR inhibitor and a platinating agent, the interferon expression level of the control subject or group may derive from a subject or a group of subjects that were treated with only two of these compounds, e.g., the ATR inhibitor and the platinating agent, only one of these compounds, or, preferably, the subject or group of subjects were untreated. Similarly, for the treatment with two compounds, e.g., an ATR inhibitor and a platinating agent, the control subject or group of subjects were treated with only one of the two compounds or, preferably, were untreated. In some embodiments, the method comprises a third step, wherein the results from the comparison result in the adaptation of the treatment. For instance, the treatment may be stopped, or the dosing of the drugs may be adapted. The expression level of the biomarker can be measured by methods known in the art. For instance, the expression level can be determined at the protein or the mRNA level. In some instances, the RNA expression level is determined by way of RNA sequencing.

Further Embodiments

1. A PD-1 antagonist, an ATR inhibitor and a platinating agent for use as a medicament.
2. A PD-1 antagonist, an ATR inhibitor and a platinating agent for use in a method for treating a cancer.
3. The compounds for use according to item 1 or 2, wherein the PD-1 antagonist is an anti-PD-L1 antibody, or an antigen-binding fragment thereof.
4. The compounds for use according to any one of items 1 to 3, wherein the PD-1 antagonist is an anti-PD-L1 antibody, or an antigen-binding fragment thereof, comprising a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6.

5. The compounds for use according to any one of items 1 to 4, wherein the PD-1 antagonist is an anti-PD-L1 antibody, or an antigen-binding fragment thereof, which comprises the heavy chain having amino acid sequences of SEQ ID NOs: 7 or 8 and the light chain having amino acid sequence of SEQ ID NO: 9.

6. The compounds for use according to any one of item 1 to 5, wherein the PD-1 antagonist is avelumab.

7. The compounds for use according to any one of items 1 to 6, wherein the ATR inhibitor is a compound represented by Formula A-I-a:

A-I-a

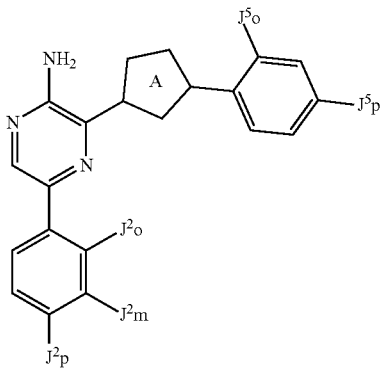

or a pharmaceutically salt thereof,
wherein:
Ring A

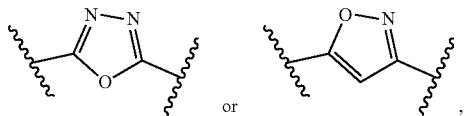 [SMILES: *c1nnc(*)o1 ; *c1cc(*)on1]

$J^5o$ is H, F, Cl, $C_{1-4}$aliphatic, $O(C_{1-3}$aliphatic), or OH;
$J^5p$ is

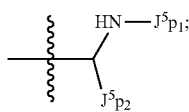

$J^5p_1$ is H, $C_{1-4}$aliphatic, oxetanyl, tetrahydrofuranyl, tetrahydropyranyl; wherein $J^5p_1$ is optionally substituted with 1-2 occurrences of OH or halo;
$J^5p_2$ is H, methyl, ethyl, $CH_2F$, $CF_3$, or $CH_2OH$;
$J^2o$ is H, CN, or $SO_2CH_3$;
$J^2m$ is H, F, Cl, or methyl;
$J^2p$ is —$SO_2(C_{1-6}$alkyl), —$SO_2(C_{3-6}$cycloalkyl), —$SO_2$(4-6 membered heterocyclyl), —$SO_2(C_{1-4}$alkyl)$N(C_{1-4}$alkyl)$_2$, or —$SO_2(C_{1-4}$alkyl)-(4-6 membered heterocyclyl), wherein said heterocyclyl contains 1 heteroatom selected from the group consisting of oxygen, nitrogen, and sulfur; and wherein said $J^2p$ is optionally substituted with 1-3 occurrences halo, OH, or $O(C_{1-4}$alkyl);

or wherein the ATR inhibitor is a compound represented by Formula A-II-a:

A-II-a

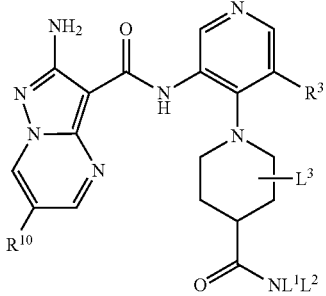

or a pharmaceutically acceptable salt or prodrug thereof,
wherein:
$R^{10}$ is fluoro, chloro, or —$C(J^{10})_2CN$;
$J^{10}$ is independently H or $C_{1-2}$alkyl; or
two occurrences of $J^1$, together with the carbon atom to which they are attached, form an optionally substituted 3-4 membered carbocyclic ring;
$R^3$ is H; chloro; fluoro; $C_{1-4}$alkyl optionally substituted with 1-3 occurrences of halo; $C_{3-4}$cycloalkyl; —CN; or a $C_{1-3}$aliphatic chain, wherein up to two methylene units of the aliphatic chain are optionally replaced with —O—, —$NR^a$—, —C(O)—, or —S(O)Z;
$L^1$ is H; a 3-7 membered aromatic or non-aromatic ring having 0-2 heteroatoms selected from the group consisting of oxygen, nitrogen, and sulfur; or a $C_{1-4}$aliphatic chain, wherein up to two methylene units of the aliphatic chain are optionally replaced with —O—, —$NR^a$—, —C(O)—, or —$S(O)_z$; each $L^1$ is optionally substituted with $C_{1-4}$aliphatic; —CN; halo; —OH; or a 3-6 membered non-aromatic ring having 0-2 heteroatoms selected from the group consisting of oxygen, nitrogen, and sulfur;
$L^2$ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —$NR^a$—, —C(O)—, or —$S(O)_z$; each $L^2$ is optionally substituted with $C_{1-4}$aliphatic; —CN; halo; —OH; or a 3-6 membered non-aromatic ring having 0-2 heteroatoms selected from the group consisting of oxygen, nitrogen, and sulfur; or
$L^1$ and $L^2$, together with the nitrogen to which they are attached, form a Ring D; Ring D is optionally substituted with 0-5 occurrences of $J^G$;
$L^3$ is H, $C_{1-3}$aliphatic, or CN; Ring D is a 3-7 membered heterocyclyl ring having 1-2 heteroatoms selected from the group consisting of oxygen, nitrogen, and sulfur; or an 7-12 membered fully saturated or partially unsaturated bicyclic ring having 1-5 heteroatoms selected from the group consisting of oxygen, nitrogen, and sulfur;
$J^G$ is independently halo; —CN; —$N(R^o)_2$; →O; a 3-6 membered carbocycyl; a 3-6 membered heterocyclyl having 1-2 heteroatoms selected from the group consisting of oxygen, nitrogen, and sulfur; or a $C_{1-4}$alkyl chain, wherein up to two methylene units of the alkyl chain are optionally replaced with —O—, —$NR^a$—, —C(O)—, or —S(O)$_z$—; each $J^G$ is optionally substituted with 0-2 occurrences of $J^K$;

two occurrences of $J^G$ on the same atom, together with the atom to which they are joined, form a 3-6 membered ring having 0-2 heteroatoms selected from the group consisting of oxygen, nitrogen, and sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from the group consisting of oxygen, nitrogen, and sulfur;

z is 0, 1, or 2; and $R^a$ and $R^o$ are independently H or $C_{1-4}$alkyl.

8. The compounds for use according to any one of items 1 to 7, wherein the ATR inhibitor is selected from the group consisting of Compound 1, or a pharmaceutically acceptable salt thereof, Compound 2, or a pharmaceutically acceptable salt thereof, Compound 3, or a pharmaceutically acceptable salt thereof, Compound 4, or a pharmaceutically acceptable salt thereof, and Compound 5, or a pharmaceutically acceptable salt thereof.

9. The compounds for use according to any one of items 1 to 8, wherein the ATR inhibitor is Compound 1, or a pharmaceutically acceptable salt thereof.

10. The compounds for use according to any one of items 1 to 9, wherein the platinating agent is selected from the group consisting of cisplatin, carboplatin and oxaliplatin.

11. The compounds for use according to item 10, wherein the platinating agent is carboplatin.

12. The compounds for use according to any one of items 1 to 11, wherein the anti-PD-L1 antibody is avelumab, the ATR inhibitor is Compound 1, or a pharmaceutically acceptable salt thereof, and the platinating agent is carboplatin.

13. The compounds for use according to any one of items 1 to 12, wherein the subject is human.

14. The compounds for use according to any one of items 1 to 13, wherein the cancer is selected from cancer of lung, head and neck, colon, urothelium, prostate, esophagus, bladder, stomach, neuroendocrine system, mesenchyme, breast, ovarian, primary peritoneal, fallopian tube, pancreas, and histological subtypes thereof 15. The compounds for use according to any one of items 1 to 14, wherein the cancer is selected from PARPi-resistant recurrent ovarian cancer, PARPi-resistant recurrent primary peritoneal cancer, PARPi-resistant recurrent fallopian tube cancer, small-cell lung cancer (SCLC), non-small-cell lung cancer (NSCLC), squamous cell carcinoma of the head and neck (SCCHN), colorectal cancer (CRC), primary neuroendocrine tumors and sarcoma.

16. The compounds for use according to any one of items 1 to 15, wherein the cancer is a PARPi-resistant recurrent cancer selected from ovarian cancer, primary peritoneal cancer, and fallopian tube cancer.

17. The compounds for use according to any one of items 1 to 16, wherein the PD-1 antagonist, preferably avelumab, is administered at a dose selected from the group consisting of: about 1 mg/kg Q2W, about 2 mg/kg Q2W, about 3 mg/kg Q2W, about 5 mg/kg Q2W, about 10 mg/kg Q2W, about 1 mg/kg Q3W, about 2 mg/kg Q3W, about 3 mg/kg Q3W, about 5 mg/kg Q3W, about 10 mg/kg Q3W and about 20 mg/kg Q3W.

18. The compounds for use according to item 17, wherein the PD-1 antagonist, preferably avelumab, is administered at a dose of about 10 mg/kg Q2W or about 20 mg/kg Q3W.

19. The compounds for use according to any one of items 1 to 16, wherein the PD-1 antagonist, preferably avelumab, is administered at a flat dose selected from the group consisting of: about 400 mg Q2W, about 450 mg Q2W, about 500 mg Q2W, about 550 mg Q2W, about 600 mg Q2W, about 650 mg Q2W, about 700 mg Q2W, about 750 mg Q2W, about 800 mg Q2W, about 800 mg Q3W, about 900 mg Q3W, about 1000 mg Q3W, about 1100 mg Q3W, about 1200 mg Q3W, about 1300 mg Q3W, about 1400 mg Q3W, about 1500 mg Q3W and about 1600 mg Q3W.

20. The compounds for use according to item 19, wherein the PD-1 antagonist, preferably avelumab, is administered at a flat dose of about 800 mg Q2W or about 1600 mg Q3W.

21. The compounds for use according to any one of items 1 to 20, wherein the ATR inhibitor, preferably Compound 1, or a pharmaceutically acceptable salt thereof, is administered at a dose selected from the group consisting of: between about 20 mg/m$^2$ and about 300 mg/m$^2$, between about 30 mg/m$^2$ and about 240 mg/m$^2$, between about 40 mg/m$^2$ and about 240 mg/m$^2$, between about 40 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, and between about 80 mg/m$^2$ and about 100 mg/m$^2$.

22. The compounds for use according to item 21, wherein the ATR inhibitor, preferably Compound 1, or a pharmaceutically acceptable salt thereof, is administered at a dose of between about 80 mg/m$^2$ and about 100 mg/m$^2$, preferably at a dose of about 90 mg/m$^2$.

23. The compounds for use according to any one of items 1 to 22, wherein the platinating agent, preferably carboplatin, is administered at a target AUC selected from the group consisting of: between about 3 mg/mL·min and about 7 mg/mL·min, between about 3.5 mg/mL·min and about 6 mg/mL·min, between about 4 mg/mL·min and about 6 mg/mL·min, between about 4 mg/mL·min and about 5.5 mg/mL·min, and between about 4 mg/mL·min and about 5 mg/mL·min.

24. The compounds for use according item 23, wherein the platinating agent, preferably carboplatin, is administered at a target AUC of about 5 mg/mL·min.

25. The compounds for use according to any one of items 1 to 24, wherein the PD-1 antagonist is avelumab and administered Q3W with a dosage of about 1600 mg, the platinating agent is carboplatin and administered Q3W at a dosage with a target AUC of about 5 mg/mL·min and the ATR inhibitor is Compound 1 and administered Q3W at a dosage of about 90 mg/m$^2$.

26. The compounds for use according to any one of items 1 to 25, wherein the compounds are administered in a second-line or higher treatment of the cancer.

27. The compounds for use according to any one of items 1 to 26, wherein the cancer was resistant or became resistant to prior therapy.

28. The compounds for use according to any one of items 1 to 27, wherein the cancer is selected from the group of PARPi-resistant recurrent ovarian cancer, PARPi-resistant recurrent primary peritoneal cancer, PARPi-resistant recurrent fallopian tube cancer, pre-treated relapsing metastatic NSCLC, unresectable locally advanced NSCLC, pre-treated SCLC ED, SCLC unsuitable for systemic treatment, pre-treated relapsing or metastatic SCCHN, recurrent SCCHN eligible for re-irradiation, and pre-treated microsatellite status instable low (MSI-L) or microsatellite status stable (MSS) metastatic colorectal cancer (mCRC).
29. The compounds for use according to any one of items 1 to 28, the use further comprising administering a chemotherapy (CT), radiotherapy (RT), or chemotherapy and radiotherapy (CRT) to the subject.
30. The compounds for use according to any one of items 1 to 29, wherein the method of treatment comprises a lead phase, optionally followed by a maintenance phase after completion of the lead phase.
31. The compounds for use according to item 30, wherein the PD-1 antagonist, the ATR inhibitor and the platinating agent are administered during the lead phase, whereas during the maintenance phase the PD-1 antagonist but not the ATR inhibitor and the platinating agent are administered.
32. A method for treating a cancer in a subject in need thereof, comprising administering to the subject in any order a PD-1 antagonist, an ATR inhibitor and a platinating agent.
33. The method according to item 32, wherein the PD-1 antagonist is an anti-PD-L1 antibody, or an antigen-binding fragment thereof.
34. The method according to item 33, wherein the anti-PD-L1 antibody, or antigen-binding fragment thereof, mediates antibody-dependent cellular cytotoxicity.
35. The method according to item 33 or 34, wherein the anti-PD-L1 antibody, or antigen-binding fragment thereof, comprises a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6.
36. The method according to any one of items 33-35, wherein the anti-PD-L1 antibody is avelumab.
37. The method according to any one of items 32-36, wherein the ATR inhibitor is selected from the group consisting of Compound 1, or a pharmaceutically acceptable salt thereof, Compound 2, or a pharmaceutically acceptable salt thereof, Compound 3, or a pharmaceutically acceptable salt thereof, Compound 4, or a pharmaceutically acceptable salt thereof, and Compound 5, or a pharmaceutically acceptable salt thereof.
38. The method according to item 37, wherein the ATR inhibitor is Compound 1, or a pharmaceutically acceptable salt thereof.
39. The method according to any one of items 32-38, wherein the platinating agent is selected from the group consisting of cisplatin, carboplatin and oxaliplatin.
40. The method according to item 39, wherein the platinating agent is carboplatin.
41. The method according to any one of items 32-40, wherein the cancer is selected from cancer of lung, head and neck, colon, urothelium, prostate, esophagus, bladder, stomach, neuroendocrine system, mesenchyme, breast, ovarian, primary peritoneal, fallopian tube, pancreas, and histological subtypes thereof.
42. The method according to any one of items 32-41, wherein the subject underwent at least one round of prior cancer therapy; wherein, optionally, the cancer was resistant or became resistant to prior therapy.
43. The method according to item 42, wherein the subject previously received PARPi-based therapy, wherein, optionally, the subject relapsed or progressed after receiving the PARPi-based therapy.
44. The method according to item 43, wherein the cancer is a PARPi-resistant recurrent cancer selected from ovarian cancer, primary peritoneal cancer, and fallopian tube cancer.
45. The method according to any one of items 32-44, wherein the PD-1 antagonist is avelumab and administered Q3W with a dosage of about 1600 mg, the platinating agent is carboplatin and administered Q3W at a dosage with a target AUC of about 5 mg/mL·min and the ATR inhibitor is Compound 1, or a pharmaceutically acceptable salt thereof, and administered Q3W at a dosage of about 90 mg/m$^2$.
46. The method according to any one of items 32-45, further comprising administering a chemotherapy (CT), radiotherapy (RT), or chemotherapy and radiotherapy (CRT) to the subject.
47. The method according to any one of items 32-46, which comprises a lead phase, optionally followed by a maintenance phase after completion of the lead phase.
48. The method according to item 47, wherein the PD-1 antagonist, the ATR inhibitor and the platinating agent are administered during the lead phase, whereas during the maintenance phase the PD-1 antagonist but not the ATR inhibitor and the platinating agent are administered.
49. A pharmaceutical composition comprising a PD-1 antagonist, an ATR inhibitor, a platinating agent and at least a pharmaceutically acceptable carrier, diluent, excipient and/or adjuvant.
50. A combination comprising a PD-1 antagonist, an ATR inhibitor and a platinating agent.
51. Use of the pharmaceutical composition according to item 49, or the combination according to item 50, for the manufacture of a medicament for the treatment of cancer.
52. The combination according to item 49, or the pharmaceutical composition according to item 50, for use as a medicament.
53. A kit comprising a PD-1 antagonist, an ATR inhibitor and a platinating agent.
54. A kit comprising a PD-1 antagonist and a package insert comprising instructions for using the PD-1 antagonist in combination with a platinating agent and an ATR inhibitor to treat or delay progression of a cancer in a subject.
55. A kit comprising a platinating agent and a package insert comprising instructions for using the platinating agent in combination with a PD-1 antagonist and an ATR inhibitor to treat or delay progression of a cancer in a subject.
56. The kit according to item 55, wherein the kit further comprises a package insert comprising instructions for using the PD-1 antagonist, the ATR inhibitor and the platinating agent to treat or delay progression of a cancer in a subject.
57. The kit according to item 56, which comprises a first container, a second container, a third container and a package insert, wherein the first container comprises at least one dose of a medicament comprising the PD-1 antagonist, the second container comprises at least one dose of a medicament comprising the ATR inhibitor, the third container comprises at least one dose of a medicament comprising the platinating agent and the package insert comprises instructions for treating a subject for cancer using the medicaments; wherein, further optionally, the instructions state that the medicaments are intended for use in treating a subject having a cancer that tests positive for PD-L1 expression, preferably by means of an immunohistochemical assay.

58. A kit comprising an ATR inhibitor and a package insert comprising instructions for using the ATR inhibitor in combination with a PD-1 antagonist and a platinating agent to treat or delay progression of a cancer in a subject.

59. A method for advertising a PD-1 antagonist in combination with a platinating agent and an ATR inhibitor, comprising promoting, to a target audience, the use of the combination for treating a subject with a cancer.

60. Use of a biomarker to measure the response of a subject having cancer to the treatment with one or more of a PD-1 antagonist, an ATR inhibitor and a platinating agent.

61. The use according to item 60, wherein the treatment is with an ATR inhibitor and a platinating agent.

62. The use according to item 60, wherein the treatment is with a PD-1 antagonist, an ATR inhibitor and a platinating agent.

63. The use according to any one of items 60-62, wherein the biomarker is an interferon.

64. The use according to item 63, wherein the biomarker is selected from the group consisting of interferon-alpha, interferon-beta and interferon-gamma.

65. The use according to item 63 or 64, wherein the interferon is human.

66. The use according to any one of items 60-65, wherein the level of expression of the interferon is measured and compared to a control expression level.

67. The use according to item 66, wherein an increased level of expression, as compared to the control, indicates that the subject is responsive to the treatment with the PD-1 antagonist, the ATR inhibitor and/or the platinating agent.

68. The use according to any one of items 60 and 62-67, wherein the PD-1 antagonist is an anti-PD-L1 antibody, or an antigen-binding fragment thereof.

69. The use according to any one of items 60 and 62-68, wherein the PD-1 antagonist is an anti-PD-L1 antibody, or an antigen-binding fragment thereof, comprising a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6.

70. The use according to any one of items 60 and 62-69, wherein the PD-1 antagonist is an anti-PD-L1 antibody, or an antigen-binding fragment thereof, which comprises the heavy chain having amino acid sequences of SEQ ID NOs: 7 or 8 and the light chain having amino acid sequence of SEQ ID NO: 9.

71. The use according to any one of items 60 and 62-70, wherein the PD-1 antagonist is avelumab.

72. The use according to any one of items 60-71, wherein the ATR inhibitor is selected from the group consisting of Compound 1, or a pharmaceutically acceptable salt thereof, Compound 2, or a pharmaceutically acceptable salt thereof, Compound 3, or a pharmaceutically acceptable salt thereof, Compound 4, or a pharmaceutically acceptable salt thereof, and Compound 5, or a pharmaceutically acceptable salt thereof.

73. The use according to any one of items 60-72, wherein the ATR inhibitor is Compound 1, or a pharmaceutically acceptable salt thereof.

74. The use according to any one of items 60-73, wherein the platinating agent is selected from the group consisting of cisplatin, carboplatin and oxaliplatin.

75. The use according to any one of items 60-74, wherein the platinating agent is carboplatin.

76. The use according to any one of items 60 and 62-75, wherein the anti-PD-L1 antibody is avelumab, the ATR inhibitor is Compound 1, or a pharmaceutically acceptable salt thereof, and the platinating agent is carboplatin.

77. A method to measure the response of a subject to the treatment with a PD-1 antagonist, an ATR inhibitor and a platinating agent comprising the following steps:
    a. Measuring the expression level of one or more interferons in a subject having cancer after the subject has been treated with the PD-1 antagonist, the ATR inhibitor and the platinating agent;
    b. Comparing said expression level to a control expression level of the one or more interferons; wherein the subject having cancer responded to the treatment if the one or more levels of interferon expression in the subject having cancer exceeds the one or more control levels of interferon expression and the subject having cancer did not respond to the treatment if the one or more levels of interferon expression in the subject having cancer does not exceed the one or more control levels of interferon expression.

78. The method according to item 77, wherein the one or more control expression levels of interferon are the one or more levels of interferon measured in a subject that has not been treated or a group of subjects that have not been treated.

79. The method according to item 77 or 78, wherein the method further comprises the following step:
    c. If the subject having cancer responded to the treatment continuing with the treatment and/or if the subject having cancer did not respond to the treatment, stopping the treatment or modifying the dose of the treatment.

80. The method according to any one of items 77-79, wherein the one or more interferon is selected from the group consisting of interferon-alpha, interferon-beta and interferon-gamma.

81. The method according to item 80, wherein the one or more interferon is interferon-alpha and interferon-beta.

82. The method according to item 80, wherein the one or more interferon is interferon-gamma.

83. The method according to item 32-48, wherein, after the administration of the PD-1 antagonist, the ATR inhibitor and the platinating agent, the expression level of one or more interferons is measured in the subject and compared to a control expression level of the one or more interferons; wherein the subject responded to the treatment if the one or more levels of interferon expression in the subject exceeds the one or more control levels of interferon expression and the subject did not respond to the treatment if the one or more levels of interferon expression in the subject does not exceed the one or more control levels of interferon expression.

84. The method according to item 83, wherein the treatment is continued after comparing the one or more interferon expression levels if the subject responded to the treatment and/or the treatment is discontinued or the dosing of the treatment is changed after comparing the one or more interferon expression levels if the subject did not respond to the treatment.
85. The method according to item 83 or 84, wherein the one or more interferon is selected from the group consisting of interferon-alpha, interferon-beta and interferon-gamma.
86. The method according to item 85, wherein the one or more interferon is interferon-alpha and interferon-beta.
87. The method according to item 85, wherein the one or more interferon is interferon-gamma.

All the references cited herein are incorporated by reference in the disclosure of the invention hereby.

It is to be understood that this invention is not limited to the particular molecules, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. The techniques that are essential according to the invention are described in detail in the specification. Other techniques which are not described in detail correspond to known standard methods that are well known to a person skilled in the art, or the techniques are described in more detail in cited references, patent applications or standard literature. Provided that no other hints in the application are given, they are used as examples only, they are not considered to be essential according to the invention, but they can be replaced by other suitable tools and biological materials.

Although methods and materials similar or equivalent to those described herein can be used in the practice or testing of the present invention, suitable examples are described below. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims. The present invention having been described in summary and in detail, is illustrated and not limited by the following examples.

EXAMPLES

Example 1

Two ATR inhibitors, ATRi 1 (Compound 1) and ATRi 2 (Compound 2), were independently tested in combination with various chemotherapeutic agents, including the platinating agents carboplatin, cisplatin and oxaliplatin, to analyze the combinatorial effect on cell growth inhibition. The ATR inhibitors ATRi 1 and ATRi 2 were used at 0.02 μM and 0.4 μM, respectively and the platinating agents were used in increasing concentrations: Carboplatin: 100 μM, 25 μM, 6.25 μM, 1.56 μM, 391 nM; Cisplatin: 10 μM, 2.5 μM, 625 nM, 156 nM, 39 nM; Oxaliplatin: 25 μM, 6.25 μM, 1.56 μM, 391 nM, 98 nM. 35 different cancer cell lines were treated with said combinations.

Experimental conditions/treatment schedule: Cells were seeded in 96-well microtiter plates under standard conditions. The cells were allowed to stand for 48 hours prior to treatment. The treatment was performed for 120 hours and stopped by addition of trichloracetic acid followed by Sulforhodamine B staining. Combinations included simultaneous addition of both agent pairs.

The combinatorial effect of the compounds was determined by measuring their cell growth inhibition as compared to the inhibition observed for monotherapies of these compounds using the same concentrations as used for the combinations. The combination effect has been calculated as the excess over the linear combination of the monotherapy effects using the BLISS independence model (E1+2=E1+E2−E1 E2). The average BLISS excess is calculated as the average excess over the linear combination of the monotherapy effects across all inhibitor concentrations. Positive BLISS excess values above 0.1 describe a synergistic effect, and BLISS excess values below −0.1 describe an antagonistic effect. BLISS excess measures of the combination of two ATR inhibitors and various chemotherapeutic agents, including the mentioned platinating agents, for 35 cell lines are shown in FIGS. 3A and 3B.

Figure 3B:
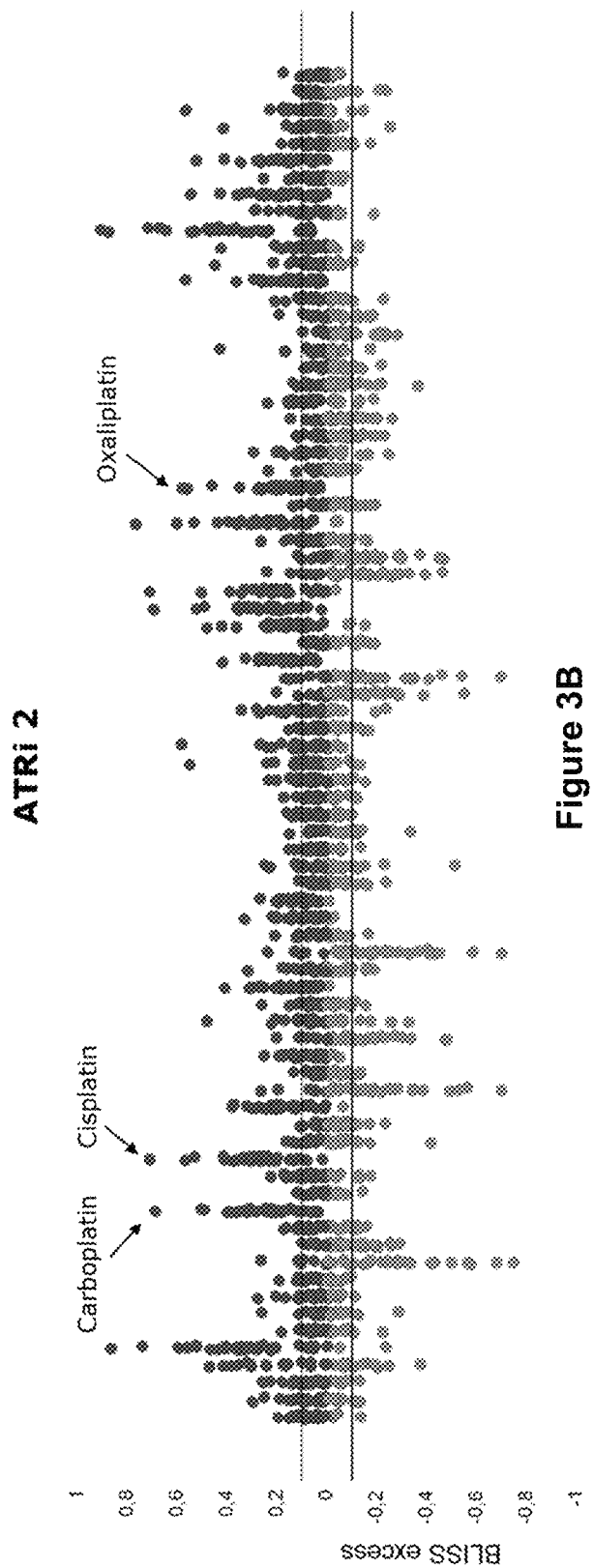

As observed in FIGS. 3A and 3B, the two ATR inhibitors show synergistic cell growth inhibition when combined with the platinating agents carboplatin, cisplatin and oxaliplatin.

A particularly strong therapeutic effect was observed in the following settings:

| Platinating agent | ATRi | Cell line | Origin | BLISS excess |
|---|---|---|---|---|
| Carboplatin | ATRi 1 | A549 | lung | 0.121196631 |
| Carboplatin | ATRi 1 | A673 | muscle | 0.477068952 |
| Carboplatin | ATRi 1 | BXPC3 | pancreas | 0.146420188 |
| Carboplatin | ATRi 1 | CALU6 | lung | 0.163731081 |
| Carboplatin | ATRi 1 | COLO205 | colon | 0.147193806 |
| Carboplatin | ATRi 1 | DU145 | prostate | 0.373382961 |
| Carboplatin | ATRi 1 | HL-60 | hematological | 0.288214316 |
| Carboplatin | ATRi 1 | LOVO | colon | 0.108299031 |
| Carboplatin | ATRi 1 | MCF7 | breast | 0.134628294 |
| Carboplatin | ATRi 1 | MDAMB231 | breast | 0.356878196 |
| Carboplatin | ATRi 1 | MDAMB435 | skin | 0.35185886 |
| Carboplatin | ATRi 1 | MHHES1 | bone | 0.126437348 |
| Carboplatin | ATRi 1 | MIAPACA2 | pancreas | 0.308854247 |
| Carboplatin | ATRi 1 | MV4-11 | hematological | 0.148229027 |
| Carboplatin | ATRi 1 | NCIH460 | lung | 0.188252583 |
| Carboplatin | ATRi 1 | PANC1 | pancreas | 0.234922833 |
| Carboplatin | ATRi 1 | PBMC | hematological | 0.10145506 |
| Carboplatin | ATRi 1 | RDES | bone | 0.322748341 |
| Carboplatin | ATRi 1 | SAOS2 | bone | 0.135893442 |
| Carboplatin | ATRi 1 | SW620 | colon | 0.17400545 |
| Carboplatin | ATRi 1 | U2OS | bone | 0.450328304 |
| Carboplatin | ATRi 1 | WSU-NHL | hematological | 0.248508988 |
| Carboplatin | ATRi 2 | A204 | muscle | 0.249590261 |
| Carboplatin | ATRi 2 | A375 | skin | 0.17940193 |
| Carboplatin | ATRi 2 | A549 | lung | 0.175413086 |
| Carboplatin | ATRi 2 | A673 | muscle | 0.50494045 |
| Carboplatin | ATRi 2 | ASPC1 | pancreas | 0.226636349 |
| Carboplatin | ATRi 2 | BXPC3 | pancreas | 0.283986217 |
| Carboplatin | ATRi 2 | CALU6 | lung | 0.223137608 |
| Carboplatin | ATRi 2 | COLO205 | colon | 0.252726587 |
| Carboplatin | ATRi 2 | DU145 | prostate | 0.492974 |
| Carboplatin | ATRi 2 | GRANTA-519 | hematological | 0.151399735 |
| Carboplatin | ATRi 2 | HCT116 | colon | 0.118098944 |
| Carboplatin | ATRi 2 | HL-60 | hematological | 0.322629825 |
| Carboplatin | ATRi 2 | HT29 | colon | 0.312381037 |
| Carboplatin | ATRi 2 | IGROV1 | ovary | 0.217706292 |
| Carboplatin | ATRi 2 | LOVO | colon | 0.301650615 |
| Carboplatin | ATRi 2 | MCF7 | breast | 0.130566415 |
| Carboplatin | ATRi 2 | MDAMB231 | breast | 0.401300128 |
| Carboplatin | ATRi 2 | MDAMB435 | skin | 0.333422413 |
| Carboplatin | ATRi 2 | MIAPACA2 | pancreas | 0.363426483 |
| Carboplatin | ATRi 2 | MV4-11 | hematological | 0.219553367 |
| Carboplatin | ATRi 2 | NCIH460 | lung | 0.197141594 |

-continued

| Platinating agent | ATRi | Cell line | Origin | BLISS excess |
|---|---|---|---|---|
| Carboplatin | ATRi 2 | PANC1 | pancreas | 0.236938398 |
| Carboplatin | ATRi 2 | PBMC | hematological | 0.21450182 |
| Carboplatin | ATRi 2 | RDES | bone | 0.386208527 |
| Carboplatin | ATRi 2 | SAOS2 | bone | 0.216863472 |
| Carboplatin | ATRi 2 | SW620 | colon | 0.168742165 |
| Carboplatin | ATRi 2 | U2OS | bone | 0.687381648 |
| Carboplatin | ATRi 2 | U87MG | brain | 0.234321881 |
| Carboplatin | ATRi 2 | WSU-NHL | hematological | 0.355193663 |
| Cisplatin | ATRi 1 | A204 | muscle | 0.19694654 |
| Cisplatin | ATRi 1 | A375 | skin | 0.124244252 |
| Cisplatin | ATRi 1 | A549 | lung | 0.153418836 |
| Cisplatin | ATRi 1 | A673 | muscle | 0.500829877 |
| Cisplatin | ATRi 1 | BXPC3 | pancreas | 0.114832942 |
| Cisplatin | ATRi 1 | CALU6 | lung | 0.19281478 |
| Cisplatin | ATRi 1 | COLO205 | colon | 0.247980039 |
| Cisplatin | ATRi 1 | DU145 | prostate | 0.489546417 |
| Cisplatin | ATRi 1 | GRANTA-519 | hematological | 0.106528853 |
| Cisplatin | ATRi 1 | HL-60 | hematological | 0.359186244 |
| Cisplatin | ATRi 1 | IGROV1 | ovary | 0.128205257 |
| Cisplatin | ATRi 1 | LOVO | colon | 0.133119727 |
| Cisplatin | ATRi 1 | MCF7 | breast | 0.214646867 |
| Cisplatin | ATRi 1 | MDAMB231 | breast | 0.356521065 |
| Cisplatin | ATRi 1 | MDAMB435 | skin | 0.3829918 |
| Cisplatin | ATRi 1 | MHHES1 | bone | 0.192779097 |
| Cisplatin | ATRi 1 | MIAPACA2 | pancreas | 0.413789124 |
| Cisplatin | ATRi 1 | MV4-11 | hematological | 0.231201135 |
| Cisplatin | ATRi 1 | NCIH460 | lung | 0.282144394 |
| Cisplatin | ATRi 1 | PANC1 | pancreas | 0.197466011 |
| Cisplatin | ATRi 1 | PBMC | hematological | 0.170744463 |
| Cisplatin | ATRi 1 | RDES | bone | 0.382471067 |
| Cisplatin | ATRi 1 | SAOS2 | bone | 0.178936662 |
| Cisplatin | ATRi 1 | SW620 | colon | 0.222950882 |
| Cisplatin | ATRi 1 | U2OS | bone | 0.502848671 |
| Cisplatin | ATRi 1 | U87MG | brain | 0.146487922 |
| Cisplatin | ATRi 1 | WSU-NHL | hematological | 0.176223278 |
| Cisplatin | ATRi 2 | A204 | muscle | 0.338160004 |
| Cisplatin | ATRi 2 | A375 | skin | 0.266859254 |
| Cisplatin | ATRi 2 | A549 | lung | 0.243195538 |
| Cisplatin | ATRi 2 | A673 | muscle | 0.529955464 |
| Cisplatin | ATRi 2 | ASPC1 | pancreas | 0.217564753 |
| Cisplatin | ATRi 2 | BXPC3 | pancreas | 0.264428379 |
| Cisplatin | ATRi 2 | CALU6 | lung | 0.206811222 |
| Cisplatin | ATRi 2 | COLO205 | colon | 0.289788048 |
| Cisplatin | ATRi 2 | DU145 | prostate | 0.567171683 |
| Cisplatin | ATRi 2 | GRANTA-519 | hematological | 0.237785072 |
| Cisplatin | ATRi 2 | HCT116 | colon | 0.129577463 |
| Cisplatin | ATRi 2 | HL-60 | hematological | 0.332324212 |
| Cisplatin | ATRi 2 | HT29 | colon | 0.375966052 |
| Cisplatin | ATRi 2 | IGROV1 | ovary | 0.265210007 |
| Cisplatin | ATRi 2 | IMR90 | lung | 0.150381193 |
| Cisplatin | ATRi 2 | LOVO | colon | 0.363859362 |
| Cisplatin | ATRi 2 | MCF7 | breast | 0.229404094 |
| Cisplatin | ATRi 2 | MDAMB231 | breast | 0.335689756 |
| Cisplatin | ATRi 2 | MDAMB435 | skin | 0.305382726 |
| Cisplatin | ATRi 2 | MDAMB436 | breast | 0.105941911 |
| Cisplatin | ATRi 2 | MHHES1 | bone | 0.142251524 |
| Cisplatin | ATRi 2 | MIAPACA2 | pancreas | 0.408497284 |
| Cisplatin | ATRi 2 | MV4-11 | hematological | 0.300599435 |
| Cisplatin | ATRi 2 | NCIH460 | lung | 0.292234633 |
| Cisplatin | ATRi 2 | PANC1 | pancreas | 0.263966822 |
| Cisplatin | ATRi 2 | PBMC | hematological | 0.300277861 |
| Cisplatin | ATRi 2 | RAMOS | hematological | 0.117544179 |
| Cisplatin | ATRi 2 | RDES | bone | 0.416759146 |
| Cisplatin | ATRi 2 | SAOS2 | bone | 0.257010529 |
| Cisplatin | ATRi 2 | SW620 | colon | 0.20073269 |
| Cisplatin | ATRi 2 | U2OS | bone | 0.710054514 |
| Cisplatin | ATRi 2 | U87MG | brain | 0.287615857 |
| Cisplatin | ATRi 2 | WSU-NHL | hematological | 0.305392445 |
| Oxaliplatin | ATRi 1 | A673 | muscle | 0.398164808 |
| Oxaliplatin | ATRi 1 | COLO205 | colon | 0.168087736 |
| Oxaliplatin | ATRi 1 | DU145 | prostate | 0.439897865 |
| Oxaliplatin | ATRi 1 | HL-60 | hematological | 0.278503965 |
| Oxaliplatin | ATRi 1 | HT1080 | connective tissue | 0.171160855 |
| Oxaliplatin | ATRi 1 | MDAMB231 | breast | 0.188547957 |
| Oxaliplatin | ATRi 1 | MDAMB435 | skin | 0.212591265 |
| Oxaliplatin | ATRi 1 | MIAPACA2 | pancreas | 0.212851831 |
| Oxaliplatin | ATRi 1 | MV4-11 | hematological | 0.1369089 |
| Oxaliplatin | ATRi 1 | RDES | bone | 0.332767017 |
| Oxaliplatin | ATRi 1 | U2OS | bone | 0.165598744 |
| Oxaliplatin | ATRi 1 | WSU-NHL | hematological | 0.18190226 |
| Oxaliplatin | ATRi 2 | A204 | muscle | 0.117462267 |
| Oxaliplatin | ATRi 2 | A375 | skin | 0.18963669 |
| Oxaliplatin | ATRi 2 | A549 | lung | 0.140667935 |
| Oxaliplatin | ATRi 2 | A673 | muscle | 0.462537651 |
| Oxaliplatin | ATRi 2 | ASPC1 | pancreas | 0.120760827 |
| Oxaliplatin | ATRi 2 | BXPC3 | pancreas | 0.217521464 |
| Oxaliplatin | ATRi 2 | COLO205 | colon | 0.262943622 |
| Oxaliplatin | ATRi 2 | DU145 | prostate | 0.561849335 |
| Oxaliplatin | ATRi 2 | GRANTA-519 | hematological | 0.193546237 |
| Oxaliplatin | ATRi 2 | HCT116 | colon | 0.106439 |
| Oxaliplatin | ATRi 2 | HL-60 | hematological | 0.272291113 |
| Oxaliplatin | ATRi 2 | HT29 | colon | 0.277891345 |
| Oxaliplatin | ATRi 2 | IGROV1 | ovary | 0.210629861 |
| Oxaliplatin | ATRi 2 | LOVO | colon | 0.256302125 |
| Oxaliplatin | ATRi 2 | MCF7 | breast | 0.225685532 |
| Oxaliplatin | ATRi 2 | MDAMB231 | breast | 0.178692882 |
| Oxaliplatin | ATRi 2 | MDAMB435 | skin | 0.203776377 |
| Oxaliplatin | ATRi 2 | MHHES1 | bone | 0.151955699 |
| Oxaliplatin | ATRi 2 | MIAPACA2 | pancreas | 0.118755662 |
| Oxaliplatin | ATRi 2 | MV4-11 | hematological | 0.127773664 |
| Oxaliplatin | ATRi 2 | NCIH460 | lung | 0.159921419 |
| Oxaliplatin | ATRi 2 | PANC1 | pancreas | 0.100739372 |
| Oxaliplatin | ATRi 2 | PBMC | hematological | 0.23765779 |
| Oxaliplatin | ATRi 2 | RDES | bone | 0.351486564 |
| Oxaliplatin | ATRi 2 | SAOS2 | bone | 0.116150755 |
| Oxaliplatin | ATRi 2 | SW620 | colon | 0.103447461 |
| Oxaliplatin | ATRi 2 | U2OS | bone | 0.580457627 |
| Oxaliplatin | ATRi 2 | U87MG | brain | 0.153359354 |
| Oxaliplatin | ATRi 2 | WSU-NHL | hematological | 0.163869039 |

Example 2: In Vivo Test of Anti-Tumor Efficacy of a Triple Combination Treatment in Murine Subcutaneous MC38 Tumor Model The objective of this study was to evaluate the in vivo anti-tumor efficacy of a triple combination treatment comprising avelumab, a platinating agent (cisplatin or carboplatin) and ATRi 1 (Compound 1) in the subcutaneous MC38 colorectal cancer syngeneic model in C57BL/6 mice.

Cell Culture

The MC38 tumor cells were maintained in vitro as a monolayer culture in DMEM+2 mM glutamine supplemented with 10% heat inactivated fetal bovine serum, 100 U/ml penicillin and 100 µg/ml streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Tumor Inoculation and Animal Grouping

Each mouse was inoculated subcutaneously at the right upper flank with MC38 cells ($3 \times 10^5$) in 0.1 mL of PBS for tumor development. Treatments were started on day 7 after tumor inoculation when the average tumor size reached approximately 80 mm$^3$. The animals were assigned into groups using an Excel-based randomization software performing stratified randomization based upon their tumor volumes. Each group consisted of 10 tumor-bearing mice. The tested compounds were administered to the mice according to the predetermined regimen shown in the experimental design Table 2 and Table 6, respectively.

TABLE 1

| Tested compounds | |
|---|---|
| Tested compounds | Solvent |
| Avelumab | PBS |
| Isotype control | PBS |
| Cisplatin | 0.9% Saline |
| Carboplatin | 0.9% Saline |
| ATRi 1 | 0.5% Methocel K4M Premium/0.25% Tween 20 (solvent also referred to as Vehicle) |

Tumor Measurements and Endpoints

The major endpoint was to see if the tumor growth could be delayed or mice could be cured. Tumor size was measured twice weekly in two dimensions using a caliper, and the volume was expressed in mm$^3$ using the formula: V=0.5 a×b$^2$ where a and b are the long and short diameters of the tumor, respectively. The tumor size was then used for calculation of T/C values. The T/C value (in percent) is an indication of antitumor effectiveness; T and C are the mean volumes of the treated and control groups, respectively, on a given day. TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start. Animals were euthanized as they reached tumor burden of 3,000 mm$^3$ per IACUC regulations and the time to reach this endpoint was used for Kaplan-Meier survival analysis.

Statistical Analysis

Statistical analysis of difference in the tumor volume among the groups were conducted on the data obtained at the best therapeutic time point on day 17 after the start of treatment). A one-way ANOVA was performed, and when a significant F-statistics (a ratio of treatment variance to the error variance) was obtained, comparisons between groups were carried out with Games-Howell test. All data were analyzed using SPSS 17.0. p<0.05 was considered to be statistically significant.

Statistical analysis of difference in survival rate among the groups were conducted on the survival data up to day 66 after the start of treatment. Kaplan-Meier test was performed, all data were analyzed using GraphPad Prism 6.0., comparisons between groups were carried out with Log-rank test, p<0.05 was considered to be statistically significant.

Experiment 2A: Triple Combination of Avelumab, Cisplatin and ATRi 1 in MC38 Model The anti-tumor efficacy of the triple combination avelumab, cisplatin and ATRi 1 was tested according to the above methods and with the experimental design outlined in Table 2.

TABLE 2

Experimental design:

| Group | N[a] | Treatment | Dose | Dosing Route | Schedule |
|---|---|---|---|---|---|
| 1 | 10 | Isotype control | 400 μg | i.v. | Days 3, 6, 9 |
|  |  | 0.9% Saline | — | i.p. | Days 0, 7 |
|  |  | Vehicle | — | p.o. | Days 0, 7 |
| 2 | 10 | Avelumab | 400 μg | i.v. | Days 3, 6, 9 |
|  |  | 0.9% Saline | — | i.p. | Days 0, 7 |
|  |  | Vehicle | — | p.o. | Days 0, 7 |
| 3 | 10 | Isotype control | 400 μg | i.v. | Days 3, 6, 9 |
|  |  | Cisplatin | 3.5 mg/kg | i.p. | Days 0, 7 |
|  |  | Vehicle | — | p.o. | Days 0, 7 |
| 4 | 10 | Isotype control | 400 μg | i.v. | Days 3, 6, 9 |
|  |  | 0.9% Saline | — | i.p. | Days 0, 7 |
|  |  | ATRi 1 | 60 mg/kg | p.o. | Days 0, 7 |
| 5 | 10 | Avelumab | 400 μg | i.v. | Days 3, 6, 9 |
|  |  | Cisplatin | 3.5 mg/kg | i.p. | Days 0, 7 |
|  |  | Vehicle | — | p.o. | Days 0, 7 |
| 6 | 10 | Avelumab | 400 μg | i.v. | Days 3, 6, 9 |
|  |  | 0.9% Saline | — | i.p. | Days 0, 7 |
|  |  | ATRi 1 | 60 mg/kg | p.o. | Days 0, 7 |
| 7 | 10 | Isotype control | 400 μg | i.v. | Days 3, 6, 9 |
|  |  | Cisplatin | 3.5 mg/kg | i.p. | Days 0, 7 |
|  |  | ATRi 1 | 60 mg/kg | p.o. | Days 0, 7 |
| 8 | 10 | Avelumab | 400 μg | i.v. | Days 3, 6, 9 |
|  |  | Cisplatin | 3.5 mg/kg | i.p. | Days 0, 7 |
|  |  | ATRi 1 | 60 mg/kg | p.o. | Days 0, 7 |

Note:
[a]N: number of animals per group.

Figure 4:
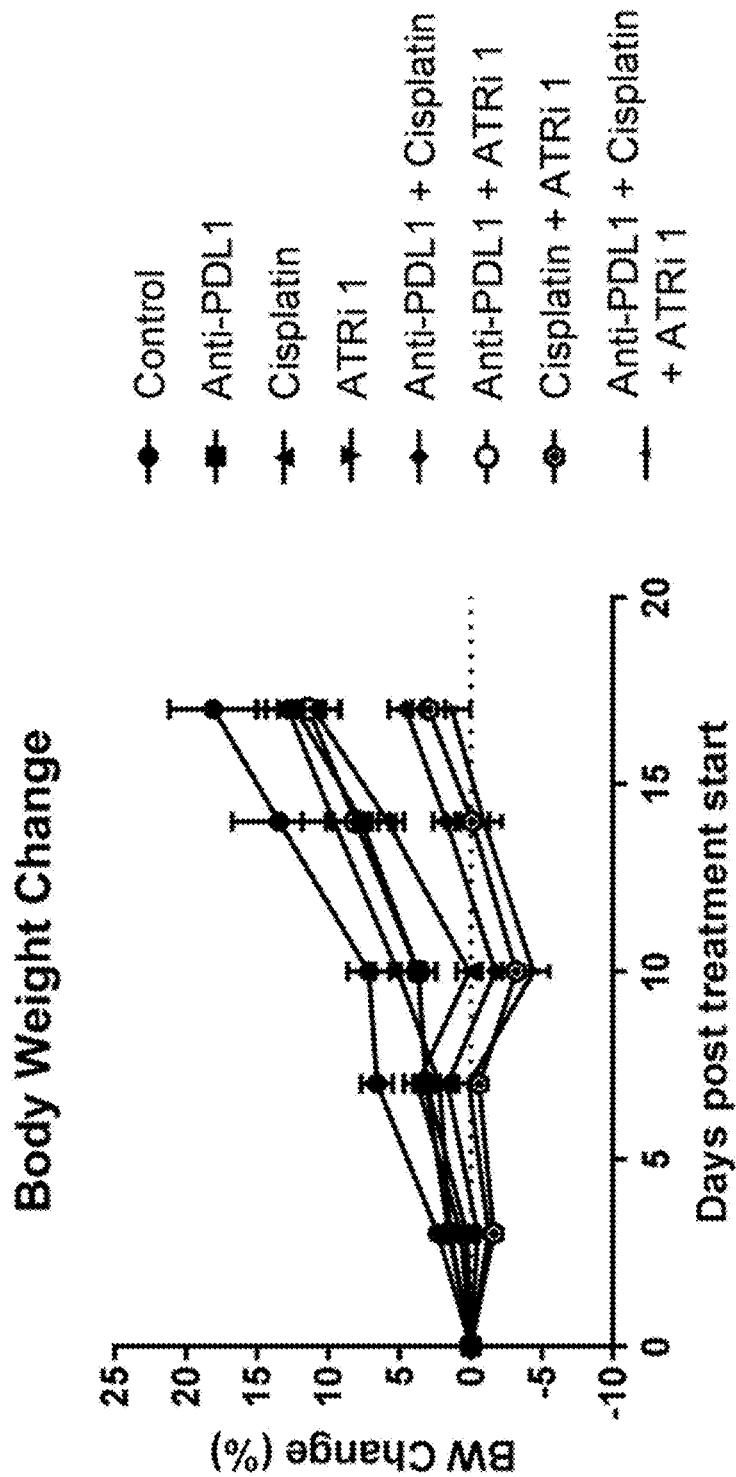
FIG. 4 shows the relative change of body weights (%) of different treatment groups of female C57BL/6 mice bearing MC38 established tumors. Body weight change was calculated based on animal weight on the first day of dosing (DO). Data points represent percent group mean change in body weight. Error bars represent standard error of the mean (SEM). The data is shown up to date 17, after which animals with large tumors were sacrificed and the averages for the study groups affected accordingly.

As an indirect measure of toxicity, the body weight change was monitored, the results of which are shown in FIG. 4.

Figure 5:
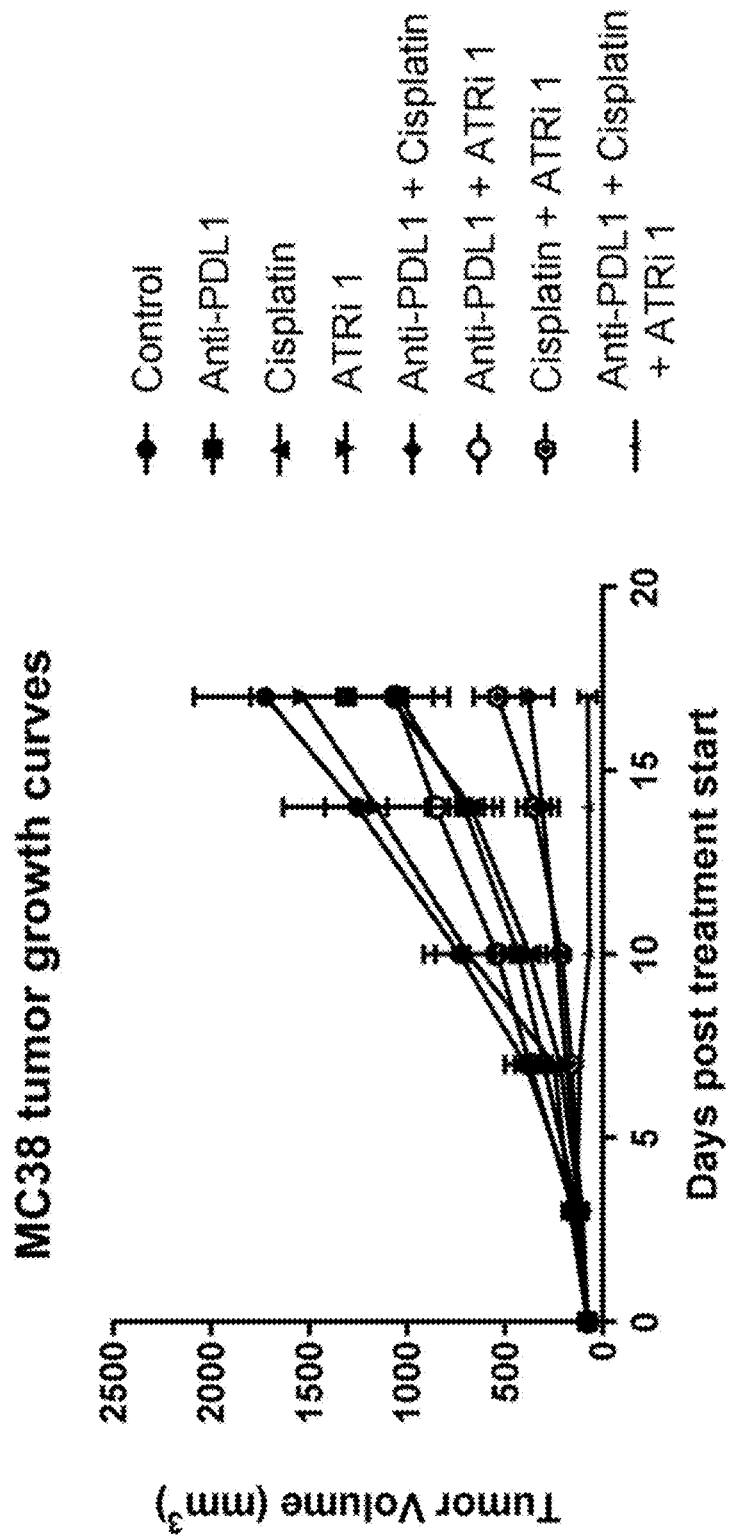
FIG. 5 shows tumor growth curves of different treatment groups of C57BL/6 mice bearing MC38 established tumors. Data points represent group mean, error bars represent standard error of the mean (SEM). The data is shown up to date 17, after which animals with large tumors were sacrificed and the averages for the study groups affected accordingly.

The tumor growth curves of the different mice are shown in FIG. 5 and the tumor growth inhibition at day 17 is shown in the following Table 3.

TABLE 3

Tumor growth inhibition analysis

| Treatment group | Tumor Size (mm$^3$)[a] at day 17 | T/C (%) | TGI % (%) | p value One-way ANOVA |
|---|---|---|---|---|
| 1 | 1725 ± 367 | — | — | — |
| 2 | 1038 ± 250 | 60.2 | 41.8 | 0.773 |
| 3 | 1088 ± 221 | 63.1 | 38.7 | 0.803 |
| 4 | 1534 ± 267 | 88.9 | 11.6 | 1.000 |
| 5 | 380 ± 124 | 22.0 | 81.8 | 0.077 |
| 6 | 1062 ± 274 | 61.6 | 40.3 | 0.823 |
| 7 | 539 ± 123 | 31.2 | 72.1 | 0.139 |
| 8 | 79 ± 46 | 4.6 | 100.1 | 0.026 |

Note:
[a]Mean ± SEM.

The mean tumor size of the Vehicle treated animals reached 1,725 mm$^3$ on day 17 after the start of treatment. Treatment with 400 ug Avelumab as a single agent, 3.5 mg/kg Cisplatin as a single agent, and 60 mg/kg ATRi 1 as a single agent had minor anti-tumor activity; the mean tumor sizes were 1,038 mm$^3$, 1,088 mm$^3$ and 1,534 mm$^3$, respectively, on day 17 (T/C value=60.2%, 63.1% and 88.9%; TGI=41.8%, 38.7% and 11.6%, respectively, p=0.773, 0.803 and 1.000 compared with the Vehicle group).

Dual combination treatment with 400 ug Avelumab and 3.5 mg/kg Cisplatin showed pronounced anti-tumor activity with a mean tumor size of 380 mm$^3$ on day 17 (T/C value=22.0%, TGI=81.8%, p=0.077 compared with Vehicle group). Dual combination treatment with 400 ug Avelumab and 60 mg/kg ATRi 1 showed minor anti-tumor activity with a mean tumor size of 1,062 mm$^3$ on day 17 (T/C value=61.6%, TGI=40.3%, p=0.823 compared with Vehicle group). Dual combination treatment with 3.5 mg/kg Cisplatin and 60 mg/kg ATRi 1 showed pronounced anti-tumor activity with a mean tumor size of 539 mm³ on day 17 (T/C value=31.2%, TGI=72.1%, p=0.139 compared with Vehicle group). The triple combination treatment with 400 ug Avelumab, 3.5 mg/kg Cisplatin and 60 mg/kg ATRi 1 showed the highest anti-tumor activity with a mean tumor size of 79 mm³ on day 17 (T/C value=4.6%, TGI=100.1%, p=0.026 compared with Vehicle group).

Figure 6:
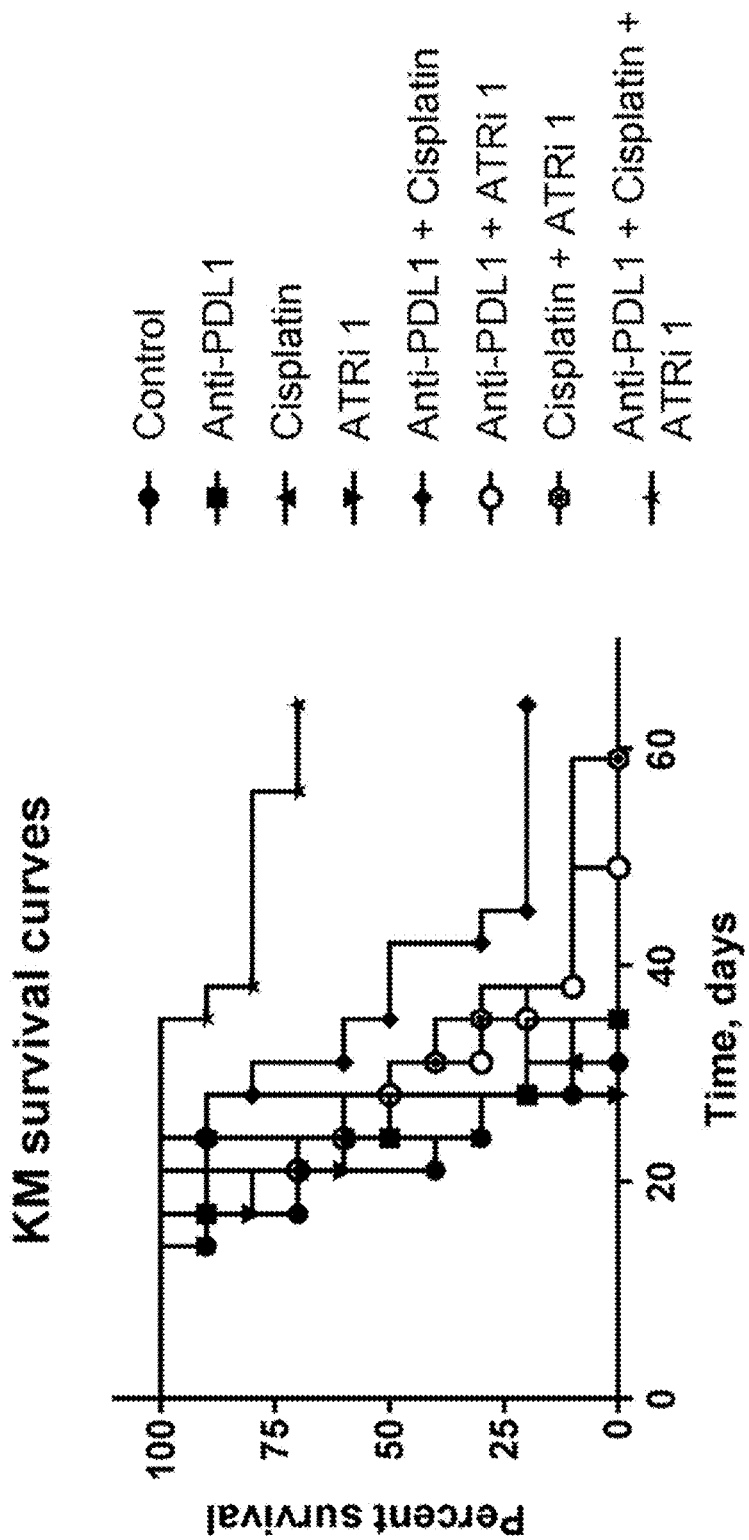
FIG. 6 shows survival curves of different treatment groups of C57BL16 mice bearing MC38 established tumors. Animals were euthanized as they reached a tumor burden of 3,000 mm³.

The survival data is reflected in FIG. 6 and the following Tables 4 and 5.

TABLE 4

Kaplan-Meier survival analysis for triple combination treatment in murine subcutaneous MC38 colorectal cancer syngeneic model calculated based on survival data up to day 66

| Treatment group | Median survival, days | P value for Log-rank test [a] | Tumor-free mice on day 66 |
|---|---|---|---|
| 1 | 21.5 | — | 0/10 |
| 2 | 26 | 0.0753 | 0/10 |
| 3 | 28 | 0.1220 | 0/10 |
| 4 | 24 | 0.9640 | 0/10 |
| 5 | 38.5 | 0.0002 | 2/10 |
| 6 | 29.5 | 0.0272 | 0/10 |
| 7 | 29.5 | 0.0010 | 0/10 |
| 8 | Not reached | <0.0001 | 7/10 |

Note:
[a] Comparisons between groups were carried out with Log-rank test (compared with Vehicle group).

Kaplan-Meier survival analysis for triple combination treatment v.s. each doublet combination treatment based on survival data up to day 66 (Table 5)

| Treatment group | Median survival, days | P value for Log-rank test [a] |
|---|---|---|
| 5 | 38.5 | 0.0150 |
| 6 | 29.5 | <0.0001 |
| 7 | 29.5 | 0.0002 |
| 8 | Not reached | — |

[a] Comparisons between groups were carried out with Log-rank test (compared with triple combination treatment group).

Compared to the Vehicle treated group, the dual combination treatments (Avelumab+Cisplatin; Avelumab+ATRi 1; Cisplatin+ATRi 1) and triple combination treatment (Avelumab+Cisplatin+ATRi 1) significantly prolonged the survival rate of the animals in this study (p=0.0002, 0.0272, 0.0010, <0.0001, respectively, compared with Vehicle group). Compared with each dual combination treatment group (Avelumab+Cisplatin; Avelumab+ATRi 1; Cisplatin+ATRi 1), the triple combination treatment (Avelumab+Cisplatin+ATRi 1) significantly prolonged the survival rate of the animals (p=0.0150, <0.0001, 0.0002, respectively, compared with Triple combination treatment group).

In summary, the Avelumab, Cisplatin, ATRi 1 combination treatment showed high anti-tumor activity in the MC38 colorectal cancer syngeneic model.

Experiment 2B: Triple Combination of Avelumab, Carboplatin and ATRi 1

The anti-tumor efficacy of the triple combination avelumab, carboplatin and ATRi 1 was tested according to the above methods and with the experimental design outlined in Table 6.

Experimental design (Table 6):

| Group | N[a] | Treatment | Dose | Dosing Route | Schedule |
|---|---|---|---|---|---|
| 1 | 10 | Isotype control | 400 µg | i.v. | Days 3, 6, 9 |
|   |   | 0.9% Saline | — | i.p. | Days 0, 7 |
|   |   | Vehicle | — | p.o. | Days 0, 7 |
| 2 | 10 | Avelumab | 400 µg | i.v. | Days 3, 6, 9 |
|   |   | 0.9% Saline | — | i.p. | Days 0, 7 |
|   |   | Vehicle | — | p.o. | Days 0, 7 |
| 3 | 10 | Isotype control | 400 µg | i.v. | Days 3, 6, 9 |
|   |   | Carboplatin | 60 mg/kg | i.p. | Days 0, 7 |
|   |   | Vehicle | — | p.o. | Days 0, 7 |
| 4 | 10 | Isotype control | 400 µg | i.v. | Days 3, 6, 9 |
|   |   | 0.9% Saline | — | i.p. | Days 0, 7 |
|   |   | ATRi 1 | 60 mg/kg | p.o. | Days 0, 7 |
| 5 | 10 | Avelumab | 400 µg | i.v. | Days 3, 6, 9 |
|   |   | Carboplatin | 60 mg/kg | i.p. | Days 0, 7 |
|   |   | Vehicle | — | p.o. | Days 0, 7 |
| 6 | 10 | Avelumab | 400 µg | i.v. | Days 3, 6, 9 |
|   |   | 0.9% Saline | — | i.p. | Days 0, 7 |
|   |   | ATRi 1 | 60 mg/kg | p.o. | Days 0, 7 |
| 7 | 10 | Isotype control | 400 µg | i.v. | Days 3, 6, 9 |
|   |   | Carboplatin | 60 mg/kg | i.p. | Days 0, 7 |
|   |   | ATRi 1 | 60 mg/kg | p.o. | Days 0, 7 |
| 8 | 10 | Avelumab | 400 µg | i.v. | Days 3, 6, 9 |
|   |   | Carboplatin | 60 mg/kg | i.p. | Days 0, 7 |
|   |   | ATRi 1 | 60 mg/kg | p.o. | Days 0, 7 |

Note:
[a] N: number of animals per group.

Figure 7:
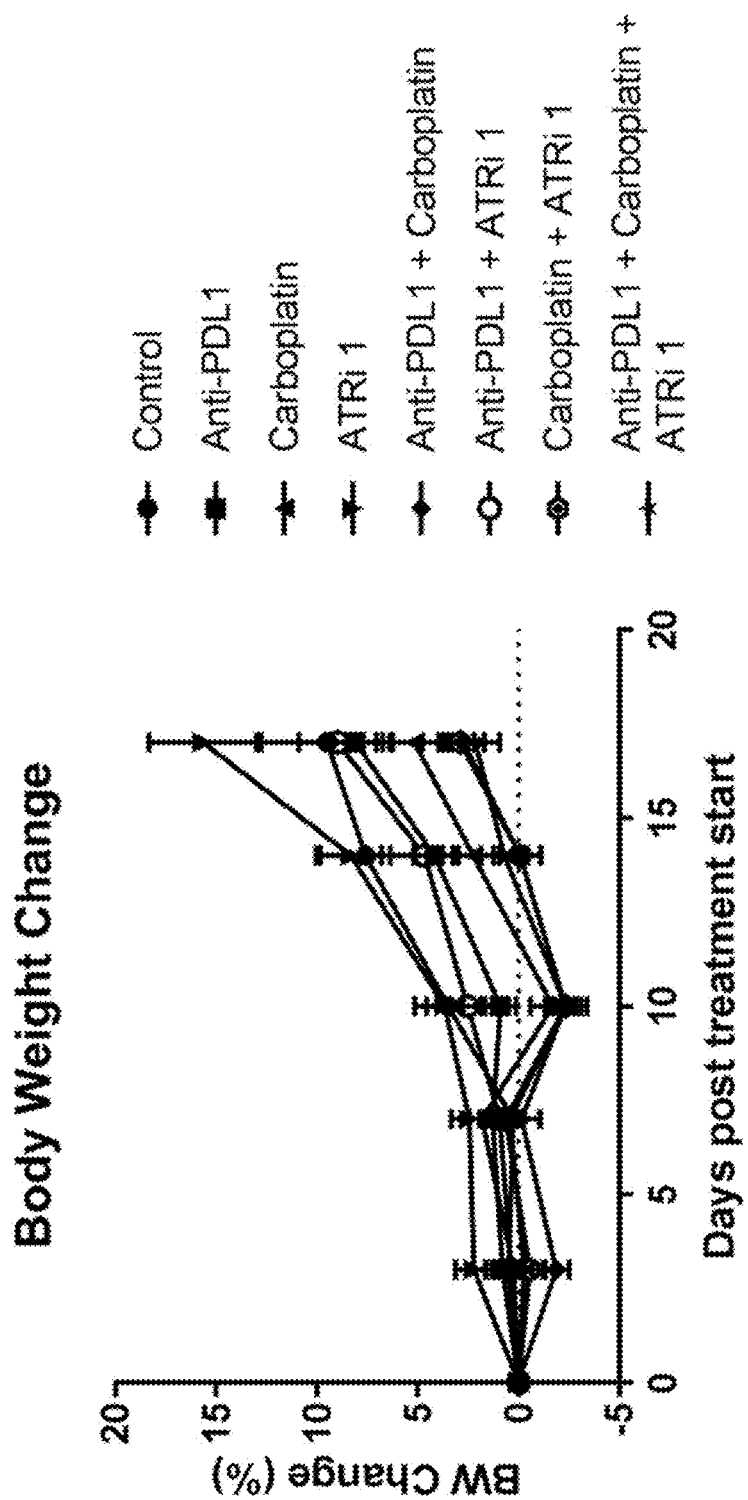
FIG. 7 shows the relative change of body weights (%) of different treatment groups of female C57BL/6 mice bearing MC38 established tumors. Body weight change was calculated based on animal weight on the first day of dosing (DO). Data points represent percent group mean change in body weight. Error bars represent standard error of the mean (SEM). The data is shown up to date 17, after which animals with large tumors were sacrificed and the averages for the study groups affected accordingly.

As an indirect measure of toxicity, the body weight change was monitored, the results of which are shown in FIG. 7.

Figure 8:
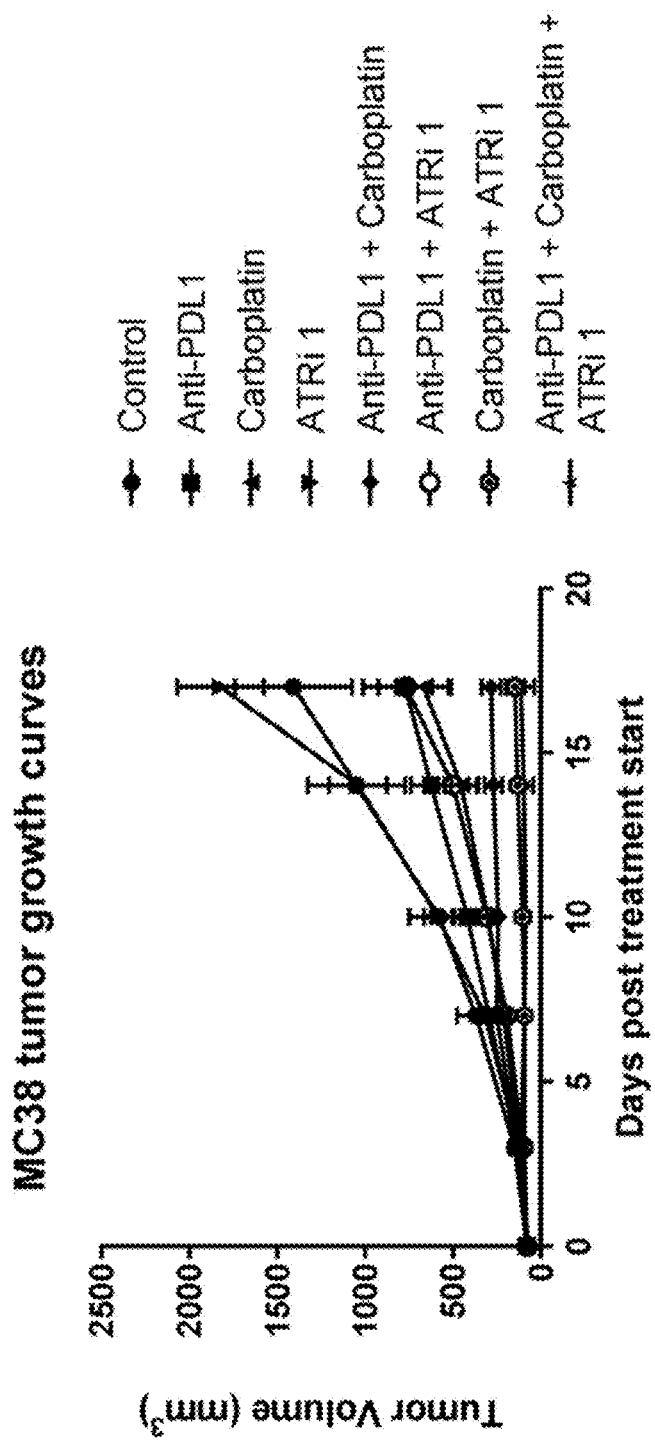
FIG. 8 shows tumor growth curves of different treatment groups of C57BL/6 mice bearing MC38 established tumors. Data points represent group mean, error bars represent standard error of the mean (SEM). The data is shown up to date 17, after which animals with large tumors were sacrificed and the averages for the study groups affected accordingly.

The tumor growth curves of the different mice are shown in FIG. 8 and the tumor growth inhibition at day 17 is shown in the following Table 7.

Tumor growth inhibition analysis (Table 7)

| Treatment group | Tumor Size (mm³)[a] at day 17 | T/C (%) | TGI % (%) | p value One-way ANOVA |
|---|---|---|---|---|
| 1 | 1409 ± 334 | — | — | — |
| 2 | 774 ± 153 | 54.9 | 47.8 | 0.674 |
| 3 | 671 ± 160 | 47.6 | 55.5 | 0.521 |
| 4 | 1824 ± 245 | 129.5 | −31.2 | 0.968 |
| 5 | 284 ± 55 | 20.2 | 84.7 | 0.098 |
| 6 | 769 ± 244 | 54.6 | 48.2 | 0.774 |
| 7 | 149 ± 53 | 10.6 | 94.8 | 0.056 |
| 8 | 115 ± 77 | 8.2 | 97.4 | 0.049 |

Note:
[a] Mean ± SEM.

The mean tumor size of the Vehicle treated animals reached 1,409 mm³ on day 17 after the start of treatment. Treatment with 400 ug Avelumab as a single agent, 60 mg/kg Carboplatin as a single agent, and 60 mg/kg ATRi 1 as a single agent had minor anti-tumor activity; the mean tumor sizes were 774 mm³, 671 mm³ and 1,824 mm³, respectively, on day 17 (T/C value=54.9%, 47.6% and 129.5%; TGI=47.8%, 55.5% and −31.2%, respectively, p=0.674, 0.521 and 0.968 compared with the Vehicle group). Dual combination treatment with 400 ug Avelumab and 60 mg/kg Carboplatin showed pronounced anti-tumor activity with a mean tumor size of 284 mm³ on day 17 (T/C value=20.2%, TGI=84.7%, p=0.098 compared with Vehicle group). Dual combination treatment with 400 ug Avelumab and 60 mg/kg ATRi 1 showed minor anti-tumor activity with a mean tumor size of 769 mm³ on day 17 (T/C value=54.6%, TGI=48.2%, p=0.774 compared with Vehicle group). Dual combination treatment with 60 mg/kg Carboplatin and 60 mg/kg ATRi 1 showed pronounced anti-tumor activity with a mean tumor size of 149 mm$^3$ on day 17 (T/C value=10.6%, TGI=94.8%, p=0.056 compared with Vehicle group). The triple combination treatment with 400 ug Avelumab, 60 mg/kg Carboplatin and 60 mg/kg ATRi 1 showed the highest anti-tumor activity with a mean tumor size of 115 mm$^3$ on day 17 (T/C value=8.2%, TGI=97.4%, p=0.049 compared with Vehicle group).

Figure 9:
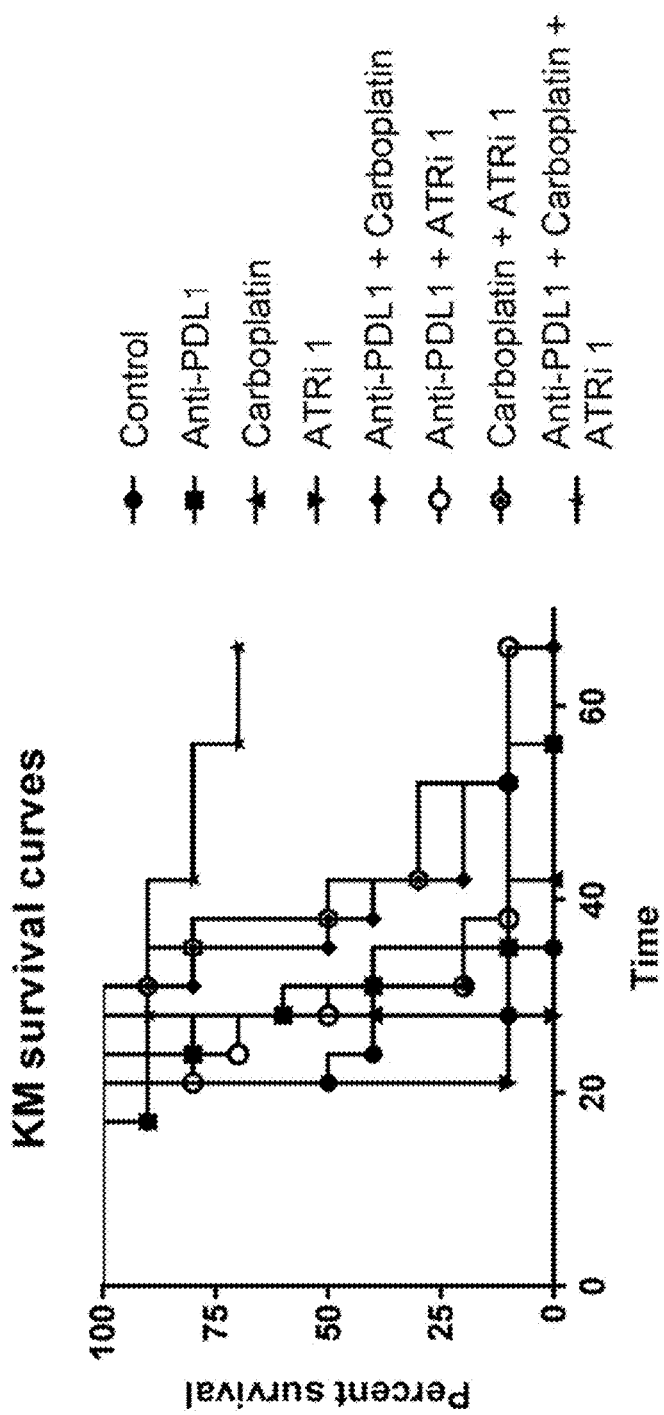
FIG. 9 shows survival curves of different treatment groups of C57BL/6 mice bearing MC38 established tumors. Animals were euthanized as they reached a tumor burden of 3,000 mm³.

The survival data is reflected in FIG. 9 and the following Tables 8 and 9.

Kaplan-Meier survival analysis for triple combination treatment in murine subcutaneous MC38 colorectal cancer syngeneic model calculated based on survival data up to day 66 (Table 8)

| Treatment group | Median survival, days | P value for Log-rank test [a] | Tumor-free mice on day 66 |
|---|---|---|---|
| 1 | 22.5 | | 0/10 |
| 2 | 31 | 0.0196 | 0/10 |
| 3 | 28 | 0.0450 | 0/10 |
| 4 | 21 | 0.1425 | 0/10 |
| 5 | 36.5 | 0.0001 | 0/10 |
| 6 | 29.5 | 0.0586 | 1/10 |
| 7 | 41.5 | <0.0001 | 1/10 |
| 8 | Not reached | <0.0001 | 7/10 |

Note:
[a] Comparisons between groups were carried out with Log-rank test (compared with Vehicle group).

Kaplan-Meier survival analysis for triple combination treatment v.s. each doublet combination treatment based on survival data up to day 66 (Table 9)

| Treatment group | Median survival, days | P value for Log-rank test [a] |
|---|---|---|
| 5 | 36.5 | 0.0008 |
| 6 | 29.5 | 0.0013 |
| 7 | 41.5 | 0.0054 |
| 8 | Not reached | — |

[a] Comparisons between groups were carried out with Log-rank test (compared with triple combination treatment group).

Compared to the Vehicle treated group, the dual combination treatments (Avelumab+Carboplatin; Avelumab+ATRi 1; Carboplatin+ATRi 1) and triple combination treatment (Avelumab+Carboplatin+ATRi 1) significantly prolonged the survival rate of the animals in this study (p=0.0001, <0.0001, <0.0001, respectively, compared with Vehicle group). Compared with each dual combination treatment group (Avelumab+Carboplatin; Avelumab+ATRi 1; Carboplatin+ATRi 1), the triple combination treatment (Avelumab+Carboplatin+ATRi 1) significantly prolonged the survival rate of the animals (p=0.0008, 0.0013, 0.0054, respectively, compared with Triple combination treatment group).

In summary, the Avelumab, Carboplatin, ATRi 1 combination treatment showed high anti-tumor activity in the MC38 colorectal cancer syngeneic model.

Example 3: Re-Challenge Study in MC38 Model

The objective of the re-challenge study was to test whether the surviving animals from the efficacy study of Example 2 had acquired protective immunity against the same tumor.

Example 3A: Triple Combination of Avelumab, Cisplatin and ATRi 1

In this study, the surviving animals from Group 5 (Avelumab, 400 ug+Cisplatin, 3.5 mg/kg+Vehicle) and Group 8 (Avelumab, 400 ug+Cisplatin, 3.5 mg/kg+ATRi 1, 60 mg/kg) were re-challenged with 3×10$^5$ MC38 cells on day 67 after the first MC38 inoculation (Table 10). The cells were injected into the left flank of the animals.

Experimental design (Table 10)

| Treatment Group according to Example 2A | n[a] | Cell line | Cell number/mouse | Injection volume |
|---|---|---|---|---|
| Naive mice | 10 | MC38 | 3 × 10$^5$ | 100 μl |
| 5 | 2 | | 3 × 10$^5$ | 100 μl |
| 8 | 7 | | 3 × 10$^5$ | 100 μl |

Note:
[a] N: number of animals per group.

The tumor growth was monitored over 3 weeks after implantation and tumor volumes are shown in the following Table 11:

Tumor growth data (Table 11)

| | Tumor volume (mm$^3$)[a] | | |
|---|---|---|---|
| Days | Untreated mice | Treatment group 5 | Treatment group 8 |
| 0 | 0 ± 0 | 0 ± 0 | 0 ± 0 |
| 7 | 182 ± 14 | 0 ± 0 | 0 ± 0 |
| 11 | 346 ± 49 | 0 ± 0 | 0 ± 0 |
| 14 | 740 ± 113 | 0 ± 0 | 0 ± 0 |
| 18 | 1337 ± 167 | 0 ± 0 | 0 ± 0 |
| 21 | 2162 ± 336 | 0 ± 0 | 0 ± 0 |

Note:
[a] Mean ± SEM

The mean tumor size of the control naive mice reached 2,162 mm$^3$ at day 21 after tumor implantation. No tumor growth was found on the complete responders from Group 5 and Group 8 after MC38 re-challenge during the entire study.

In summary, the surviving animals appear to have acquired protective immunity against the same tumor.

Example 3B: Triple Combination of Avelumab, Carboplatin and ATRi 1

In this study, the surviving animals from Group 6 (Avelumab, 400 ug+0.9% Saline+ATRi 1, 60 mg/kg), Group 7 (Isotype control, 400 ug+Carboplatin, 60 mg/kg+ATRi 1, 60 mg/kg) and Group 8 (Avelumab, 400 ug+Carboplatin, 60 mg/kg+ATRi 1, 60 mg/kg) were re-challenged with 3×10$^5$ MC38 cells on day 67 after the first MC38 inoculation (Table 12). The cells were injected into the left flank of the animals.

Experimental design (Table 12)

| Treatment Group according to Example 2B | n[a] | Cell line | Cell number/mouse | Injection volume |
|---|---|---|---|---|
| Naive mice | 10 | MC38 | 3 × 10$^5$ | 100 μl |
| 6 | 1 | | 3 × 10$^5$ | 100 μl |
| 7 | 1 | | 3 × 10$^5$ | 100 μl |
| 8 | 7 | | 3 × 10$^5$ | 100 μl |

Note:
[a] N: number of animals per group.

The tumor growth was monitored over 3 weeks after implantation and tumor volumes are shown in the following Table 13:

Tumor growth data (Table 13)

| Days | Untreated mice | Treatment group 6 | Treatment group 7 | Treatment group 8 |
|---|---|---|---|---|
| 0 | 0 ± 0 | 0 | 0 | 0 ± 0 |
| 7 | 182 ± 14 | 0 | 0 | 0 ± 0 |
| 11 | 346 ± 49 | 0 | 0 | 0 ± 0 |
| 14 | 740 ± 113 | 0 | 0 | 0 ± 0 |
| 18 | 1337 ± 167 | 0 | 0 | 0 ± 0 |
| 21 | 2162 ± 336 | 0 | 0 | 0 ± 0 |

Tumor volume ($mm^3$)[a]

Note:
[a] Mean ± SEM

The mean tumor size of the control naive mice reached 2,162 $mm^3$ at day 21 after tumor implantation. No tumor growth was found on the complete responders from Groups 6, 7 and 8 after MC38 re-challenge during the entire study.

In summary, the surviving animals appear to have acquired protective immunity against the same tumor.

Example 4: In Vivo Test of Anti-Tumor Efficacy of a Triple Combination Treatment in Murine Subcutaneous MB49 Tumor Model The objective of this study was to investigate the therapeutic efficacy of carboplatin, ATRi 1 (Compound 1) and the anti-PD-L1 antibody avelumab in MB49 syngeneic tumor model.

Tumor Inoculation and Animal Grouping

C57BL/6 female mice at 8-9 weeks of age where subcutaneously injected into the right flank with 0.5×10⁶ of viable MB49 tumor cells in 0.1 mL PBS. The animals were randomized and therapy initiated when the tumors reached a volume of around 100 $mm^3$ (day 0 of treatment). Each group consisted of 10 tumor-bearing mice. The tested compounds were administered to the mice according to the predetermined regimen shown in the experimental design Table 14:

Experimental design (Table 14):

| Group | N[a] | Treatment | Dose | Dosing Route | Schedule |
|---|---|---|---|---|---|
| 1 | 10 | Isotype control | 400 μg | i.v. | Days 3, 6, 9 |
|   |    | 0.9% Saline | — | i.p. | Days 0, 7 |
|   |    | Vehicle | — | p.o. | Days 0, 7 |
| 2 | 10 | Avelumab | 400 μg | i.v. | Days 3, 6, 9 |
|   |    | 0.9% Saline | — | i.p. | Days 0, 7 |
|   |    | Vehicle | — | p.o. | Days 0, 7 |
| 3 | 10 | Isotype control | 400 μg | i.v. | Days 3, 6, 9 |
|   |    | Carboplatin | 60 mg/kg | i.p. | Days 0, 7 |
|   |    | Vehicle | — | p.o. | Days 0, 7 |
| 4 | 10 | Isotype control | 400 μg | i.v. | Days 3, 6, 9 |
|   |    | 0.9% Saline | — | i.p. | Days 0, 7 |
|   |    | ATRi 1 | 60 g mg/k | p.o. | Days 0, 7 |
| 5 | 10 | Avelumab | 400 μg | i.v. | Days 3, 6, 9 |
|   |    | Carboplatin | 60 mg/kg | i.p. | Days 0, 7 |
|   |    | Vehicle | — | p.o. | Days 0, 7 |
| 6 | 10 | Avelumab | 400 μg | i.v. | Days 3, 6, 9 |
|   |    | 0.9% Saline | — | i.p. | Days 0, 7 |
|   |    | ATRi 1 | 60 mg/kg | p.o. | Days 0, 7 |
| 7 | 10 | Isotype control | 400 μg | i.v. | Days 3, 6, 9 |
|   |    | Carboplatin | 60 mg/kg | i.p. | Days 0, 7 |
|   |    | ATRi 1 | 60 mg/kg | p.o. | Days 0, 7 |
| 8 | 10 | Avelumab | 400 μg | i.v. | Days 3, 6, 9 |
|   |    | Carboplatin | 60 mg/kg | i.p. | Days 0, 7 |
|   |    | ATRi 1 | 60 mg/kg | p.o. | Days 0, 7 |

The antibodies and carboplatin were dissolved in 0.9% saline and ATRi 1 in 0.5% Methocel K4M Premium/0.25% Tween 20 (also referred to as Vehicle).

Tumor Measurements and Endpoints

Tumor size was measured twice a week and the tumor volume determined using the formula width×length×height×0.5236. The tumor size was then used for calculation of T/C values.

The body weight was also measured twice a week. Mice were sacrificed when the tumor volume reached 2000 $mm^3$.

Statistical Analysis

One-way analysis of variance (ANOVA) with Bonferroni's Multiple Comparisons Test, two-way ANOVA, unpaired t-test and Log-rank test from the GraphPad Prism software package were used (Prism 5 for Windows, Version 5.0, GraphPad Software Inc., San Diego, CA). $p<0.05$ was considered to be statistically significant.

Results

Figure 10:
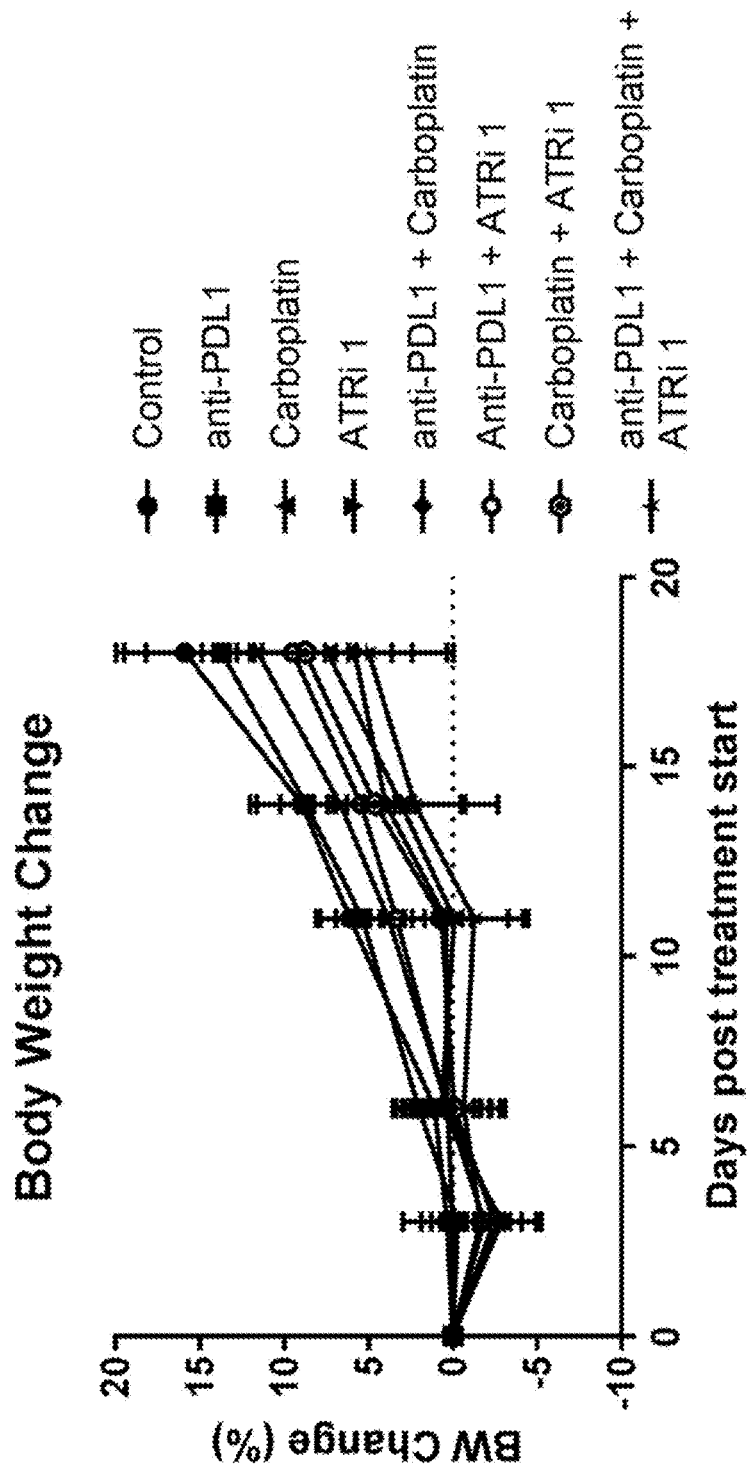
FIG. 10 shows the relative change of body weights (%) of different groups of female C57BL/6 mice re-challenged with MB49. The change was calculated based on the animal weight on the first day of cell inoculation. Data points represent percent group mean change in body weight. Error bars represent standard error of the mean (SEM).

As an indirect measure of toxicity, the body weight change was monitored, the results of which are shown in FIG. 10.

Figure 11:
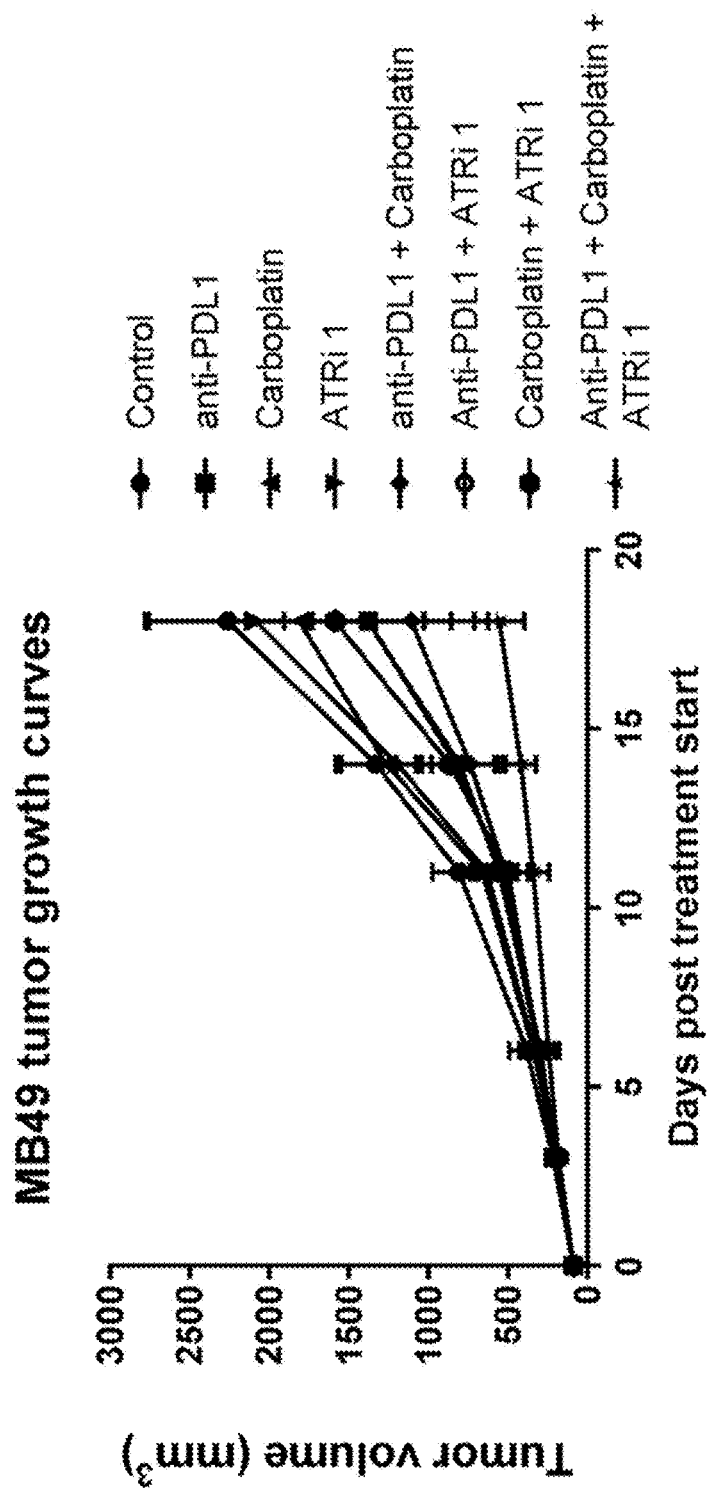
FIG. 11 shows tumor growth curves of different groups of female C57BL/6 mice re-challenged with MB49. Data points represent group mean, error bars represent standard error of the mean (SEM).

The tumor growth curves of the different mice are shown in FIG. 11 and the tumor growth inhibition at day 18 is shown in the following Table 15.

Tumor growth inhibition analysis (Table 15)

| Treatment group | Tumor Size ($mm^3$)[a] at day 18 | TGI % (%) | p value One-way ANOVA |
|---|---|---|---|
| 1 | 2264 ± 256 | — | — |
| 2 | 1378 ± 175 | 39.1 | 0.0264 |
| 3 | 1814 ± 212 | 19.9 | 0.5195 |
| 4 | 2087 ± 333 | 7.8 | 0.99 |
| 5 | 1108 ± 239 | 51.1 | 0.0018 |
| 6 | 1385 ± 259 | 38.8 | 0.0279 |
| 7 | 1588 ± 276 | 29.9 | 0.1405 |
| 8 | 556 ± 79 | 75.5 | 0.0001 |

Note:
[a] Mean ± SEM.

Figure 12:
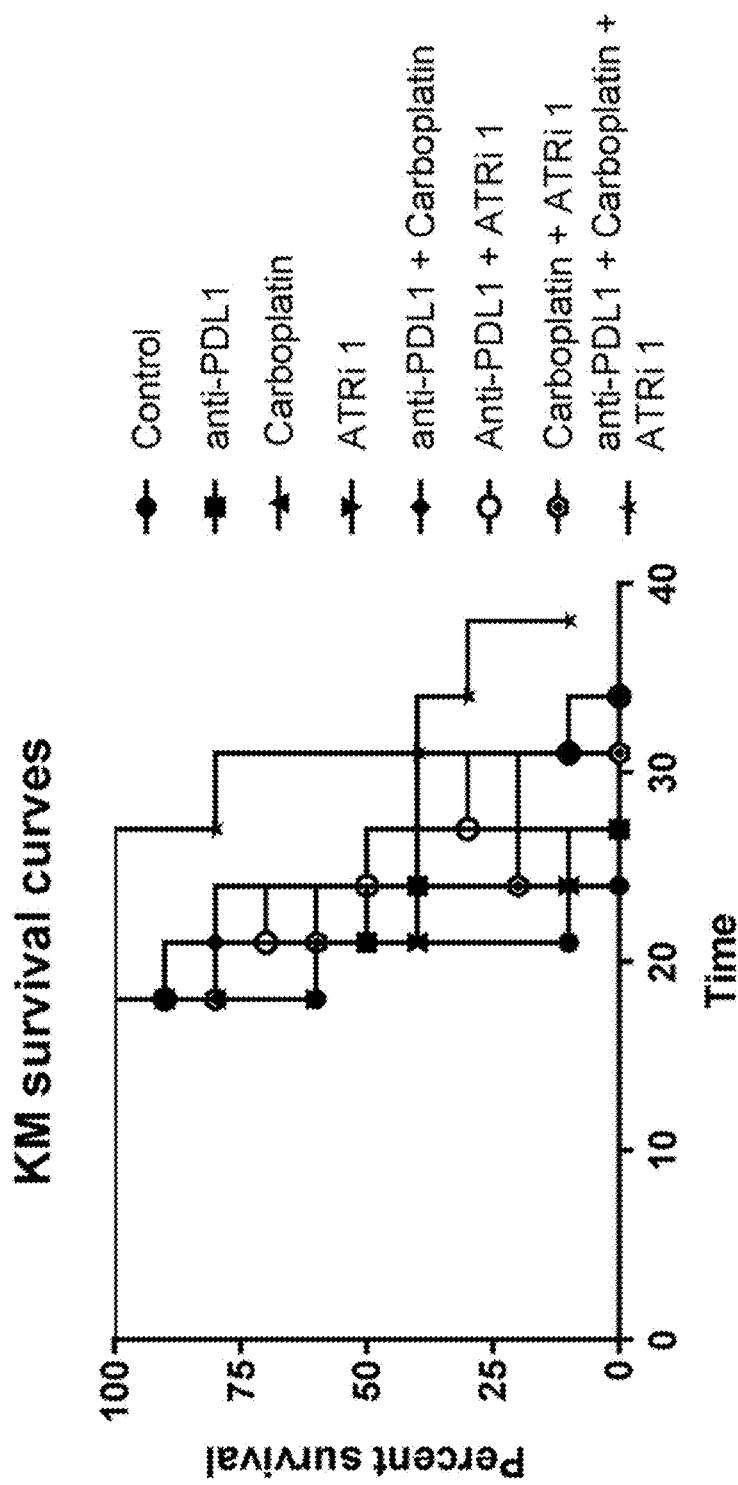
FIG. 12 shows survival curves of different treatment groups of C57BL/6 mice bearing MB49 established tumors. Animals were euthanized as they reached a tumor burden of 2,000 mm$^3$.

The survival data is reflected in FIG. 12 and the following Tables 16 and 17.

Kaplan-Meier survival analysis for triple combination treatment in murine subcutaneous MB49 model calculated based on survival data (Table 16)

| Treatment group | Median survival, days | P value for Log-rank test[a] |
|---|---|---|
| 1 | 21 | — |
| 2 | 22.5 | 0.0146 |
| 3 | 21 | 0.107 |
| 4 | 21 | 0.2537 |
| 5 | 24 | 0.002 |
| 6 | 25.5 | 0.0034 |
| 7 | 24 | 0.0279 |
| 8 | 31 | <0.0001 |

Note:
[a] Comparisons between groups were carried out with Log-rank test (compared with Vehicle group).

Kaplan-Meier survival analysis for triple combination treatment v.s. each doublet combination treatment based on survival data (Table 17)

| Treatment group | Median survival, days | P value for Log-rank test[a] |
|---|---|---|
| 5 | 24 | 0.0151 |
| 6 | 25.5 | 0.0081 |

-continued

Kaplan-Meier survival analysis for triple combination treatment v.s. each doublet combination treatment based on survival data (Table 17)

| Treatment group | Median survival, days | P value for Log-rank test [a] |
|---|---|---|
| 7 | 24 | 0.001 |
| 8 | 31 | — |

[a] Comparisons between groups were carried out with Log-rank test (compared with triple combination treatment group).

In this study carboplatin monotherapy or ATRi 1 monotherapy did not show any significant tumor growth inhibition effect compared to the control group (based on TGI calculations at day 18 after start of treatment, Table 15; and based on analysis of Kaplan-Meier survival curves, Table 16).

Combination of Carboplatin+ATRi 1 showed a moderate effect on tumor growth on day 18 after start of treatment (TGI=29.9% vs control group, p=0.1405, Table 15), resulting in a significant increase in median survival (24 vs 21 days for control group, p=0.0279, Table 16).

Avelumab as a monotherapy showed a moderate tumor growth inhibition effect (TGI=39.1% vs control group, p=0.0264) which resulted in an increase in median survival compared to the control group (22.5 vs 21 days, p=0.0146). Combination of Avelumab with either Carboplatin or ATRi 1 also showed significant effect on tumor growth (day 18 TGI=51.1% and 38.8% vs control group, p=0.0018 and p=0.0279, respectively, Table 15) and prolonged median survival compared to the control group (24 and 25.5 vs 21 days, Table 16).

Triple combination of Carboplatin/ATRi 1/Avelumab showed potent anti-tumor effect in this study and was significantly better compared to any of the doublets (Carboplatin/ATRi 1, Carboplatin/Avelumab or ATRi 1/Avelumab) using TGI calculations for day 18 (TGI of 75.5% vs 29.9%, 51.1% and 38.8% correspondingly) and by analysis of Kaplan-Meier survival curves (median survival 31 days vs 24, 24 and 25.5 days correspondingly, P-values for the triplet vs doublets comparison shown in Table 17).

In summary, the tumor growth inhibition data with the triple combination of carboplatin, ATRi 1 and Avelumab demonstrated superior benefit over doublet combination treatments.

Example 5: In Vitro and In Vivo Gene Expression Profiling

The objective of this study was to identify gene sets that differ between treatment groups and control groups.

Preparation of In Vitro Samples

MC38 murine cancer cells were treated with vehicle, ATRi (110 nM), Carboplatin (10 µM) or ATRi (110 nM)+Carboplatin (10 µM) for 24 h, 48 h or 72 hours. At the end of each treatment, time point), the majority of tumor cells were viable as determined by Cell Titer-Glo (Promega, Cat #G7573). RNA extraction was performed using a Qiagen kit (Qiagen, Cat #74104).

Preparation of In Vivo Samples

Cell Culture

The MC38 tumor cells were maintained in vitro as a monolayer culture in DMEM+2 mM glutamine supplemented with 10% heat inactivated fetal bovine serum, 100 U/ml penicillin and 100 µg/ml streptomycin at 37° C. in an atmosphere of 5% $CO_2$ in air. The tumor cells were routinely sub cultured twice weekly by trypsin-EDTA treatment. The cells growing in an exponential growth phase were harvested and counted for tumor inoculation.

Tumor Inoculation and Animal Grouping

Each mouse was inoculated subcutaneously at the right upper flank with MC38 cells ($3 \times 10^1$) in 0.1 mL of PBS for tumor development. The animals were assigned into groups using an Excel-based randomization software performing stratified randomization based upon their tumor volumes when the average tumor size reached approximately 150 $mm^3$ (day 0). Each group consisted of 5 tumor-bearing mice. The tested compounds were administered to the mice according to the predetermined regimen shown in the experimental design Table 19.

Tested compounds (Table 18)

| Tested compounds | Solvent |
|---|---|
| Avelumab | PBS |
| Isotype control | PBS |
| Carboplatin | 0.9% Saline |
| ATRi 1 | 0.5% Methocel K4M Premium/0.25% Tween 20 (solvent also referred to as Vehicle) |

Experimental design (Table 19):

| Group | Animals per group | Treatment | Dose | Dosing Route | Schedule |
|---|---|---|---|---|---|
| 1 | 5 | Isotype control | 400 µg | i.v. | Day 0 |
|   |   | 0.9% Saline | — | i.p. | Day 1 |
|   |   | Vehicle | — | p.o. | Day 1 |
| 2 | 5 | Avelumab | 400 µg | i.v. | Day 0 |
|   |   | 0.9% Saline | — | i.p. | Day 1 |
|   |   | Vehicle | — | p.o. | Day 1 |
| 3 | 5 | Isotype control | 400 µg | i.v. | Day 0 |
|   |   | Carboplatin | 60 mg/kg | i.p. | Day 1 |
|   |   | Vehicle | — | p.o. | Day 1 |
| 4 | 5 | Avelumab | 400 µg | i.v. | Day 0 |
|   |   | Carboplatin | 60 mg/kg | i.p. | Day 1 |
|   |   | Vehicle | — | p.o. | Day 1 |
| 5 | 5 | Avelumab | 400 µg | i. v. | Day 0 |
|   |   | Carboplatin | 60 mg/kg | i.p. | Day 1 |
|   |   | ATRi 1 | 60 mg/kg | p.o. | Day 1 |

On day 3 post randomization animals were sacrificed and tumor samples collected in RNALater buffer. RNA extraction was performed using a Qiagen kit (Qiagen, Cat #74104).

RNAseq Generation and Analysis of Gene Expression

RNA-Seq of the above in vitro and in vivo RNA samples was performed. Each sample had 30-50 million usable reads that aligned to the genome. Expression profiles was normalized and transformed with the limma-voom method. mSigDB gene sets and immune signatures were utilized to understand differences in tumor hallmarks, canonical pathways and immune cell content differences.

Results

Figure 13A:
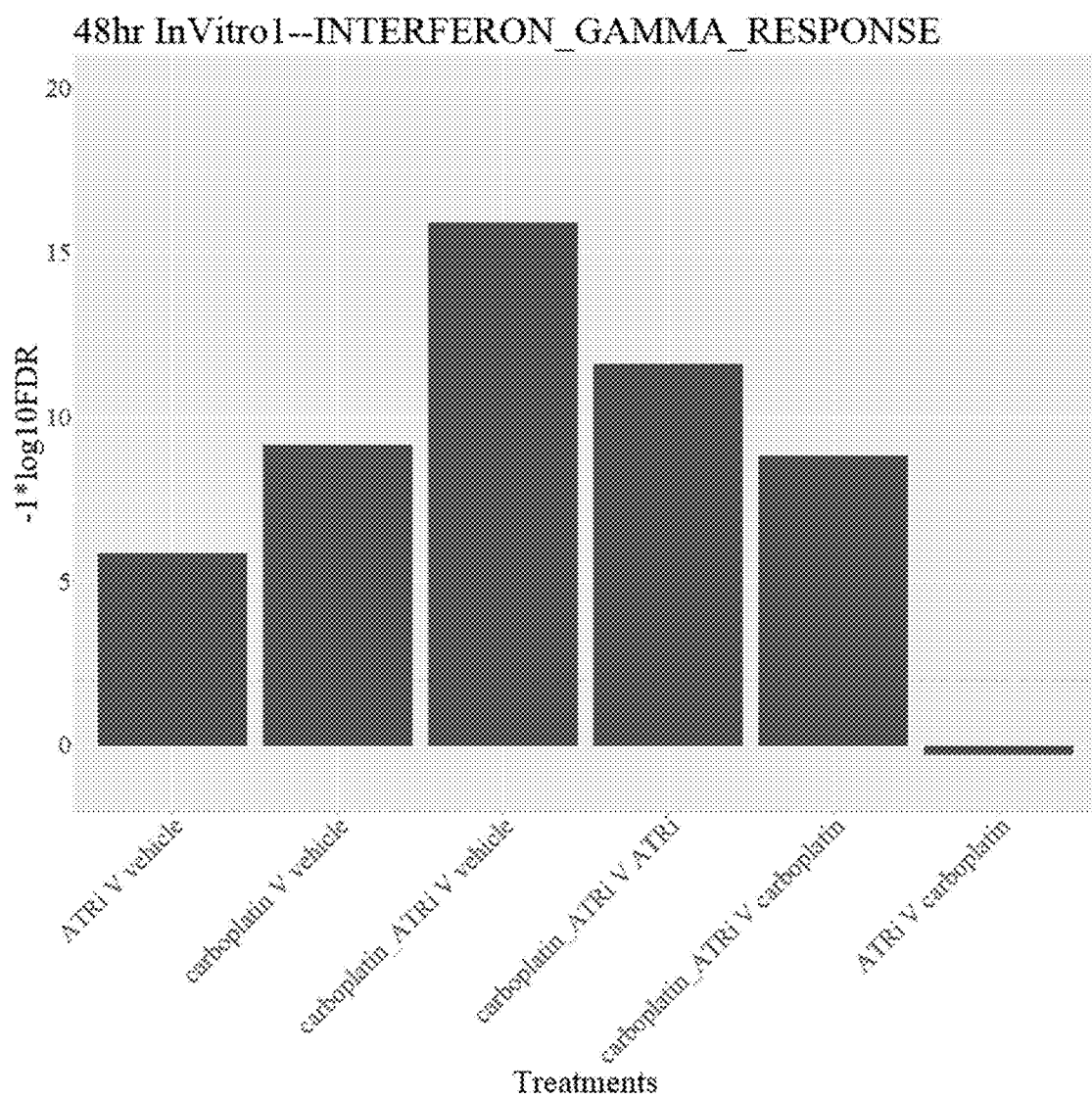
FIGS. 13A and 13B show the modulation of IFN gamma (FIG. 13A) and alpha/beta (FIG. 13B) pathways in vitro—ATRi/Carboplatin combination treatment versus vehicle or single agent at 48 hours.
Figure 13B:
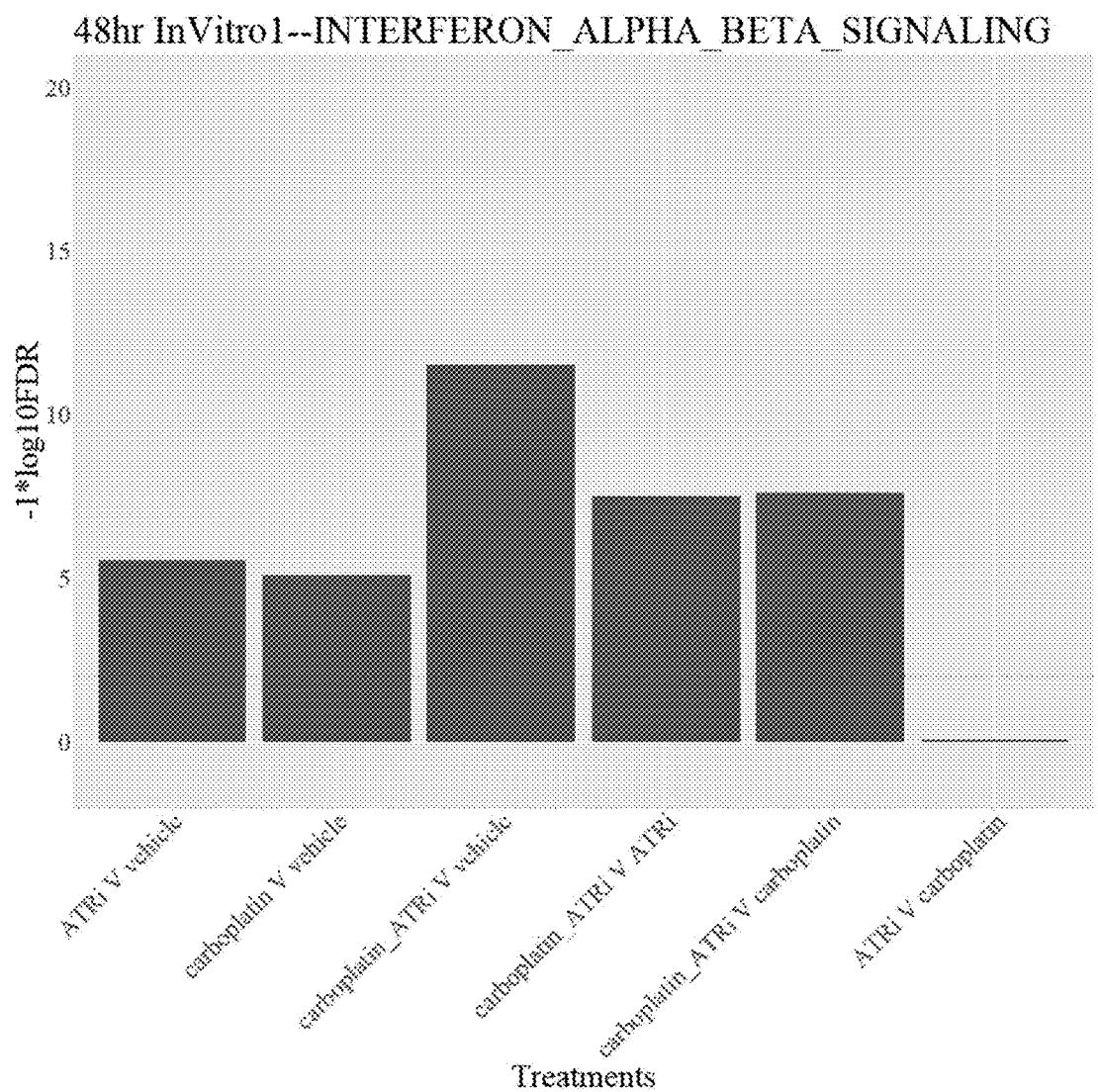

In vitro, it was found that ATRi+Carboplatin treatment robustly enhanced Interferon (IFN) gamma and IFN alpha/beta pathways compared to the single agent or vehicle (FIG. 13a, b). This effect was maximal at 48 hours.

Figure 14A:
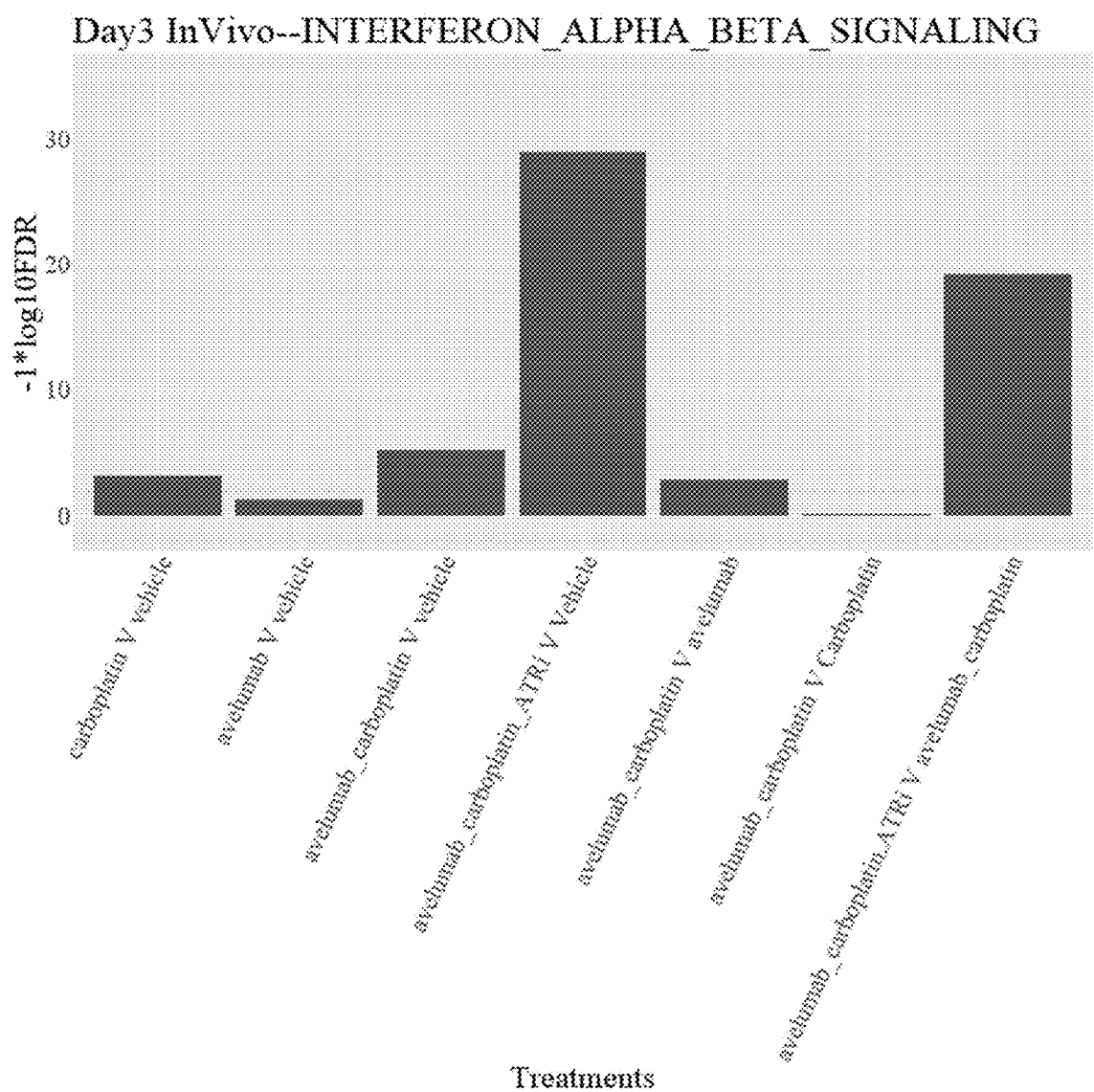
FIGS. 14A and 14B show the modulation of alpha/beta (FIG. 14A) and IFN gamma (FIG. 14B) pathways in vivo—ATRi/Carboplatin/Avelumab combination treatment versus single agent or doublet after 3 days of treatment.
Figure 14B:
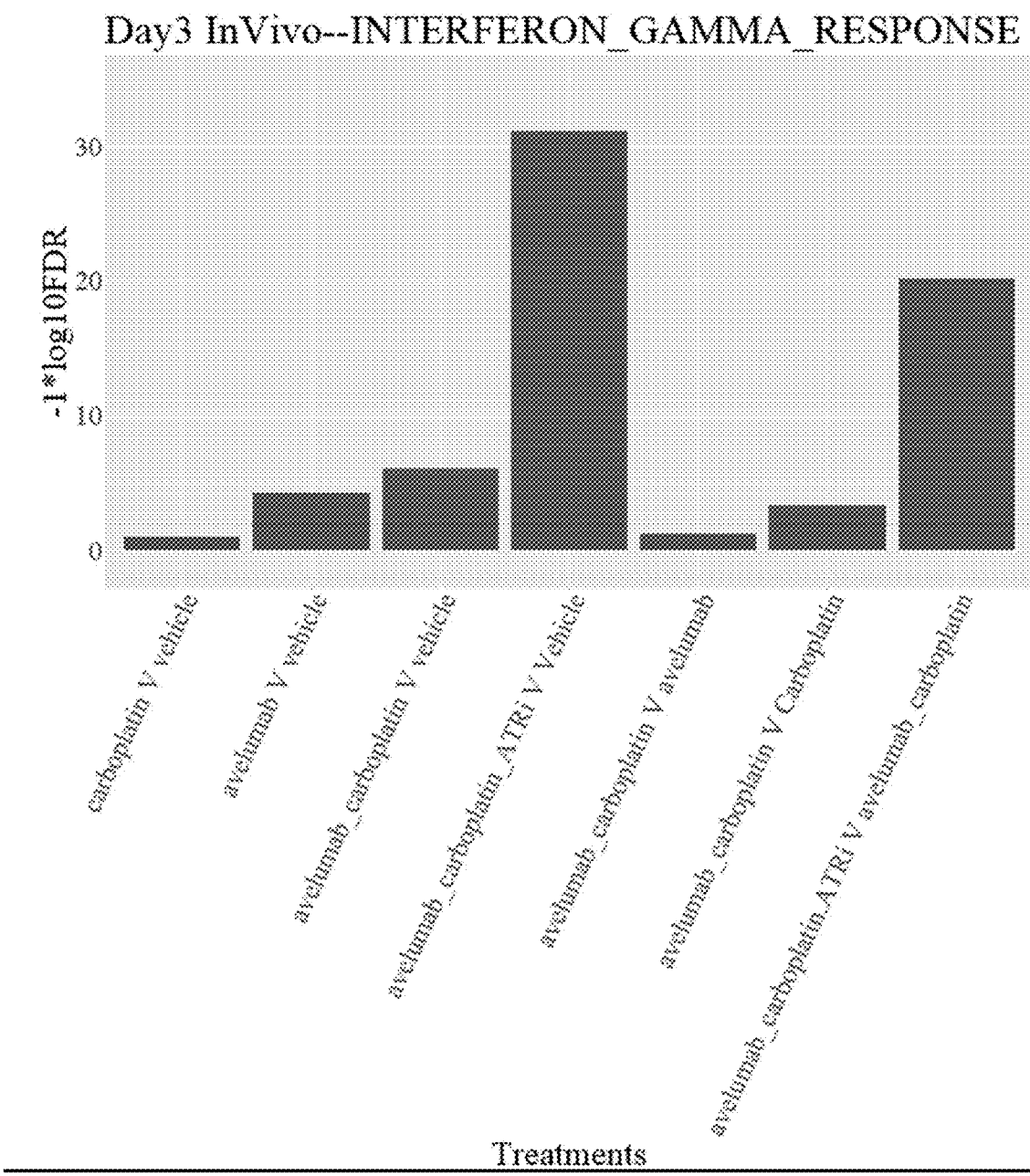

These pathways were examined at day 3 and day 6 in vivo, in tumor mice bearing treated with mono, double or triple therapies of avelumab, carboplatin and ATRi. Similarly, we observed that ATRi+Carboplatin+Avelumab triple combination treatment strongly enhanced the IFN gamma and IFNalpha/beta pathways as compared to vehicle, the single agent or doublet treatment (FIG. 14a, b).

In conclusion, two independent in vitro and in vivo studies demonstrated that the treatment effect of a platinating agent on IFN-γ-related gene mRNA levels in cancer cells is greatly and further enhanced when it is combined with an ATRi drug agent. In addition, we observed that IFN-γ-related gene mRNA levels were further increased when the two drugs, platinating agent+ATRi, were combined with the anti-PDL1 mAb Avelumab. Activation of IFN signaling has been positively correlated with clinical outcome and positive response to PDx therapies. In this context, the robust positive regulation of IFN by ATRi+platinating agent+Avelumab compared to platinating agent+Avelumab strongly supports the potential of the triplet combination benefit versus the doublet observed in the MC38 tumor model.

The invention claimed is:

1. A method of treating cancer in a subject in need thereof, the method comprising administering to the subject a PD-1 antagonist, an ATR inhibitor and a platinating agent,
wherein the PD-1 antagonist is selected from the group consisting of avelumab, nivolumab, pembrolizumab, atezolizumab, durvalumab and cemiplimab, and
wherein the ATR inhibitor is selected from the group consisting of Compound 1, or a pharmaceutically acceptable salt thereof, Compound 2, or a pharmaceutically acceptable salt thereof, Compound 3, or a pharmaceutically acceptable salt thereof, Compound 4, or a pharmaceutically acceptable salt thereof, and Compound 5, or a pharmaceutically acceptable salt thereof.

2. The method of claim 1, wherein the PD-1 antagonist is an anti-PD-L1 antibody, or an antigen-binding fragment thereof, comprising a heavy chain, which comprises three complementarity determining regions having amino acid sequences of SEQ ID NOs: 1, 2 and 3, and a light chain, which comprises three complementarity determining regions having amino acid sequences of SEQ ID NOs: 4, 5 and 6.

3. The method of claim 1, wherein the platinating agent is selected from the group consisting of cisplatin, carboplatin and oxaliplatin.

4. The method of claim 1, wherein the PD-1 antagonist is avelumab, the ATR inhibitor is Compound 1, or a pharmaceutically acceptable salt thereof, and the platinating agent is carboplatin.

5. The method of claim 1, wherein the cancer is selected from the group consisting of cancer of lung, head and neck, colon, urothelium, prostate, esophagus, bladder, stomach, neuroendocrine system, mesenchyme, breast, ovarian, primary peritoneal, fallopian tube, pancreas, and histological subtypes thereof.

6. The method of claim 5, wherein the cancer is a PARPi-resistant recurrent cancer selected from the group consisting of ovarian cancer, primary peritoneal cancer, and fallopian tube cancer.

7. The method of claim 1, wherein the PD-1 antagonist is avelumab and administered Q3W with a dosage of about 1600 mg, the platinating agent is carboplatin and administered Q3W at a dosage with a target AUC of about 5 mg/mL·min and the ATR inhibitor is Compound 1 and administered Q3W at a dosage of about 90 mg/m$^2$.

8. The method of claim 7, wherein the method comprises a lead phase, optionally followed by a maintenance phase after completion of the lead phase.

9. The method of claim 8, wherein the PD-1 antagonist, the ATR inhibitor and the platinating agent are administered during the lead phase, and wherein during the maintenance phase the PD-1 antagonist but not the ATR inhibitor and the platinating agent are administered.

10. A kit comprising a PD-1 antagonist, an ATR inhibitor and a platinating agent,
wherein the PD-1 antagonist is selected from the group consisting of avelumab, nivolumab, pembrolizumab, atezolizumab, durvalumab and cemiplimab, and
wherein the ATR inhibitor is selected from the group consisting of Compound 1, or a pharmaceutically acceptable salt thereof, Compound 2, or a pharmaceutically acceptable salt thereof, Compound 3, or a pharmaceutically acceptable salt thereof, Compound 4, or a pharmaceutically acceptable salt thereof, and Compound 5, or a pharmaceutically acceptable salt thereof.

* * * * *